United States Patent
Liu et al.

(10) Patent No.: US 10,513,721 B2
(45) Date of Patent: *Dec. 24, 2019

(54) TWO-STAGE PROCESS FOR ENZYMATIC HYDROLYSIS OF LIGNOCELLULOSIC BIOMASS

(71) Applicant: Novozymes A/S, Bagsvaerd (DK)

(72) Inventors: Jiyin Liu, Raleigh, NC (US); James Michael Broering, Wake Forest, NC (US); Keith McFarland, Davis, CA (US); Xin Li, Raleigh, NC (US)

(73) Assignee: Novozymes A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/554,384

(22) PCT Filed: Mar. 11, 2016

(86) PCT No.: PCT/US2016/022101
§ 371 (c)(1),
(2) Date: Aug. 29, 2017

(87) PCT Pub. No.: WO2016/145363
PCT Pub. Date: Sep. 15, 2016

(65) Prior Publication Data
US 2018/0044706 A1  Feb. 15, 2018

Related U.S. Application Data

(60) Provisional application No. 62/132,120, filed on Mar. 12, 2015.

(51) Int. Cl.
| | | |
|---|---|---|
| *C12P 19/14* | (2006.01) | |
| *C12P 7/06* | (2006.01) | |
| *C12P 19/02* | (2006.01) | |
| *C12P 7/10* | (2006.01) | |

(52) U.S. Cl.
CPC .............. *C12P 19/14* (2013.01); *C12P 7/06* (2013.01); *C12P 7/10* (2013.01); *C12P 19/02* (2013.01); *Y02E 50/16* (2013.01); *Y02E 50/17* (2013.01)

(58) Field of Classification Search
None
See application file for complete search history.

(56) References Cited

U.S. PATENT DOCUMENTS

| | | | | |
|---|---|---|---|---|
| 8,148,103 B2* | 4/2012 | Tang | ............ | C07K 14/385 435/267 |
| 2013/0309723 A1* | 11/2013 | Huang | ............ | C12N 9/0065 435/72 |

FOREIGN PATENT DOCUMENTS

| | | |
|---|---|---|
| WO | 2008/134259 A1 | 11/2008 |
| WO | 2009/046524 A2 | 4/2009 |
| WO | 2012/061517 A1 | 5/2012 |
| WO | 2012/130120 A1 | 10/2012 |
| WO | 2013/148504 A2 | 10/2013 |
| WO | 2014/108454 A1 | 7/2014 |
| WO | 2014/130812 A1 | 8/2014 |

OTHER PUBLICATIONS

US20130309723 Alignment to SEQ ID No. 24. Nov. 21, 2013 (Year: 2013).*
US20130309723 Alignment to SEQ ID No. 23 . Nov. 21, 2013 (Year: 2013).*
U.S. Pat. No. 8,148,103 Alignment to SEQ ID No. 8. Apr. 3, 2012. (Year: 2012).*
U.S. Pat. No. 8,148,103 Alignment to SEQ ID No. 7. Apr. 3, 2012. (Year: 2012).*
Chica et al. Curr Opin Biotechnol. Aug. 2005;16(4):378-84. (Year: 2005).*
Singh et al. Curr Protein Pept Sci. 2017, 18, 1-11 (Year: 2017).*

* cited by examiner

*Primary Examiner* — Christian L Fronda
(74) *Attorney, Agent, or Firm* — Robert Starnes

(57) ABSTRACT

The invention relates to processes of multi-stage hydrolysis where different enzyme compositions are added in at least two stages of hydrolysis. In a first stage, a first enzyme composition of one or more cellulolytic enzymes and at least one of an oxidoreductase and an AA9 polypeptide having cellulolytic enhancing activity is added, followed by a latter stage in which a second enzyme composition comprising one or more cellulases is added. Also provided are processes for obtaining hydrolysis products and fermentation products using processes of the invention.

15 Claims, 2 Drawing Sheets

Specification includes a Sequence Listing.

SEQUENCE LISTING

<160> NUMBER OF SEQ ID NOS: 30

<210> SEQ ID NO 1
<211> LENGTH: 1730
<212> TYPE: DNA
<213> ORGANISM: Talaromyces leycettanus

<400> SEQUENCE: 1

```
atggcgtccc tcttctcttt caagatgtac aaggctgctc tcgtcctgtc ttctctcctg      60
gccgctacgc aggctcagca ggccggcact ctcacgacgg agacccatcc gtccctgaca     120
tggcagcaat gctcggccgg tggcagctgc accacccaga acggcaaggt cgtcatcgat     180
gcgaactggc gttgggtgca cagcacgagc ggaagcaaca actgctacac cggcaatacc     240
```

```
tgggacgcta ccctatgccc tgacgatgtg acctgcgccg ccaactgtgc gctggacggt    300
gccgactact cgggcaccta cggagtgacc accagcggca actccctccg cctcaacttc    360
gtcacccagg cgtcacagaa gaacgtcggc tcccgtcttt acctgatgga aatgacaca    420
acctaccaga tcttcaagct gctgaaccag gagttcacct ttgatgtcga tgtgtccaac    480
ctgccgtaag tgacttacca tgaacccctg acgctatctt cttgttggct cccagctgac    540
tggccaattc aagctgcggc ttgaacggtg ctctctacct ggtggccatg gacgccgatg    600
gtggcatggc caagtacccc accaacaagg ctggtgccaa gtacggtacc gggtactgcg    660
actcccagtg tccccgcgac ctcaagttca tcaatggcga ggccaacgtc gagggctggc    720
agccgtcgtc caacgatccc aactctggca ttggcaacca cggatcctgc tgcgcggaga    780
tggatatctg ggaggccaac agcatctcca atgctgtcac tccccacccg tgcgacactc    840
ccggccaggt gatgtgcacc ggtaacaact gcggtggcac atacagcact actcgctatg    900
cgggcacttg cgatcccgac ggctgcgact caaccccta ccgcatgggc aaccacagct    960
tctacggccc taaacagatc gtcgatacca gctcgaagtt caccgtcgtg acgcagttcc   1020
tcacggatga cggcacctcc accggcaccc tctctgaaat ccgccgcttc tatgtccaga   1080
acggccaggt gatcccgaac tcggtgtcga ccatcagtgg cgtgagcggc aactccatca   1140
ccaccgagtt ctgcactgcc agaagcagg ccttcggcga cacggacgac ttctcaaagc   1200
acggcggcct gtccggcatg agcgctgccc tctctcaggg tatggttctg gtcatgagtc   1260
tgtgggatga tgtgagtttg atggacaaac atgcgcgttg acaaagagtc aagcagctga   1320
ctgagatgtt acagcacgcc gccaacatgc tctggctcga cagcacctac ccgaccaacg   1380
cgacctcctc cacccccggt gccgcccgtg aacctgcga catctcgtcc ggtgtccctg   1440
cggatgtcga atccaacgac cccaacgcct acgtggtcta ctcgaacatc aaggttggtc   1500
ccatcggctc gaccttcagc agcagcggct ctggatcttc ttcctctagc tccaccacta   1560
ccacgaccac cgcttcccca accaccacga cctcctccgc atcgagcacc ggcactggag   1620
tggcacagca ctggggccag tgtggtggac agggctggac cggccccaca acctgcgtca   1680
gcccttatac ttgccaggag ctgaacccct actactacca gtgtctgtaa              1730
```

<210> SEQ ID NO 2
<211> LENGTH: 532
<212> TYPE: PRT
<213> ORGANISM: Talaromyces leycettanus

<400> SEQUENCE: 2

Met Ala Ser Leu Phe Ser Phe Lys Met Tyr Lys Ala Ala Leu Val Leu
1               5                   10                  15

Ser Ser Leu Leu Ala Ala Thr Gln Ala Gln Gln Ala Gly Thr Leu Thr
                20                  25                  30

Thr Glu Thr His Pro Ser Leu Thr Trp Gln Gln Cys Ser Ala Gly Gly
        35                  40                  45

Ser Cys Thr Thr Gln Asn Gly Lys Val Val Ile Asp Ala Asn Trp Arg
    50                  55                  60

Trp Val His Ser Thr Ser Gly Ser Asn Asn Cys Tyr Thr Gly Asn Thr
65                  70                  75                  80

Trp Asp Ala Thr Leu Cys Pro Asp Asp Val Thr Cys Ala Ala Asn Cys
                85                  90                  95

Ala Leu Asp Gly Ala Asp Tyr Ser Gly Thr Tyr Gly Val Thr Thr Ser
            100                 105                 110

-continued

Gly Asn Ser Leu Arg Leu Asn Phe Val Thr Gln Ala Ser Gln Lys Asn
            115                 120                 125

Val Gly Ser Arg Leu Tyr Leu Met Glu Asn Asp Thr Thr Tyr Gln Ile
130                 135                 140

Phe Lys Leu Leu Asn Gln Glu Phe Thr Phe Asp Val Asp Val Ser Asn
145                 150                 155                 160

Leu Pro Cys Gly Leu Asn Gly Ala Leu Tyr Leu Val Ala Met Asp Ala
                    165                 170                 175

Asp Gly Gly Met Ala Lys Tyr Pro Thr Asn Lys Ala Gly Ala Lys Tyr
                180                 185                 190

Gly Thr Gly Tyr Cys Asp Ser Gln Cys Pro Arg Asp Leu Lys Phe Ile
            195                 200                 205

Asn Gly Glu Ala Asn Val Glu Gly Trp Gln Pro Ser Ser Asn Asp Pro
        210                 215                 220

Asn Ser Gly Ile Gly Asn His Gly Ser Cys Cys Ala Glu Met Asp Ile
225                 230                 235                 240

Trp Glu Ala Asn Ser Ile Ser Asn Ala Val Thr Pro His Pro Cys Asp
                245                 250                 255

Thr Pro Gly Gln Val Met Cys Thr Gly Asn Asn Cys Gly Gly Thr Tyr
            260                 265                 270

Ser Thr Thr Arg Tyr Ala Gly Thr Cys Asp Pro Asp Gly Cys Asp Phe
        275                 280                 285

Asn Pro Tyr Arg Met Gly Asn His Ser Phe Tyr Gly Pro Lys Gln Ile
        290                 295                 300

Val Asp Thr Ser Ser Lys Phe Thr Val Val Thr Gln Phe Leu Thr Asp
305                 310                 315                 320

Asp Gly Thr Ser Thr Gly Thr Leu Ser Glu Ile Arg Arg Phe Tyr Val
                325                 330                 335

Gln Asn Gly Gln Val Ile Pro Asn Ser Val Ser Thr Ile Ser Gly Val
            340                 345                 350

Ser Gly Asn Ser Ile Thr Thr Glu Phe Cys Thr Ala Gln Lys Gln Ala
        355                 360                 365

Phe Gly Asp Thr Asp Asp Phe Ser Lys His Gly Gly Leu Ser Gly Met
        370                 375                 380

Ser Ala Ala Leu Ser Gln Gly Met Val Leu Val Met Ser Leu Trp Asp
385                 390                 395                 400

Asp His Ala Ala Asn Met Leu Trp Leu Asp Ser Thr Tyr Pro Thr Asn
                405                 410                 415

Ala Thr Ser Ser Thr Pro Gly Ala Ala Arg Gly Thr Cys Asp Ile Ser
            420                 425                 430

Ser Gly Val Pro Ala Asp Val Glu Ser Asn Asp Pro Asn Ala Tyr Val
        435                 440                 445

Val Tyr Ser Asn Ile Lys Val Gly Pro Ile Gly Ser Thr Phe Ser Ser
450                 455                 460

Ser Gly Ser Gly Ser Ser Ser Ser Ser Thr Thr Thr Thr Thr
465                 470                 475                 480

Ala Ser Pro Thr Thr Thr Thr Ser Ser Ala Ser Ser Thr Gly Thr Gly
            485                 490                 495

Val Ala Gln His Trp Gly Gln Cys Gly Gly Gln Gly Trp Thr Gly Pro
                500                 505                 510

Thr Thr Cys Val Ser Pro Tyr Thr Cys Gln Glu Leu Asn Pro Tyr Tyr
            515                 520                 525

Tyr Gln Cys Leu
    530

<210> SEQ ID NO 3
<211> LENGTH: 1898
<212> TYPE: DNA
<213> ORGANISM: Talaromyces leycettanus

<400> SEQUENCE: 3

```
atgcggtctc tcctggctct tgcccctacc ctgctcgcgc tgttgttca ggctcagcaa        60
accatgtggg gtcaatgtaa gttcttttca ctgcttacca tgtataatct ttgatatcaa       120
gcatcatatc tgactcacgt tttaggcggt ggtcagggct ggaccggacc taccatctgt       180
gtagcaggcg cgacatgcag cacacagaac ccttgtaagt cgggccttca tcaaaacttc       240
aacatcacca cctcgatgga gcaggagttg acctgatctt tacccttagg gtatgcgcag       300
tgcaccccag cacctaccgc gccgacgacc ttgcaaacaa caactacgac gagctcgaaa       360
tcgtccacga ccacgagctc gaagtcgtcc acgaccacag gtggaagtgg cggtggaact       420
acgacctcaa cgtcagccac catcaccgcg gctccatctg gtaacccata ctccggatac       480
cagctctatg tgaaccagga atactcgtcc gaggtgtacg cgtctgctat tccttcccctt      540
accggcactc tggtcgcgaa ggcaagcgcc gcggcagagg tgccatcttt cctgtggctg       600
taagttttt tgaccttgaa tgaacgccct gtcctctacg agtggccgca ggagctaatt        660
gagatgccaa tgaacaggga cactgcctcc aaggtgccac tgatgggcac ttacttgcag       720
gatatccagg cgaagaacgc tgctggcgcc aaccccccat atgccggtca attcgtggtt       780
tacgacttgc cggatcgtga ttgcgctgca ttggccagca atggagagta ctccattgct       840
aacaatggtg ttgccaacta caaggcttac atcgactcca tccgcgcgct tcttgttcaa       900
tactcgaacg tccatgtcat cctgtgtgatc ggtgagctat tgcagtctcg ctttaaagca      960
tttgactaga tcaatgtcgc taatggtacc taccgcacag agcccgacag cttggccaac      1020
cttgtcacca acctgaatgt tcagaagtgt gctaatgctc agagtgctta cctggagtgc      1080
atcaactatg ccctcactca gttgaacctc aagaacgttg ctatgtacat cgatgctggt      1140
gcgtgaacct tccctagtca gcccaaaata actgaaataa agagacggag tgtactgatt      1200
gtcatgcagg tcatgctgga tggctcggct ggcccgccaa ccttagcccg gccgctcaac      1260
tctttgcttc cgtataccag aatgcaagct ccccagctgc cgttcgcggc ctggcaacca      1320
acgtggccaa ctataatgcc tggtcgatcg ccacttgccc atcttacacc caaggcgacc      1380
ccaactgcga cgagcagaaa tacatcaacg ctctggctcc attgcttcag caacagggat      1440
ggtcatcagt tcactttatc accgataccg gtaagtctgc ctgtcctgcc aaccatgcgt      1500
tcaagagcgt tgcaatccta accatgctgg tatcttccag gccgtaacgg tgtccagcct      1560
accaagcaga atgcctgggg tgactggtgc aacgttatcg gaaccggctt cggtgtccgt      1620
cccaccacca acactggcga tccattggag gatgctttcg tctgggtcaa gcctggtggt      1680
gagagtgatg gtacttccaa ctccacttcg cctcgctacg acgcccactg cggttacagt      1740
gatgctcttc agcctgctcc tgaggctggt acctggttcg aggtaagctt ctgcatactg      1800
agatcgagaa tcctgaaagg gttaacctgc taatgcttcg gtgtttgata taggcttact      1860
ttgagcaact ccttaccaac gccaaccccct ctttctaa                             1898
```

<210> SEQ ID NO 4
<211> LENGTH: 464
<212> TYPE: PRT

<213> ORGANISM: Talaromyces leycettanus

<400> SEQUENCE: 4

```
Met Arg Ser Leu Leu Ala Leu Ala Pro Thr Leu Leu Ala Pro Val Val
1               5                   10                  15

Gln Ala Gln Gln Thr Met Trp Gly Gln Cys Gly Gly Gln Gly Trp Thr
            20                  25                  30

Gly Pro Thr Ile Cys Val Ala Gly Ala Thr Cys Ser Thr Gln Asn Pro
                35                  40                  45

Trp Tyr Ala Gln Cys Thr Pro Ala Pro Thr Ala Pro Thr Thr Leu Gln
    50                  55                  60

Thr Thr Thr Thr Thr Ser Ser Lys Ser Ser Thr Thr Ser Ser Lys
65                  70                  75                  80

Ser Ser Thr Thr Thr Gly Gly Ser Gly Gly Gly Thr Thr Thr Ser Thr
                85                  90                  95

Ser Ala Thr Ile Thr Ala Ala Pro Ser Gly Asn Pro Tyr Ser Gly Tyr
                100                 105                 110

Gln Leu Tyr Val Asn Gln Glu Tyr Ser Ser Glu Val Tyr Ala Ser Ala
            115                 120                 125

Ile Pro Ser Leu Thr Gly Thr Leu Val Ala Lys Ala Ser Ala Ala Ala
130                 135                 140

Glu Val Pro Ser Phe Leu Trp Leu Asp Thr Ala Ser Lys Val Pro Leu
145                 150                 155                 160

Met Gly Thr Tyr Leu Gln Asp Ile Gln Ala Lys Asn Ala Ala Gly Ala
                165                 170                 175

Asn Pro Pro Tyr Ala Gly Gln Phe Val Val Tyr Asp Leu Pro Asp Arg
            180                 185                 190

Asp Cys Ala Ala Leu Ala Ser Asn Gly Glu Tyr Ser Ile Ala Asn Asn
        195                 200                 205

Gly Val Ala Asn Tyr Lys Ala Tyr Ile Asp Ser Ile Arg Ala Leu Leu
    210                 215                 220

Val Gln Tyr Ser Asn Val His Val Ile Leu Val Ile Glu Pro Asp Ser
225                 230                 235                 240

Leu Ala Asn Leu Val Thr Asn Leu Asn Val Gln Lys Cys Ala Asn Ala
                245                 250                 255

Gln Ser Ala Tyr Leu Glu Cys Ile Asn Tyr Ala Leu Thr Gln Leu Asn
            260                 265                 270

Leu Lys Asn Val Ala Met Tyr Ile Asp Ala Gly His Ala Gly Trp Leu
        275                 280                 285

Gly Trp Pro Ala Asn Leu Ser Pro Ala Ala Gln Leu Phe Ala Ser Val
    290                 295                 300

Tyr Gln Asn Ala Ser Ser Pro Ala Ala Val Arg Gly Leu Ala Thr Asn
305                 310                 315                 320

Val Ala Asn Tyr Asn Ala Trp Ser Ile Ala Thr Cys Pro Ser Tyr Thr
                325                 330                 335

Gln Gly Asp Pro Asn Cys Asp Glu Gln Lys Tyr Ile Asn Ala Leu Ala
            340                 345                 350

Pro Leu Leu Gln Gln Gln Gly Trp Ser Ser Val His Phe Ile Thr Asp
        355                 360                 365

Thr Gly Arg Asn Gly Val Gln Pro Thr Lys Gln Asn Ala Trp Gly Asp
    370                 375                 380

Trp Cys Asn Val Ile Gly Thr Gly Phe Gly Val Arg Pro Thr Thr Asn
385                 390                 395                 400
```

```
Thr Gly Asp Pro Leu Glu Asp Ala Phe Val Trp Val Lys Pro Gly Gly
            405                 410                 415

Glu Ser Asp Gly Thr Ser Asn Ser Thr Ser Pro Arg Tyr Asp Ala His
        420                 425                 430

Cys Gly Tyr Ser Asp Ala Leu Gln Pro Ala Pro Glu Ala Gly Thr Trp
    435                 440                 445

Phe Glu Ala Tyr Phe Glu Gln Leu Leu Thr Asn Ala Asn Pro Ser Phe
450                 455                 460

<210> SEQ ID NO 5
<211> LENGTH: 3060
<212> TYPE: DNA
<213> ORGANISM: Aspergillus fumigatus

<400> SEQUENCE: 5
```

| | |
|---|---|
| atgagattcg gttggctcga ggtggccgct ctgacggccg cttctgtagc caatgcccag | 60 |
| gtttgtgatg cttttcccgtc attgtttcgg atatagttga caatagtcat ggaaataatc | 120 |
| aggaattggc tttctctcca ccattctacc cttcgccttg ggctgatggc cagggagagt | 180 |
| gggcagatgc ccatcgacgc gccgtcgaga tcgtttctca gatgacactg gcggagaagg | 240 |
| ttaaccttac aacgggtact gggtggggttg cgacttttt gttgacagtg agctttcttc | 300 |
| actgaccatc tacacagatg gaaatggac cgatgcgtcg gtcaaaccgg cagcgttccc | 360 |
| aggtaagctt gcaattctgc aacaacgtgc aagtgtagtt gctaaaacgc ggtggtgcag | 420 |
| acttggtatc aactggggtc tttgtggcca ggattcccct tgggtatccc gtttctgtga | 480 |
| gctatacccg cggagtcttt cagtccttgt attatgtgct gatgattgtc tctgtatagc | 540 |
| tgacctcaac tccgccttcc ctgctggtac taatgtcgcc gcgacatggg acaagacact | 600 |
| cgcctacctt cgtggcaagg ccatgggtga ggaattcaac gacaagggcg tggacatttt | 660 |
| gctggggcct gctgctggtc ctctcggcaa atacccggac ggcggcagaa tctgggaagg | 720 |
| cttctctcct gatccggttc tcactggtgt acttttcgcc gaaactatca agggtatcca | 780 |
| agacgcgggt gtgattgcta ctgccaagca ttacattctg aatgaacagg agcatttccg | 840 |
| acaggttggc gaggcccagg atatggttca acatcacg gagacgatca gctccaacgt | 900 |
| ggatgacaag accatgcacg agttgtacct ttggtgagta gttgacactg caaatgagga | 960 |
| ccttgattga tttgactgac ctggaatgca ggcccttgc agatgctgtg cgcggtaaga | 1020 |
| ttttccgtag acttgacctc gcgacgaaga atcgctgac gaaccatcgt agctggcgtt | 1080 |
| ggcgctgtca tgtgttccta caatcaaatc aacaacagct acggttgtca aaacagtcaa | 1140 |
| actctcaaca agctcctcaa ggctgagctg gcttccaag gcttcgtcat gagtgactgg | 1200 |
| agcgctcacc acagcggtgt cggcgctgcc ctcgctgggt tggatatgtc gatgcctgga | 1260 |
| gacatttcct tcgacgacgg actctccttc tggggcacga acctaactgt cagtgttctt | 1320 |
| aacggcaccg ttccagcctg gcgtgtcgat gacatggctg ttcgtatcat accgcgtac | 1380 |
| tacaaggttg gtcgtgaccg tcttcgtatt ccccctaact tcagctcctg gacccgggat | 1440 |
| gagtacggct gggagcattc tgctgtctcc gagggagcct ggaccaaggt gaacgacttc | 1500 |
| gtcaatgtgc agcgcagtca ctctcagatc atccgtgaga ttggtgccgc tagtacagtg | 1560 |
| ctcttgaaga acacgggtgc tcttcctttg accggcaagg aggttaaagt gggtgttctc | 1620 |
| ggtgaagacg ctggttccaa cccgtggggt gctaacggct gccccgaccg cggctgtgat | 1680 |
| aacggcactc ttgctatggc ctgggggtagt ggtactgcca acttccctta ccttgtcacc | 1740 |
| cccgagcagg ctatccagcg agaggtcatc agcaacggcg gcaatgtctt tgctgtgact | 1800 |

```
gataacgggg ctctcagcca gatggcagat gttgcatctc aatccaggtg agtgcgggct    1860
cttagaaaaa gaacgttctc tgaatgaagt tttttaacca ttgcgaacag cgtgtctttg    1920
gtgtttgtca acgccgactc tggagagggt ttcatcagtg tcgacggcaa cgagggtgac    1980
cgcaaaaatc tcactctgtg gaagaacggc gaggccgtca ttgacactgt tgtcagccac    2040
tgcaacaaca cgattgtggt tattcacagt gttgggcccg tcttgatcga ccggtggtat    2100
gataacccca acgtcactgc catcatctgg gccggcttgc ccggtcagga gagtggcaac    2160
tccctggtcg acgtgctcta tggccgcgtc aaccccagcg ccaagacccc gttcacctgg    2220
ggcaagactc gggagtctta cggggctccc ttgctcaccg agcctaacaa tggcaatggt    2280
gctccccagg atgatttcaa cgagggcgtc ttcattgact accgtcactt tgacaagcgc    2340
aatgagaccc ccatttatga gtttggccat ggcttgagct acaccacctt tggttactct    2400
caccttcggg ttcaggccct caatagttcg agttcggcat atgtcccgac tagcggagag    2460
accaagcctg cgccaaccta tgtgagatc ggtagtgccg ccgactacct gtatcccgag    2520
ggtctcaaaa gaattaccaa gtttatttac ccttggctca actcgaccga cctcgaggat    2580
tcttctgacg acccgaacta cggctgggag gactcggagt acattcccga aggcgctagg    2640
gatgggtctc ctcaacccct cctgaaggct ggcggcgctc ctggtggtaa ccctacccct    2700
tatcaggatc ttgttagggt gtcggccacc ataaccaaca ctggtaacgt cgccggttat    2760
gaagtccctc aattggtgag tgacccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
ctcgccaatt gggatgtgga ggctcaggac tgggtcatca caaagtaccc caagaaagtg    3000
cacgtcggca gctcctcgcg taagctgcct ctgagagcgc ctctgccccg tgtctactag    3060
```

<210> SEQ ID NO 6
<211> LENGTH: 863
<212> TYPE: PRT
<213> ORGANISM: Aspergillus fumigatus

<400> SEQUENCE: 6

```
Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
                20                  25                  30

Trp Ala Asp Gly Gln Gly Glu Trp Ala Asp Ala His Arg Arg Ala Val
            35                  40                  45

Glu Ile Val Ser Gln Met Thr Leu Ala Glu Lys Val Asn Leu Thr Thr
        50                  55                  60

Gly Thr Gly Trp Glu Met Asp Arg Cys Val Gly Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Phe Ser Asp Leu Asn Ser Ala Phe Pro Ala Gly Thr Asn
                100                 105                 110

Val Ala Ala Thr Trp Asp Lys Thr Leu Ala Tyr Leu Arg Gly Lys Ala
            115                 120                 125

Met Gly Glu Glu Phe Asn Asp Lys Gly Val Asp Ile Leu Leu Gly Pro
        130                 135                 140

Ala Ala Gly Pro Leu Gly Lys Tyr Pro Asp Gly Gly Arg Ile Trp Glu
```

-continued

```
145                 150                 155                 160
Gly Phe Ser Pro Asp Pro Val Leu Thr Gly Val Leu Phe Ala Glu Thr
                165                 170                 175
Ile Lys Gly Ile Gln Asp Ala Gly Val Ile Ala Thr Ala Lys His Tyr
                180                 185                 190
Ile Leu Asn Glu Gln Glu His Phe Arg Gln Val Gly Glu Ala Gln Gly
                195                 200                 205
Tyr Gly Tyr Asn Ile Thr Glu Thr Ile Ser Ser Asn Val Asp Asp Lys
    210                 215                 220
Thr Met His Glu Leu Tyr Leu Trp Pro Phe Ala Asp Ala Val Arg Ala
225                 230                 235                 240
Gly Val Gly Ala Val Met Cys Ser Tyr Asn Gln Ile Asn Asn Ser Tyr
                245                 250                 255
Gly Cys Gln Asn Ser Gln Thr Leu Asn Lys Leu Leu Lys Ala Glu Leu
                260                 265                 270
Gly Phe Gln Gly Phe Val Met Ser Asp Trp Ser Ala His His Ser Gly
                275                 280                 285
Val Gly Ala Ala Leu Ala Gly Leu Asp Met Ser Met Pro Gly Asp Ile
    290                 295                 300
Ser Phe Asp Asp Gly Leu Ser Phe Trp Gly Thr Asn Leu Thr Val Ser
305                 310                 315                 320
Val Leu Asn Gly Thr Val Pro Ala Trp Arg Val Asp Asp Met Ala Val
                325                 330                 335
Arg Ile Met Thr Ala Tyr Tyr Lys Val Gly Arg Asp Arg Leu Arg Ile
                340                 345                 350
Pro Pro Asn Phe Ser Ser Trp Thr Arg Asp Glu Tyr Gly Trp Glu His
                355                 360                 365
Ser Ala Val Ser Glu Gly Ala Trp Thr Lys Val Asn Asp Phe Val Asn
    370                 375                 380
Val Gln Arg Ser His Ser Gln Ile Ile Arg Glu Ile Gly Ala Ala Ser
385                 390                 395                 400
Thr Val Leu Leu Lys Asn Thr Gly Ala Leu Pro Leu Thr Gly Lys Glu
                405                 410                 415
Val Lys Val Gly Val Leu Gly Glu Asp Ala Gly Ser Asn Pro Trp Gly
                420                 425                 430
Ala Asn Gly Cys Pro Asp Arg Gly Cys Asp Asn Gly Thr Leu Ala Met
                435                 440                 445
Ala Trp Gly Ser Gly Thr Ala Asn Phe Pro Tyr Leu Val Thr Pro Glu
    450                 455                 460
Gln Ala Ile Gln Arg Glu Val Ile Ser Asn Gly Gly Asn Val Phe Ala
465                 470                 475                 480
Val Thr Asp Asn Gly Ala Leu Ser Gln Met Ala Asp Val Ala Ser Gln
                485                 490                 495
Ser Ser Val Ser Leu Val Phe Val Asn Ala Asp Ser Gly Glu Gly Phe
                500                 505                 510
Ile Ser Val Asp Gly Asn Glu Gly Asp Arg Lys Asn Leu Thr Leu Trp
                515                 520                 525
Lys Asn Gly Glu Ala Val Ile Asp Thr Val Ser His Cys Asn Asn
    530                 535                 540
Thr Ile Val Val Ile His Ser Val Gly Pro Val Leu Ile Asp Arg Trp
545                 550                 555                 560
Tyr Asp Asn Pro Asn Val Thr Ala Ile Ile Trp Ala Gly Leu Pro Gly
                565                 570                 575
```

Gln Glu Ser Gly Asn Ser Leu Val Asp Val Leu Tyr Gly Arg Val Asn
            580                 585                 590

Pro Ser Ala Lys Thr Pro Phe Thr Trp Gly Lys Thr Arg Glu Ser Tyr
        595                 600                 605

Gly Ala Pro Leu Leu Thr Glu Pro Asn Gly Asn Gly Ala Pro Gln
        610                 615                 620

Asp Asp Phe Asn Glu Gly Val Phe Ile Asp Tyr Arg His Phe Asp Lys
625                 630                 635                 640

Arg Asn Glu Thr Pro Ile Tyr Glu Phe Gly His Gly Leu Ser Tyr Thr
                645                 650                 655

Thr Phe Gly Tyr Ser His Leu Arg Val Gln Ala Leu Asn Ser Ser Ser
            660                 665                 670

Ser Ala Tyr Val Pro Thr Ser Gly Glu Thr Lys Pro Ala Pro Thr Tyr
        675                 680                 685

Gly Glu Ile Gly Ser Ala Ala Asp Tyr Leu Tyr Pro Glu Gly Leu Lys
        690                 695                 700

Arg Ile Thr Lys Phe Ile Tyr Pro Trp Leu Asn Ser Thr Asp Leu Glu
705                 710                 715                 720

Asp Ser Ser Asp Asp Pro Asn Tyr Gly Trp Glu Asp Ser Glu Tyr Ile
                725                 730                 735

Pro Glu Gly Ala Arg Asp Gly Ser Pro Gln Pro Leu Leu Lys Ala Gly
            740                 745                 750

Gly Ala Pro Gly Gly Asn Pro Thr Leu Tyr Gln Asp Leu Val Arg Val
        755                 760                 765

Ser Ala Thr Ile Thr Asn Thr Gly Asn Val Ala Gly Tyr Glu Val Pro
        770                 775                 780

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
                805                 810                 815

Thr Thr Thr Leu Asn Arg Arg Asp Leu Ala Asn Trp Asp Val Glu Ala
            820                 825                 830

Gln Asp Trp Val Ile Thr Lys Tyr Pro Lys Lys Val His Val Gly Ser
        835                 840                 845

Ser Ser Arg Lys Leu Pro Leu Arg Ala Pro Leu Pro Arg Val Tyr
850                 855                 860

<210> SEQ ID NO 7
<211> LENGTH: 835
<212> TYPE: DNA
<213> ORGANISM: Penicillium sp. emersonii

<400> SEQUENCE: 7
atgctgtctt cgacgactcg caccctcgcc tttacaggcc ttgcgggcct tctgtccgct    60
cccctggtca aggcccatgg ctttgtccag ggcattgtca tcggtgacca attgtaagtc   120
cctctcttgc agttctgtcg attaactgct ggactgcttg cttgactccc tgctgactcc   180
caacagctac agcgggtaca tcgtcaactc gttcccctac gaatccaacc caccccccgt   240
catcggctgg gccacgaccg ccaccgacct gggcttcgtc gacggcacag gataccaagg   300
cccggacatc atctgccacc ggaatgcgac gcccgcgccg ctgacagccc cgtggccgc    360 cggcggcacc gtcgagctgc agtggacgcc gtggccggac agccaccacg gacccgtcat   420
cacctacctg gcgccgtgca acggcaactg ctcgaccgtc gacaagacga cgctggagtt   480

```
cttcaagatc gaccagcagg gcctgatcga cgacacgagc ccgccgggca cctgggcgtc      540
ggacaacctc atcgccaaca acaatagctg gaccgtcacc attcccaaca gcgtcgcccc      600
cggcaactac gtcctgcgcc acgagatcat cgccctgcac tcggccaaca acaaggacgg      660
cgcccagaac tacccccagt gcatcaacat cgaggtcacg ggcggcggct ccgacgcgcc      720
tgagggtact ctgggcgagg atctctacca tgacaccgac ccgggcattc tggtcgacat      780
ttacgagccc attgcgacgt ataccattcc ggggccgcct gagccgacgt tctag          835
```

<210> SEQ ID NO 8
<211> LENGTH: 253
<212> TYPE: PRT
<213> ORGANISM: Penicillium sp. emersonii

<400> SEQUENCE: 8

```
Met Leu Ser Ser Thr Thr Arg Thr Leu Ala Phe Thr Gly Leu Ala Gly
1               5                   10                  15

Leu Leu Ser Ala Pro Leu Val Lys Ala His Gly Phe Val Gln Gly Ile
            20                  25                  30

Val Ile Gly Asp Gln Phe Tyr Ser Gly Tyr Ile Val Asn Ser Phe Pro
        35                  40                  45

Tyr Glu Ser Asn Pro Pro Val Ile Gly Trp Ala Thr Thr Ala Thr
    50                  55                  60

Asp Leu Gly Phe Val Asp Gly Thr Gly Tyr Gln Gly Pro Asp Ile Ile
65                  70                  75                  80

Cys His Arg Asn Ala Thr Pro Ala Pro Leu Thr Ala Pro Val Ala Ala
                85                  90                  95

Gly Gly Thr Val Glu Leu Gln Trp Thr Pro Trp Pro Asp Ser His His
            100                 105                 110

Gly Pro Val Ile Thr Tyr Leu Ala Pro Cys Asn Gly Asn Cys Ser Thr
        115                 120                 125

Val Asp Lys Thr Thr Leu Glu Phe Phe Lys Ile Asp Gln Gln Gly Leu
    130                 135                 140

Ile Asp Asp Thr Ser Pro Pro Gly Thr Trp Ala Ser Asp Asn Leu Ile
145                 150                 155                 160

Ala Asn Asn Asn Ser Trp Thr Val Thr Ile Pro Asn Ser Val Ala Pro
                165                 170                 175

Gly Asn Tyr Val Leu Arg His Glu Ile Ile Ala Leu His Ser Ala Asn
            180                 185                 190

Asn Lys Asp Gly Ala Gln Asn Tyr Pro Gln Cys Ile Asn Ile Glu Val
        195                 200                 205

Thr Gly Gly Gly Ser Asp Ala Pro Glu Gly Thr Leu Gly Glu Asp Leu
    210                 215                 220

Tyr His Asp Thr Asp Pro Gly Ile Leu Val Asp Ile Tyr Glu Pro Ile
225                 230                 235                 240

Ala Thr Tyr Thr Ile Pro Gly Pro Pro Glu Pro Thr Phe
                245                 250
```

<210> SEQ ID NO 9
<211> LENGTH: 1520
<212> TYPE: DNA
<213> ORGANISM: Talaromyces leycettanus

<400> SEQUENCE: 9

```
atggtccatc tttcttccct ggccctggct ttggccgccg ctcgcagct gtatgtgatc       60 catgccatga ctcgagaagt gctcccaaaa ctgactccaa gtctcaatct tagtgcccaa      120
```

```
gctgcaggtc ttaacactgc tgccaaagcg attggaaagc tctatttcgg taccgcaacc      180
gacaacccgg agctgtccga cagcacatac atgcaggaga cggataacac cgatgatttc      240
ggccaactca ccccagctaa ctccatgaag gttcgctgac atcttagttc ccccccctt       300 ttgggaatct gcgcggagat atgctgagcc ttcaaaacta gtgggatgcc accgagccct      360
ctcagaacac cttcaccttc accaacggtg atcagatcgc aaaccttgct aagagcaacg      420
gtcagatgct gagatgccac aacctggtgt ggtacaacca gttgcccagc tggggtaagc      480
aaccggttct gttaatatca tcagcgtgac cgcatcgatc gtattgcgcg agattggaa       540 agatttgcaa gctaatgtca ctacagtcac cagcggatct tggaccaatg ccacgcttct      600 tgccggccatg aagaaccaca tcaccaacgt tgtgacccac tacaagggac agtgctacgc     660
ttgggatgtt gtcaacgaag gtacgtttcg attcggcttc cctcggaccg tatctgcagg      720
caaaaaggtc aatcaattga caatcgtgat ccccagctct caacgatgat ggcacctacc      780
gatccaatgt cttctatcag tacatcggcg aggcatacat tcccattgcc tttgcgaccg      840
ctgccgccgc cgatccaaac gcgaagctct actacaacga ctacaacatt gagtaccccg      900
gcgccaaggc caccgccgcc cagaacatcg tcaagatggt caaggcttac ggcgcgaaaa      960
tcgacggtgt cggtctgcaa tctcacttca tcgttggcag cacccctagc cagagctccc     1020
agcagagcaa catggctgct ttcaccgcgc tcggcgtcga ggtcgccatc accgaactgg     1080
atatccgcat gacgttgcct tccaccagtg ctctcttggc ccagcaatcc accgattacc     1140
agagcactgt gtcggcttgc gtgaacactc cgaagtgcat tggtatcacc ctctgggact     1200
ggaccgacaa gtactcctgg gttcccaaca ccttctccgg ccaaggtgac gcctgcccct     1260
gggattctaa ctaccagaag aagcctgcct actacggtat cttgactgcg ctcggaggca     1320
gcgcttccac ctccaccacc accactctgg tgacctccac caggacttcg actacgacca     1380
gcacttcggc cacctccacg tctactggcg ttgctcagca ctggggccag tgcggtggta     1440
tcggctggac agggccgact acctgcgcta gcccctacac ctgccaggaa ctgaatccct     1500
actactacca gtgcctgtaa                                                  1520
```

<210> SEQ ID NO 10
<211> LENGTH: 405
<212> TYPE: PRT
<213> ORGANISM: Talaromyces leycettanus

<400> SEQUENCE: 10

Met Val His Leu Ser Ser Leu Ala Leu Ala Ala Gly Ser Gln
1               5                   10

Leu Ala Gln Ala Ala Gly Leu Asn Thr Ala Ala Lys Ala Ile Gly Lys
                20                  25                  30

Leu Tyr Phe Gly Thr Ala Thr Asp Asn Pro Glu Leu Ser Asp Ser Thr
            35                  40                  45

Tyr Met Gln Glu Thr Asp Asn Thr Asp Asp Phe Gly Gln Leu Thr Pro
        50                  55                  60

Ala Asn Ser Met Lys Trp Asp Ala Thr Glu Pro Ser Gln Asn Thr Phe
65                  70                  75                  80

Thr Phe Thr Asn Gly Asp Gln Ile Ala Asn Leu Ala Lys Ser Asn Gly
                85                  90                  95

Gln Met Leu Arg Cys His Asn Leu Val Trp Tyr Asn Gln Leu Pro Ser
            100                 105                 110

Trp Val Thr Ser Gly Ser Trp Thr Asn Ala Thr Leu Leu Ala Ala Met

|     | 115 |     |     |     | 120 |     |     |     | 125 |     |     |
| --- | --- | --- | --- | --- | --- | --- | --- | --- | --- | --- | --- |

Lys Asn His Ile Thr Asn Val Val Thr His Tyr Lys Gly Gln Cys Tyr
        130                 135                 140

Ala Trp Asp Val Val Asn Glu Ala Leu Asn Asp Asp Gly Thr Tyr Arg
145                 150                 155                 160

Ser Asn Val Phe Tyr Gln Tyr Ile Gly Glu Ala Tyr Ile Pro Ile Ala
                165                 170                 175

Phe Ala Thr Ala Ala Ala Asp Pro Asn Ala Lys Leu Tyr Tyr Asn
            180                 185                 190

Asp Tyr Asn Ile Glu Tyr Pro Gly Ala Lys Ala Thr Ala Ala Gln Asn
            195                 200                 205

Ile Val Lys Met Val Lys Ala Tyr Gly Ala Lys Ile Asp Gly Val Gly
        210                 215                 220

Leu Gln Ser His Phe Ile Val Gly Ser Thr Pro Ser Gln Ser Ser Gln
225                 230                 235                 240

Gln Ser Asn Met Ala Ala Phe Thr Ala Leu Gly Val Glu Val Ala Ile
                245                 250                 255

Thr Glu Leu Asp Ile Arg Met Thr Leu Pro Ser Thr Ser Ala Leu Leu
            260                 265                 270

Ala Gln Gln Ser Thr Asp Tyr Gln Ser Thr Val Ser Ala Cys Val Asn
            275                 280                 285

Thr Pro Lys Cys Ile Gly Ile Thr Leu Trp Asp Trp Thr Asp Lys Tyr
        290                 295                 300

Ser Trp Val Pro Asn Thr Phe Ser Gly Gln Gly Asp Ala Cys Pro Trp
305                 310                 315                 320

Asp Ser Asn Tyr Gln Lys Lys Pro Ala Tyr Tyr Gly Ile Leu Thr Ala
                325                 330                 335

Leu Gly Gly Ser Ala Ser Thr Ser Thr Thr Thr Leu Val Thr Ser
            340                 345                 350

Thr Arg Thr Ser Thr Thr Thr Ser Thr Ser Ala Thr Ser Thr Ser Thr
            355                 360                 365

Gly Val Ala Gln His Trp Gly Gln Cys Gly Gly Ile Gly Trp Thr Gly
        370                 375                 380

Pro Thr Thr Cys Ala Ser Pro Tyr Thr Cys Gln Glu Leu Asn Pro Tyr
385                 390                 395                 400

Tyr Tyr Gln Cys Leu
            405

<210> SEQ ID NO 11
<211> LENGTH: 2391
<212> TYPE: DNA
<213> ORGANISM: Talaromyces emersonii

<400> SEQUENCE: 11

```
atgatgactc ccacggcgat tctcaccgca gtggcggcgc tcctgcccac cgcgacatgg      60
gcacaggata accaaaccta tgccaattac tcgtcgcagt ctcagccgga cctgtttccc     120
cggaccgtcg cgaccatcga cctgtccttc cccgactgtg agaatggccc gctcagcacg     180
aacctggtgt gcaacaaatc ggccgatccc tgggcccgag ctgaggccct catctcgctc     240
tttaccctcg aagagctgat taacaacacc cagaacaccg ctcctggcgt gccccgtttg     300
ggtctgcccc agtatcaggt gtggaatgaa gctctgcacg gactggaccg cgccaatttc     360
tcccattcgg gcgaatacag ctgggccacg tccttcccca tgcccatcct gtcgatggcg     420
tccttcaacc ggaccctcat caaccagatt gcctccatca ttgcaacgca agcccgtgcc     480
```

```
ttcaacaacg ccggccgtta cggccttgac agctatgcgc ccaacatcaa tggcttccgc    540
agtcccctct ggggccgtgg acaggagacg cctggtgagg atgcgttctt cttgagttcc    600
acctatgcgt acgagtacat cacaggcctg cagggcggtg tcgacccaga gcatgtcaag    660
atcgtcgcga cggcgaagca cttcgccggc tatgatctgg agaactgggg caacgtctct    720
cggctggggt tcaatgctat catcacgcag caggatctct ccgagtacta caccctcag    780
ttcctggcgt ctgctcgata cgccaagacg cgcagcatca tgtgctccta caatgcagtg    840
aatggagtcc caagctgtgc caactccttc ttcctccaga cgcttctccg agaaaacttt    900
gacttcgttg acgacgggta cgtctcgtcg gattgcgacg ccgtctacaa cgtcttcaac    960
ccacacggtt acgcccttaa ccagtcggga gccgctgcgg actcgctcct agcaggtacc   1020
gatatcgact gtggtcagac cttgccgtgg cacctgaatg agtccttcgt agaaggatac   1080
gtctcccgcg gtgatatcga gaatccctc cccgtctct actcaaacct ggtgcgtctc    1140
ggctactttg acggcaacaa cagcgagtac cgcaacctca actggaacga cgtcgtgact   1200
acggacgcct ggaacatctc gtacgaggcc gcggtggaag gtatcaccct gctcaagaac   1260
gacgaacgc tgccgctgtc caagaaggtc cgcagcattg cgctcatcgg tccttgggcc   1320
aatgccacgg tgcagatgca gggtaactac tatggaacgc caccgtatct gatcagtccg   1380
ctggaagccg ccaaggccag tgggttcacg gtcaactatg cattcggtac caacatctcg   1440
accgattcta cccagtggtt cgcggaagcc atcgcggcgg cgaagaagtc ggacgtgatc   1500
atctacgccg gtggtattga caacacgatc gaggcagagg acaggaccg cacggatctc    1560
aagtggccgg ggaaccagct ggatctgatc gagcagctca gccaggtggg caagcccttg   1620
gtcgtcctgc agatgggcgg tggccaggtg gattcgtcgt cactcaaggc caacaagaat   1680
gtcaacgctc tggtgtgggg tggctatccc ggacagtcgg gtggtgcggc cctgtttgac   1740
atccttacgg gcaagcgtgc gccggccggt cgtctggtga gcacgcagta cccggccgag   1800
tatgcgacgc agttcccggc caacgacatg aacctgcgtc cgaacggcag caacccggga   1860
cagacataca tctggtacac gggcacgccc gtgtatgagt tcggccacgg tctgttctac   1920
acggagttcc aggagtcggc tgcggcgggc acgaacaaga cgtcgacttt cgacattctg   1980
gaccttttct ccacccctca tccgggatac gagtacatcg agcaggttcc gttcatcaac   2040
gtgactgtga cgtgaagaa cgtcggccac acgccatcgc cgtacacggg tctgttgttc   2100
gcgaacacga cagccgggcc caagccgtac ccgaacaaat ggctcgtcgg gttcgactgg   2160
ctgccgacga tccagccggg cgagactgcc aagttgacga tcccggtgcc gttgggcgcg   2220
attgcgtggg cggacgagaa cggcaacaag gtggtcttcc cgggcaacta cgaattggca   2280
ctgaacaatg agcgatcggt agtggtgtcg ttcacgctga cgggcgatgc ggcgactcta   2340
gagaaatggc ctttgtggga gcaggcggtt ccggggggtgc tgcagcaata a            2391
```

<210> SEQ ID NO 12
<211> LENGTH: 796
<212> TYPE: PRT
<213> ORGANISM: Talaromyces emersonii

<400> SEQUENCE: 12

Met Met Thr Pro Thr Ala Ile Leu Thr Ala Val Ala Ala Leu Leu Pro
1               5                   10                  15

Thr Ala Thr Trp Ala Gln Asp Asn Gln Thr Tyr Ala Asn Tyr Ser Ser
            20                  25                  30

Gln Ser Gln Pro Asp Leu Phe Pro Arg Thr Val Ala Thr Ile Asp Leu
            35                  40                  45

Ser Phe Pro Asp Cys Glu Asn Gly Pro Leu Ser Thr Asn Leu Val Cys
 50                  55                  60

Asn Lys Ser Ala Asp Pro Trp Ala Arg Ala Glu Ala Leu Ile Ser Leu
 65                  70                  75                  80

Phe Thr Leu Glu Glu Leu Ile Asn Asn Thr Gln Asn Thr Ala Pro Gly
                85                  90                  95

Val Pro Arg Leu Gly Leu Pro Gln Tyr Gln Val Trp Asn Glu Ala Leu
            100                 105                 110

His Gly Leu Asp Arg Ala Asn Phe Ser His Ser Gly Glu Tyr Ser Trp
        115                 120                 125

Ala Thr Ser Phe Pro Met Pro Ile Leu Ser Met Ala Ser Phe Asn Arg
130                 135                 140

Thr Leu Ile Asn Gln Ile Ala Ser Ile Ile Ala Thr Gln Ala Arg Ala
145                 150                 155                 160

Phe Asn Asn Ala Gly Arg Tyr Gly Leu Asp Ser Tyr Ala Pro Asn Ile
                165                 170                 175

Asn Gly Phe Arg Ser Pro Leu Trp Gly Arg Gly Gln Glu Thr Pro Gly
            180                 185                 190

Glu Asp Ala Phe Phe Leu Ser Ser Thr Tyr Ala Tyr Glu Tyr Ile Thr
        195                 200                 205

Gly Leu Gln Gly Gly Val Asp Pro Glu His Val Lys Ile Val Ala Thr
    210                 215                 220

Ala Lys His Phe Ala Gly Tyr Asp Leu Glu Asn Trp Gly Asn Val Ser
225                 230                 235                 240

Arg Leu Gly Phe Asn Ala Ile Ile Thr Gln Gln Asp Leu Ser Glu Tyr
                245                 250                 255

Tyr Thr Pro Gln Phe Leu Ala Ser Ala Arg Tyr Ala Lys Thr Arg Ser
            260                 265                 270

Ile Met Cys Ser Tyr Asn Ala Val Asn Gly Val Pro Ser Cys Ala Asn
        275                 280                 285

Ser Phe Phe Leu Gln Thr Leu Leu Arg Glu Asn Phe Asp Phe Val Asp
290                 295                 300

Asp Gly Tyr Val Ser Ser Asp Cys Asp Ala Val Tyr Asn Val Phe Asn
305                 310                 315                 320

Pro His Gly Tyr Ala Leu Asn Gln Ser Gly Ala Ala Ala Asp Ser Leu
                325                 330                 335

Leu Ala Gly Thr Asp Ile Asp Cys Gly Gln Thr Leu Pro Trp His Leu
            340                 345                 350

Asn Glu Ser Phe Val Glu Gly Tyr Val Ser Arg Gly Asp Ile Glu Lys
        355                 360                 365

Ser Leu Thr Arg Leu Tyr Ser Asn Leu Val Arg Leu Gly Tyr Phe Asp
    370                 375                 380

Gly Asn Asn Ser Glu Tyr Arg Asn Leu Asn Trp Asn Asp Val Val Thr
385                 390                 395                 400

Thr Asp Ala Trp Asn Ile Ser Tyr Glu Ala Ala Val Glu Gly Ile Thr
                405                 410                 415

Leu Leu Lys Asn Asp Gly Thr Leu Pro Leu Ser Lys Lys Val Arg Ser
            420                 425                 430

Ile Ala Leu Ile Gly Pro Trp Ala Asn Ala Thr Val Gln Met Gln Gly
        435                 440                 445

Asn Tyr Tyr Gly Thr Pro Pro Tyr Leu Ile Ser Pro Leu Glu Ala Ala

```
                    450                 455                 460
Lys Ala Ser Gly Phe Thr Val Asn Tyr Ala Phe Gly Thr Asn Ile Ser
465                 470                 475                 480

Thr Asp Ser Thr Gln Trp Phe Ala Glu Ala Ile Ala Ala Ala Lys Lys
                485                 490                 495

Ser Asp Val Ile Ile Tyr Ala Gly Gly Ile Asp Asn Thr Ile Glu Ala
                500                 505                 510

Glu Gly Gln Asp Arg Thr Asp Leu Lys Trp Pro Gly Asn Gln Leu Asp
            515                 520                 525

Leu Ile Glu Gln Leu Ser Gln Val Gly Lys Pro Leu Val Val Leu Gln
530                 535                 540

Met Gly Gly Gly Gln Val Asp Ser Ser Ser Leu Lys Ala Asn Lys Asn
545                 550                 555                 560

Val Asn Ala Leu Val Trp Gly Gly Tyr Pro Gly Gln Ser Gly Gly Ala
                565                 570                 575

Ala Leu Phe Asp Ile Leu Thr Gly Lys Arg Ala Pro Ala Gly Arg Leu
                580                 585                 590

Val Ser Thr Gln Tyr Pro Ala Glu Tyr Ala Thr Gln Phe Pro Ala Asn
            595                 600                 605

Asp Met Asn Leu Arg Pro Asn Gly Ser Asn Pro Gly Gln Thr Tyr Ile
610                 615                 620

Trp Tyr Thr Gly Thr Pro Val Tyr Glu Phe Gly His Gly Leu Phe Tyr
625                 630                 635                 640

Thr Glu Phe Gln Glu Ser Ala Ala Ala Gly Thr Asn Lys Thr Ser Thr
                645                 650                 655

Phe Asp Ile Leu Asp Leu Phe Ser Thr Pro His Pro Gly Tyr Glu Tyr
                660                 665                 670

Ile Glu Gln Val Pro Phe Ile Asn Val Thr Val Asp Val Lys Asn Val
            675                 680                 685

Gly His Thr Pro Ser Pro Tyr Thr Gly Leu Leu Phe Ala Asn Thr Thr
690                 695                 700

Ala Gly Pro Lys Pro Tyr Pro Asn Lys Trp Leu Val Gly Phe Asp Trp
705                 710                 715                 720

Leu Pro Thr Ile Gln Pro Gly Glu Thr Ala Lys Leu Thr Ile Pro Val
                725                 730                 735

Pro Leu Gly Ala Ile Ala Trp Ala Asp Glu Asn Gly Asn Lys Val Val
                740                 745                 750

Phe Pro Gly Asn Tyr Glu Leu Ala Leu Asn Asn Glu Arg Ser Val Val
            755                 760                 765

Val Ser Phe Thr Leu Thr Gly Asp Ala Ala Thr Leu Glu Lys Trp Pro
770                 775                 780

Leu Trp Glu Gln Ala Val Pro Gly Val Leu Gln Gln
785                 790                 795

<210> SEQ ID NO 13
<211> LENGTH: 1507
<212> TYPE: DNA
<213> ORGANISM: Trichoderma reesei

<400> SEQUENCE: 13
atggcgccct cagttacact gccgttgacc acggccatcc tggccattgc ccggctcgtc      60
gccgcccagc aaccgggtac cagcaccccc gaggtccatc ccaagttgac aacctacaag     120
tgtacaaagt ccgggggggtg cgtggcccag gacacctcgg tggtccttga ctggaactac     180
```

```
cgctggatgc acgacgcaaa ctacaactcg tgcaccgtca acggcggcgt caacaccacg    240
ctctgccctg acgaggcgac ctgtggcaag aactgcttca tcgagggcgt cgactacgcc    300
gcctcgggcg tcacgacctc gggcagcagc ctcaccatga accagtacat gcccagcagc    360
tctggcggct acagcagcgt ctctcctcgg ctgtatctcc tggactctga cggtgagtac    420
gtgatgctga agctcaacgg ccaggagctg agcttcgacg tcgacctctc tgctctgccg    480
tgtggagaga acggctcgct ctacctgtct cagatggacg agaacggggg cgccaaccag    540
tataacacgg ccggtgccaa ctacgggagc ggctactgcg atgctcagtg ccccgtccag    600
acatggagga acggcaccct caacactagc caccagggct tctgctgcaa cgagatggat    660
atcctggagg gcaactcgag ggcgaatgcc ttgacccctc actcttgcac ggccacggcc    720
tgcgactctg ccggttgcgg cttcaacccc tatggcagcg gctacaaaag gtgagcctga    780
tgccactact accccttcc tggcgctctc gcggttttcc atgctgacat ggttttccag    840
ctactacggc cccggagata ccgttgacac ctccaagacc ttcaccatca tcacccagtt    900
caacacggac aacggctcgc cctcgggcaa ccttgtgagc atcacccgca agtaccagca    960
aaacggcgtc gacatcccca gcgcccagcc cggcggcgac accatctcgt cctgccccgtc   1020 cgcctcagcc tacggcggcc tcgccaccat gggcaaggcc ctgagcagcg gcatggtgct   1080
cgtgttcagc atttggaacg acaacagcca gtacatgaac tggctcgaca gcggcaacgc   1140
cggcccctgc agcagcaccg agggcaaccc atccaacatc ctggccaaca ccccaacac   1200 gcacgtcgtc ttctccaaca tccgctgggg agacattggg tctactacga actcgactgc   1260 gccccgccc ccgcctgcgt ccagcacgac gttttcgact acacggagga gctcgacgac   1320
ttcgagcagc ccgagctgca cgcagactca ctggggcag tgcggtggca ttgggtacag   1380
cgggtgcaag acgtgcacgt cgggcactac gtgccagtat agcaacgact gttcgtatcc   1440
ccatgcctga cgggagtgat tttgagatgc taaccgctaa aatacagact actcgcaatg   1500
cctttag                                                              1507
```

<210> SEQ ID NO 14
<211> LENGTH: 459
<212> TYPE: PRT
<213> ORGANISM: Trichoderma reesei

<400> SEQUENCE: 14

Met Ala Pro Ser Val Thr Leu Pro Leu Thr Thr Ala Ile Leu Ala Ile
1               5                   10                  15

Ala Arg Leu Val Ala Ala Gln Gln Pro Gly Thr Ser Thr Pro Glu Val
                20                  25                  30

His Pro Lys Leu Thr Thr Tyr Lys Cys Thr Lys Ser Gly Gly Cys Val
            35                  40                  45

Ala Gln Asp Thr Ser Val Val Leu Asp Trp Asn Tyr Arg Trp Met His
        50                  55                  60

Asp Ala Asn Tyr Asn Ser Cys Thr Val Asn Gly Gly Val Asn Thr Thr
65                  70                  75                  80

Leu Cys Pro Asp Glu Ala Thr Cys Gly Lys Asn Cys Phe Ile Glu Gly
                85                  90                  95

Val Asp Tyr Ala Ala Ser Gly Val Thr Thr Ser Gly Ser Ser Leu Thr
            100                 105                 110

Met Asn Gln Tyr Met Pro Ser Ser Gly Gly Tyr Ser Ser Val Ser
        115                 120                 125

Pro Arg Leu Tyr Leu Leu Asp Ser Asp Gly Glu Tyr Val Met Leu Lys

```
                130             135             140
Leu Asn Gly Gln Glu Leu Ser Phe Asp Val Asp Leu Ser Ala Leu Pro
145                 150                 155                 160

Cys Gly Glu Asn Gly Ser Leu Tyr Leu Ser Gln Met Asp Glu Asn Gly
                165                 170                 175

Gly Ala Asn Gln Tyr Asn Thr Ala Gly Ala Asn Tyr Gly Ser Gly Tyr
                180                 185                 190

Cys Asp Ala Gln Cys Pro Val Gln Thr Trp Arg Asn Gly Thr Leu Asn
                195                 200                 205

Thr Ser His Gln Gly Phe Cys Cys Asn Glu Met Asp Ile Leu Glu Gly
                210                 215                 220

Asn Ser Arg Ala Asn Ala Leu Thr Pro His Ser Cys Thr Ala Thr Ala
225                 230                 235                 240

Cys Asp Ser Ala Gly Cys Gly Phe Asn Pro Tyr Gly Ser Gly Tyr Lys
                245                 250                 255

Ser Tyr Tyr Gly Pro Gly Asp Thr Val Asp Thr Ser Lys Thr Phe Thr
                260                 265                 270

Ile Ile Thr Gln Phe Asn Thr Asp Asn Gly Ser Pro Ser Gly Asn Leu
                275                 280                 285

Val Ser Ile Thr Arg Lys Tyr Gln Gln Asn Gly Val Asp Ile Pro Ser
290                 295                 300

Ala Gln Pro Gly Gly Asp Thr Ile Ser Ser Cys Pro Ser Ala Ser Ala
305                 310                 315                 320

Tyr Gly Gly Leu Ala Thr Met Gly Lys Ala Leu Ser Ser Gly Met Val
                325                 330                 335

Leu Val Phe Ser Ile Trp Asn Asp Asn Ser Gln Tyr Met Asn Trp Leu
                340                 345                 350

Asp Ser Gly Asn Ala Gly Pro Cys Ser Ser Thr Glu Gly Asn Pro Ser
                355                 360                 365

Asn Ile Leu Ala Asn Asn Pro Asn Thr His Val Val Phe Ser Asn Ile
370                 375                 380

Arg Trp Gly Asp Ile Gly Ser Thr Thr Asn Ser Thr Ala Pro Pro Pro
385                 390                 395                 400

Pro Pro Ala Ser Ser Thr Thr Phe Ser Thr Thr Arg Arg Ser Ser Thr
                405                 410                 415

Thr Ser Ser Ser Pro Ser Cys Thr Gln Thr His Trp Gly Gln Cys Gly
                420                 425                 430

Gly Ile Gly Tyr Ser Gly Cys Lys Thr Cys Thr Ser Gly Thr Thr Cys
                435                 440                 445

Gln Tyr Ser Asn Asp Tyr Tyr Ser Gln Cys Leu
450                 455
```

<210> SEQ ID NO 15
<211> LENGTH: 1507
<212> TYPE: DNA
<213> ORGANISM: Trichoderma reesei

<400> SEQUENCE: 15

```
atggcgccct cagttacact gccgttgacc acggccatcc tggccattgc ccggctcgtc    60
gccgcccagc aaccgggtac cagcaccccc gaggtccatc ccaagttgac aacctacaag   120
tgtacaaagt ccgggggggtg cgtggcccag gacacctcgg tggtccttga ctggaactac   180
cgctggatgc acgacgcaaa ctacaactcg tgcaccgtca acggcggcgt caacaccacg   240
ctctgccctg acgaggcgac tgtggcaag aactgcttca tcgagggcgt cgactacgcc   300
```

```
gcctcgggcg tcacgacctc gggcagcagc ctcaccatga accagtacat gcccagcagc    360
tctggcggct acagcagcgt ctctcctcgg ctgtatctcc tggactctga cggtgagtac    420
gtgatgctga agctcaacgg ccaggagctg agcttcgacg tcgacctctc tgctctgccg    480
tgtggagaga acggctcgct ctacctgtct cagatggacg agaacggggg cgccaaccag    540
tataacacgg ccggtgccaa ctacgggagc ggctactgcg atgctcagtg ccccgtccag    600
acatggagga acggcaccct caacactagc caccagggct tctgctgcaa cgagatggat    660
atcctggagg gcaactcgag ggcgaatgcc ttgaccccctc actcttgcac ggccacggcc    720
tgcgactctg ccgttgcgg cttcaacccc tatggcagcg gctacaaaag gtgagcctga    780
tgccactact acccctttcc tggcgctctc gcggttttcc atgctgacat ggttttccag    840
ctactacggc cccggagata ccgttgacac ctccaagacc ttcaccatca tcacccagtt    900
caacacggac aacggctcgc cctcgggcaa ccttgtgagc atcacccgca agtaccagca    960
aaacggcgtc gacatcccca cgcgcccagcc cggcggcgac accatctcgt cctgcccgtc    1020
cgcctcagcc tacggcggcc tcgccaccat gggcaaggcc ctgagcagcg gcatggtgct    1080
cgtgttcagc atttggaacg acaacagcca gtacatgaac tggctcgaca gcggcaacgc    1140
cggcccctgc agcagcaccg agggcaaccc atccaacatc ctggccaaca ccccaacac    1200 gcacgtcgtc ttctccaaca tccgctgggg agacattggg tctactacga actcgactgc    1260 gccccgccc cgcctgcgt ccagcacgac gttttcgact acacggagga gctcgacgac    1320
ttcgagcagc ccgagctgca cgcagactca ctggggcag tgcggtggca ttgggtacag    1380
cgggtgcaag acgtgcacgt cgggcactac gtgccagtat agcaacgact gttcgtatcc    1440
ccatgcctga cgggagtgat tttgagatgc taaccgctaa aatacagact actcgcaatg    1500
cctttag                                                              1507
```

<210> SEQ ID NO 16
<211> LENGTH: 418
<212> TYPE: PRT
<213> ORGANISM: Trichoderma reesei

<400> SEQUENCE: 16

```
Met Asn Lys Ser Val Ala Pro Leu Leu Ala Ala Ser Ile Leu Tyr
1               5                   10                  15

Gly Gly Ala Ala Ala Gln Gln Thr Val Trp Gly Gln Cys Gly Gly Ile
                20                  25                  30

Gly Trp Ser Gly Pro Thr Asn Cys Ala Pro Gly Ser Ala Cys Ser Thr
            35                  40                  45

Leu Asn Pro Tyr Tyr Ala Gln Cys Ile Pro Gly Ala Thr Thr Ile Thr
        50                  55                  60

Thr Ser Thr Arg Pro Pro Ser Gly Pro Thr Thr Thr Arg Ala Thr
65                  70                  75                  80

Ser Thr Ser Ser Ser Thr Pro Pro Thr Ser Ser Gly Val Arg Phe Ala
                85                  90                  95

Gly Val Asn Ile Ala Gly Phe Asp Phe Gly Cys Thr Thr Asp Gly Thr
            100                 105                 110

Cys Val Thr Ser Lys Val Tyr Pro Pro Leu Lys Asn Phe Thr Gly Ser
        115                 120                 125

Asn Asn Tyr Pro Asp Gly Ile Gly Gln Met Gln His Phe Val Asn Asp
    130                 135                 140

Asp Gly Met Thr Ile Phe Arg Leu Pro Val Gly Trp Gln Tyr Leu Val
```

```
                145                 150                 155                 160
Asn Asn Asn Leu Gly Gly Asn Leu Asp Ser Thr Ser Ile Ser Lys Tyr
                165                 170                 175
Asp Gln Leu Val Gln Gly Cys Leu Ser Leu Gly Ala Tyr Cys Ile Val
                180                 185                 190
Asp Ile His Asn Tyr Ala Arg Trp Asn Gly Ile Ile Gly Gln Gly
            195                 200                 205
Gly Pro Thr Asn Ala Gln Phe Thr Ser Leu Trp Ser Gln Leu Ala Ser
            210                 215                 220
Lys Tyr Ala Ser Gln Ser Arg Val Trp Phe Gly Ile Met Asn Glu Pro
225                 230                 235                 240
His Asp Val Asn Ile Asn Thr Trp Ala Ala Thr Val Gln Glu Val Val
                245                 250                 255
Thr Ala Ile Arg Asn Ala Gly Ala Thr Ser Gln Phe Ile Ser Leu Pro
                260                 265                 270
Gly Asn Asp Trp Gln Ser Ala Gly Ala Phe Ile Ser Asp Gly Ser Ala
                275                 280                 285
Ala Ala Leu Ser Gln Val Thr Asn Pro Asp Gly Ser Thr Thr Asn Leu
            290                 295                 300
Ile Phe Asp Val His Lys Tyr Leu Asp Ser Asp Asn Ser Gly Thr His
305                 310                 315                 320
Ala Glu Cys Thr Thr Asn Asn Ile Asp Gly Ala Phe Ser Pro Leu Ala
                325                 330                 335
Thr Trp Leu Arg Gln Asn Asn Arg Gln Ala Ile Leu Thr Glu Thr Gly
                340                 345                 350
Gly Gly Asn Val Gln Ser Cys Ile Gln Asp Met Cys Gln Gln Ile Gln
            355                 360                 365
Tyr Leu Asn Gln Asn Ser Asp Val Tyr Leu Gly Tyr Val Gly Trp Gly
            370                 375                 380
Ala Gly Ser Phe Asp Ser Thr Tyr Val Leu Thr Glu Thr Pro Thr Gly
385                 390                 395                 400
Ser Gly Asn Ser Trp Thr Asp Thr Ser Leu Val Ser Ser Cys Leu Ala
                405                 410                 415
Arg Lys

<210> SEQ ID NO 17
<211> LENGTH: 3060
<212> TYPE: DNA
<213> ORGANISM: Aspergillus fumigatus

<400> SEQUENCE: 17
atgagattcg gttggctcga ggtggccgct ctgacggccg cttctgtagc caatgcccag      60
gtttgtgatg ctttcccgtc attgtttcgg atatagttga caatagtcat ggaaataatc     120
aggaattggc tttctctcca ccattctacc cttcgccttg gctgatggc agggagagt      180 gggcagatgc ccatcgacgc gccgtcgaga tcgtttctca gatgacactg gcggagaagg    240
ttaaccttac aacgggtact gggtgggttg cgactttttt gttgacagtg agctttcttc     300
actgaccatc tacacagatg gaaatggac cgatgcgtcg tcaaaccgg cagcgttccc      360 aggtaagctt gcaattctgc aacaacgtgc aagtgtagtt gctaaaacgc ggtggtgcag    420
acttggtatc aactgggtc tttgtggcca ggattcccct ttgggtatcc gtgactgtga     480
gctatacccg cggagtcttt cagtccttgt attatgtgct gatgattgtc tctgtatagc     540
tgacctcaac tccgccttcc ctgctggtac taatgtcgcc gcgacatggg acaagacact    600
```

```
cgcctacctt cgtggcaagg ccatgggtga ggaattcaac gacaagggcg tggacatttt     660
gctggggcct gctgctggtc ctctcggcaa atacccggac ggcggcagaa tctgggaagg     720
cttctctcct gatccggttc tcactggtgt acttttcgcc gaaactatca agggtatcca     780
agacgcgggt gtgattgcta ctgccaagca ttacattctg aatgaacagg agcatttccg     840
acaggttggc gaggcccagg gatatggtta caacatcacg gagacgatca gctccaacgt     900
ggatgacaag accatgcacg agttgtacct ttggtgagta gttgacactg caaatgagga     960
ccttgattga tttgactgac ctggaatgca ggcccttttgc agatgctgtg cgcggtaaga    1020 tttttccgtag acttgacctc gcgacgaaga aatcgctgac gaaccatcgt agctggcgtt    1080
ggcgctgtca tgtgttccta caatcaaatc aacaacagct acggttgtca aaacagtcaa    1140
actctcaaca agctcctcaa ggctgagctg ggcttccaag gcttcgtcat gagtgactgg    1200
ggcgctcacc acagcggtgt cggcgctgcc ctcgctgggt tggatatgtc gatgcctgga    1260
gacatttcct tcgacgacgg actctccttc tggggcacga acctaactgt cagtgttctt    1320
aacggcaccg ttccagcctg gcgtgtcgat gacatggctg ttcgtatcat gaccgcgtac    1380
tacaaggttg gtcgtgaccg tcttcgtatt ccccctaact tcagctcctg gacccgggat    1440
gagtacggct gggagcattc tgctgtctcc gagggagcct ggaccaaggt gaacgacttc    1500
gtcaatgtgc agcgcagtca ctctcagatc atccgtgaga ttggtgccgc tagtacagtg    1560
ctcttgaaga acacgggtgc tcttcctttg accggcaagg aggttaaagt gggtgttctc    1620
ggtgaagacg ctggttccaa cccgtggggt gctaacggct gccccgaccg cggctgtgat    1680
aacggcactc ttgctatggc ctggggtagt ggtactgccg agttcccta ccttgtcacc     1740 cccgagcagg ctatccagcg agaggtcatc agcaacggcg gcaatgtctt tgctgtgact    1800
gataacgggg ctctcagcca gatggcagat gttgcatctc aatccaggtg agtgcgggct    1860
cttagaaaaa gaacgttctc tgaatgaagt tttttaacca ttgcgaacag cgtgtctttg    1920
gtgtttgtca acgccgactc tggagagggt tacatcagtg tcgacggcaa cgagggtgac    1980
cgcaaaaatc tcactctgtg gaagaacggc gaggccgtca ttgacactgt tgtcagccac    2040
tgcaacaaca cgattgtggt tattcacagt gttgggcccg tcttgatcga ccggtggtat    2100
gataacccca acgtcactgc catcatctgg gccggcttgc ccggtcagga gagtggcaac    2160
tccctggtcg acgtgctcta tggccgcgtc aaccccagcg ccaagacccc gttcacctgg    2220
ggcaagactc gggagtctta cggggctccc ttgctcaccg agcctaacaa tggcaatggt    2280
gctccccagg atgatttcaa cgagggcgtc ttcattgact accgtcactt tgacaagcgc    2340
aatgagaccc ccatttatga gtttggccat ggcttgagct acaccacctt tggttactct    2400
caccttcggg ttcaggccct caatagttcg agttcggcat atgtcccgac tagcggagag    2460
accaagcctg cgccaaccta tggtgagatc ggtagtgccg ccgactacct gtatcccgag    2520
ggtctcaaaa gaattaccaa gtttatttac ccttggctca actcgaccga cctcgaggat    2580
tcttctgacg acccgaacta cggctgggag gactcggagt acattcccga aggcgctagg    2640
gatgggtctc ctcaacccct cctgaaggct ggcggcgctc ctggtggtaa ccctaccctt    2700
tatcaggatc ttgttagggt gtcggccacc ataaccaaca ctggtaacgt cgccggttat    2760
gaagtccctc aattggtgag tgacccgcat gttccttgcg ttgcaatttg gctaactcgc    2820
ttctagtatg tttcactggg cggaccgaac gagcctcggg tcgttctgcg caagttcgac    2880
cgaatcttcc tggctcctgg ggagcaaaag gtttggacca cgactcttaa ccgtcgtgat    2940
```
ctcgccaatt gggatgtgga ggctcaggac tgggtcatca caaagtaccc caagaaagtg   3000
cacgtcggca gctcctcgcg taagctgcct ctgagagcgc ctctgccccg tgtctactag   3060

<210> SEQ ID NO 18
<211> LENGTH: 863
<212> TYPE: PRT
<213> ORGANISM: Aspergillus fumigatus

<400> SEQUENCE: 18

Met Arg Phe Gly Trp Leu Glu Val Ala Ala Leu Thr Ala Ala Ser Val
1               5                   10                  15

Ala Asn Ala Gln Glu Leu Ala Phe Ser Pro Pro Phe Tyr Pro Ser Pro
            20                  25                  30

Trp Ala Asp Gly Gln Gly Glu Trp Ala Asp Ala His Arg Arg Ala Val
        35                  40                  45

Glu Ile Val Ser Gln Met Thr Leu Ala Glu Lys Val Asn Leu Thr Thr
    50                  55                  60

Gly Thr Gly Trp Glu Met Asp Arg Cys Val Gln Thr Gly Ser Val
65                  70                  75                  80

Pro Arg Leu Gly Ile Asn Trp Gly Leu Cys Gly Gln Asp Ser Pro Leu
                85                  90                  95

Gly Ile Arg Asp Ser Asp Leu Asn Ser Ala Phe Pro Ala Gly Thr Asn
            100                 105                 110

Val Ala Ala Thr Trp Asp Lys Thr Leu Ala Tyr Leu Arg Gly Lys Ala
        115                 120                 125

Met Gly Glu Glu Phe Asn Asp Lys Gly Val Asp Ile Leu Leu Gly Pro
    130                 135                 140

Ala Ala Gly Pro Leu Gly Lys Tyr Pro Asp Gly Gly Arg Ile Trp Glu
145                 150                 155                 160

Gly Phe Ser Pro Asp Pro Val Leu Thr Gly Val Leu Phe Ala Glu Thr
                165                 170                 175

Ile Lys Gly Ile Gln Asp Ala Gly Val Ile Ala Thr Ala Lys His Tyr
            180                 185                 190

Ile Leu Asn Glu Gln Glu His Phe Arg Gln Val Gly Glu Ala Gln Gly
        195                 200                 205

Tyr Gly Tyr Asn Ile Thr Glu Thr Ile Ser Ser Asn Val Asp Asp Lys
    210                 215                 220

Thr Met His Glu Leu Tyr Leu Trp Pro Phe Ala Asp Ala Val Arg Ala
225                 230                 235                 240

Gly Val Gly Ala Val Met Cys Ser Tyr Asn Gln Ile Asn Asn Ser Tyr
                245                 250                 255

Gly Cys Gln Asn Ser Gln Thr Leu Asn Lys Leu Leu Lys Ala Glu Leu
            260                 265                 270

Gly Phe Gln Gly Phe Val Met Ser Asp Trp Gly Ala His His Ser Gly
        275                 280                 285

Val Gly Ala Ala Leu Ala Gly Leu Asp Met Ser Met Pro Gly Asp Ile
    290                 295                 300

Ser Phe Asp Asp Gly Leu Ser Phe Trp Gly Thr Asn Leu Thr Val Ser
305                 310                 315                 320

Val Leu Asn Gly Thr Val Pro Ala Trp Arg Val Asp Asp Met Ala Val
                325                 330                 335

Arg Ile Met Thr Ala Tyr Tyr Lys Val Gly Arg Asp Arg Leu Arg Ile
            340                 345                 350

Pro Pro Asn Phe Ser Ser Trp Thr Arg Asp Glu Tyr Gly Trp Glu His

-continued

```
            355                 360                 365
Ser Ala Ser Glu Gly Ala Trp Thr Lys Val Asn Asp Phe Val Asn
    370                 375                 380
Val Gln Arg Ser His Ser Gln Ile Ile Arg Glu Ile Gly Ala Ala Ser
385                 390                 395                 400
Thr Val Leu Leu Lys Asn Thr Gly Ala Leu Pro Leu Thr Gly Lys Glu
                405                 410                 415
Val Lys Val Gly Val Leu Gly Glu Asp Ala Gly Ser Asn Pro Trp Gly
                420                 425                 430
Ala Asn Gly Cys Pro Asp Arg Gly Cys Asp Asn Gly Thr Leu Ala Met
                435                 440                 445
Ala Trp Gly Ser Gly Thr Ala Glu Phe Pro Tyr Leu Val Thr Pro Glu
            450                 455                 460
Gln Ala Ile Gln Arg Glu Val Ile Ser Asn Gly Gly Asn Val Phe Ala
465                 470                 475                 480
Val Thr Asp Asn Gly Ala Leu Ser Gln Met Ala Asp Val Ala Ser Gln
                485                 490                 495
Ser Ser Val Ser Leu Val Phe Val Asn Ala Asp Ser Gly Glu Gly Tyr
                500                 505                 510
Ile Ser Val Asp Gly Asn Glu Gly Asp Arg Lys Asn Leu Thr Leu Trp
                515                 520                 525
Lys Asn Gly Glu Ala Val Ile Asp Thr Val Val Ser His Cys Asn Asn
530                 535                 540
Thr Ile Val Val Ile His Ser Val Gly Pro Val Leu Ile Asp Arg Trp
545                 550                 555                 560
Tyr Asp Asn Pro Asn Val Thr Ala Ile Ile Trp Ala Gly Leu Pro Gly
                565                 570                 575
Gln Glu Ser Gly Asn Ser Leu Val Asp Val Leu Tyr Gly Arg Val Asn
                580                 585                 590
Pro Ser Ala Lys Thr Pro Phe Thr Trp Gly Lys Thr Arg Glu Ser Tyr
                595                 600                 605
Gly Ala Pro Leu Leu Thr Glu Pro Asn Asn Gly Asn Gly Ala Pro Gln
            610                 615                 620
Asp Asp Phe Asn Glu Gly Val Phe Ile Asp Tyr Arg His Phe Asp Lys
625                 630                 635                 640
Arg Asn Glu Thr Pro Ile Tyr Glu Phe Gly His Gly Leu Ser Tyr Thr
                645                 650                 655
Thr Phe Gly Tyr Ser His Leu Arg Val Gln Ala Leu Asn Ser Ser Ser
                660                 665                 670
Ser Ala Tyr Val Pro Thr Ser Gly Glu Thr Lys Pro Ala Pro Thr Tyr
                675                 680                 685
Gly Glu Ile Gly Ser Ala Ala Asp Tyr Leu Tyr Pro Glu Gly Leu Lys
            690                 695                 700
Arg Ile Thr Lys Phe Ile Tyr Pro Trp Leu Asn Ser Thr Asp Leu Glu
705                 710                 715                 720
Asp Ser Ser Asp Asp Pro Asn Tyr Gly Trp Glu Asp Ser Glu Tyr Ile
                725                 730                 735
Pro Glu Gly Ala Arg Asp Gly Ser Pro Gln Pro Leu Leu Lys Ala Gly
                740                 745                 750
Gly Ala Pro Gly Gly Asn Pro Thr Leu Tyr Gln Asp Leu Val Arg Val
            755                 760                 765
Ser Ala Thr Ile Thr Asn Thr Gly Asn Val Ala Gly Tyr Glu Val Pro
770                 775                 780
```

Gln Leu Tyr Val Ser Leu Gly Gly Pro Asn Glu Pro Arg Val Val Leu
785                 790                 795                 800

Arg Lys Phe Asp Arg Ile Phe Leu Ala Pro Gly Glu Gln Lys Val Trp
            805                 810                 815

Thr Thr Thr Leu Asn Arg Arg Asp Leu Ala Asn Trp Asp Val Glu Ala
        820                 825                 830

Gln Asp Trp Val Ile Thr Lys Tyr Pro Lys Lys Val His Val Gly Ser
    835                 840                 845

Ser Ser Arg Lys Leu Pro Leu Arg Ala Pro Leu Pro Arg Val Tyr
850                 855                 860

<210> SEQ ID NO 19
<211> LENGTH: 1415
<212> TYPE: DNA
<213> ORGANISM: Aspergillus fumigatus

<400> SEQUENCE: 19

```
atggtccatc tatcttcatt ggcagcagcc ctggctgctc tgcctctgta tgtttaccca        60
ctcacgagag gaggaacagc tttgacattg ctatagtgta tatggagctg cctgaacac        120 agcagccaaa gccaaaggac taaagtactt tggttccgcc acggacaatc agagctcac        180 ggactctgcg tatgtcgcgc aactgagcaa caccgatgat tttggtcaaa tcacacccgg        240
aaactccatg aaggtttgct acgtctgcct ccctggagc attgcctcaa agctaattg         300 gttgttttgt ttggatagtg ggatgccacc gagccttctc agaattcttt ttcgttcgca        360
aatggagacg ccgtggtcaa tctggcgaac aagaatggcc agctgatgcg atgccatact       420
ctggtctggc acagtcagct accgaactgg ggtatgtaaa cgtcttgtct attctcaaat       480
actctctaac agttgacagt ctctagcggg tcatggacca atgcgaccct tttggcggcc      540
atgaagaatc atatcaccaa tgtggttact cactacaagg ggaagtgcta cgcctgggat      600
gttgtcaatg aaggtttgtt gctccatcta tcctcaatag ttcttttgaa actgacaagc      660
ctgtcaatct agccctgaac gaggacggta ctttccgtaa ctctgtcttc taccagatca      720
tcggcccagc atacattcct attgcgttcg ccacggctgc tgccgcagat ccgacgtga       780 aactctacta caacgactac aacattgaat actcaggcgc caaagcgact gctgcgcaga      840
atatcgtcaa gatgatcaag gcctacgcg cgaagatcga cggcgtcggc tccaggcac       900 actttatcgt cggcagcact ccgagtcaat cggatctgac gaccgtcttg aagggctaca      960
ctgctctcgg cgttgaggtg gcctatacccg aacttgacat ccgcatgcag ctgccctcga     1020
ccgccgcaaa gctggcccag cagtccactg acttccaagg cgtggccgca gcatgcgtta     1080
gcaccactgg ctgcgtgggt gtcactatct gggactggac cgacaagtac tcctgggtcc     1140
ccagcgtgtt ccaaggctac ggcgccccat gccttggga tgagaactat gtgaagaagc     1200
cagcgtacga tggcctgatg gcgggtcttg gagcaagcgg ctccggcacc acaacgacca    1260
ctactactac ttctactacg acaggaggta cggaccctac tggagtcgct cagaaatggg    1320
gacagtgtgg cggtattggc tggaccgggc caacaacttg tgtcagtggt accacttgcc    1380
aaaagctgaa tgactggtac tcacagtgcc tgtaa                                1415
```

<210> SEQ ID NO 20
<211> LENGTH: 397
<212> TYPE: PRT
<213> ORGANISM: Aspergillus fumigatus

<400> SEQUENCE: 20

```
Met Val His Leu Ser Ser Leu Ala Ala Leu Ala Ala Leu Pro Leu
1               5                   10                  15

Val Tyr Gly Ala Gly Leu Asn Thr Ala Ala Lys Ala Lys Gly Leu Lys
            20                  25                  30

Tyr Phe Gly Ser Ala Thr Asp Asn Pro Glu Leu Thr Asp Ser Ala Tyr
        35                  40                  45

Val Ala Gln Leu Ser Asn Thr Asp Asp Phe Gly Gln Ile Thr Pro Gly
50                  55                  60

Asn Ser Met Lys Trp Asp Ala Thr Glu Pro Ser Gln Asn Ser Phe Ser
65                  70                  75                  80

Phe Ala Asn Gly Asp Ala Val Val Asn Leu Ala Asn Lys Asn Gly Gln
                85                  90                  95

Leu Met Arg Cys His Thr Leu Val Trp His Ser Gln Leu Pro Asn Trp
            100                 105                 110

Val Ser Ser Gly Ser Trp Thr Asn Ala Thr Leu Leu Ala Ala Met Lys
            115                 120                 125

Asn His Ile Thr Asn Val Val Thr His Tyr Lys Gly Lys Cys Tyr Ala
        130                 135                 140

Trp Asp Val Val Asn Glu Ala Leu Asn Glu Asp Gly Thr Phe Arg Asn
145                 150                 155                 160

Ser Val Phe Tyr Gln Ile Ile Gly Pro Ala Tyr Ile Pro Ile Ala Phe
                165                 170                 175

Ala Thr Ala Ala Ala Ala Asp Pro Asp Val Lys Leu Tyr Tyr Asn Asp
            180                 185                 190

Tyr Asn Ile Glu Tyr Ser Gly Ala Lys Ala Thr Ala Ala Gln Asn Ile
        195                 200                 205

Val Lys Met Ile Lys Ala Tyr Gly Ala Lys Ile Asp Gly Val Gly Leu
210                 215                 220

Gln Ala His Phe Ile Val Gly Ser Thr Pro Ser Gln Ser Asp Leu Thr
225                 230                 235                 240

Thr Val Leu Lys Gly Tyr Thr Ala Leu Gly Val Glu Val Ala Tyr Thr
            245                 250                 255

Glu Leu Asp Ile Arg Met Gln Leu Pro Ser Thr Ala Ala Lys Leu Ala
            260                 265                 270

Gln Gln Ser Thr Asp Phe Gln Gly Val Ala Ala Cys Val Ser Thr
            275                 280                 285

Thr Gly Cys Val Gly Val Thr Ile Trp Asp Trp Thr Asp Lys Tyr Ser
        290                 295                 300

Trp Val Pro Ser Val Phe Gln Gly Tyr Gly Ala Pro Leu Pro Trp Asp
305                 310                 315                 320

Glu Asn Tyr Val Lys Lys Pro Ala Tyr Asp Gly Leu Met Ala Gly Leu
            325                 330                 335

Gly Ala Ser Gly Ser Gly Thr Thr Thr Thr Thr Thr Thr Thr Ser Thr
            340                 345                 350

Thr Thr Gly Gly Thr Asp Pro Thr Gly Val Ala Gln Lys Trp Gly Gln
            355                 360                 365

Cys Gly Gly Ile Gly Trp Thr Gly Pro Thr Thr Cys Val Ser Gly Thr
        370                 375                 380

Thr Cys Gln Lys Leu Asn Asp Trp Tyr Ser Gln Cys Leu
385                 390                 395
```

<210> SEQ ID NO 21
<211> LENGTH: 2376

<212> TYPE: DNA
<213> ORGANISM: Aspergillus fumigatus

<400> SEQUENCE: 21

```
atggcggttg ccaaatctat tgctgccgtg ctggtagcac tgttgcctgg tgcgcttgct      60
caggcgaata caagctatgt tgattacaat gtggaggcga atccggatct cacccctcag     120
tcggtcgcta cgattgacct gtcctttccc gactgcgaga atggaccgct cagcaagact     180
ctcgtttgcg acacgtcggc tcggccgcat gaccgagctg ctgccctggt ttccatgttc     240
accttcgagg agctggtgaa caacacaggc aacactagcc ctggtgttcc aagacttggt     300
ctccctccgt accaagtatg gagcgaggct ctccatggac ttgaccgcgc caacttcaca     360
aacgagggag agtacagctg ggccacctcg ttccccatgc ctatcctgac aatgtcggcc     420
ttgaaccgaa ccctgatcaa ccagatcgcg accatcatcg caactcaagg acgagctttc     480
aataacgttg gcggtatgg gctggacgtg tacgccccga atataaatgc attcagatcg     540
gctatgtggg aagaggtca agagaccccc ggagaagacg cttactgcct ggcatcggcg     600
tatgcgtacg agtatatcac tggcatccag ggtggtgttg atccggaaca cctcaagttg     660
gtggccactg ccaaacacta tgcgggctac gatcttgaga ctgggacgg tcactcccgt     720
ttgggcaacg atatgaacat tacacagcag gaactttccg aatactacac ccctcagttc     780
cttgttgcag ccagagacgc caaagtgcac agtgtcatgt gctcctacaa cgcggtaaat     840
ggggtgccca gctgcgcaaa ctcgttcttc ctccagaccc tcctccgtga cacattcggc     900
ttcgtcgagg atggttatgt atccagcgac tgcgactcgg cgtacaatgt ctggaacccg     960
cacgagtttg cggccaacat cacgggggcc gctgcagact ctatccgggc ggggacggac    1020
attgattgcg gcactactta tcaatactat ttcggcgaag cctttgacga gcaagaggtc    1080
acccgtgcag aaatcgaaag aggtgtgatc cgcctgtaca gcaacttggt gcgtctcggc    1140
tatttcgatg gcaatggaag cgtgtatcgg gacctgacgt ggaatgatgt cgtgaccacg    1200
gatgcctgga atatctcata cgaagccgct gtagaaggca ttgtcctact gaagaacgat    1260
ggaaccttgc ctctcgccaa gtcggtccga agtgttgcat tgattgggcc ctggatgaat    1320
gtgacgactc agcttcaggg caactacttt ggaccggcgc cttatctgat tagtccgttg    1380
aatgccttcc agaattctga cttcgacgtg aactacgctt tcggcacgaa catttcatcc    1440
cactccacag atgggttttc cgaggcgttg tctgctgcga gaaatccga cgtcatcata    1500
ttcgcgggcg ggattgacaa cactttggaa gcagaagcca tggatcgcat gaatatcaca    1560
tggcccggca atcagctaca gctcatcgac cagttgagcc aactcggcaa ccgctgatc    1620
gtcctccaga tgggcggcgg ccaagtcgac tcctcctcgc tcaagtccaa caagaatgtc    1680
aactccctga tctggggtgg atacccccga caatccggcg gcaggctct cctagacatc    1740
atcaccggca agcgcgcccc cgccggccga ctcgtggtca cgcagtaccc ggccgaatac    1800
gcaacccagt tccccgccac cgacatgagc ctgcggcctc acggcaataa tcccggccag    1860
acctacatgt ggtacaccgg cacccccgtc tacgagtttg ccacgggct cttctacacg    1920
accttccacg cctccctccc tggcaccggc aaggacaaga cctccttcaa catccaagac    1980
ctcctcacgc agccgcatcc gggcttcgca acgtcgagc aaatgccttt gctcaacttc    2040
accgtgacga tcaccaatac cggcaaggtc gcttccgact acactgctat gctcttcgcg    2100
aacaccaccg cgggacctgc tccataccg aacaagtggc tcgtcggctt cgaccggctg    2160
gcgagcctgg aaccgcacag gtcgcagact atgaccatcc ccgtgactat cgacagcgtg    2220
```

-continued

```
gctcgtacgg atgaggccgg caatcgggtt ctctacccgg gaaagtacga gttggccctg    2280
aacaatgagc ggtcggttgt ccttcagttt gtgctgacag ccgagaggc tgtgattttc    2340 aagtggcctg tagagcagca gcagatttcg tctgcg                              2376
```

<210> SEQ ID NO 22
<211> LENGTH: 792
<212> TYPE: PRT
<213> ORGANISM: Aspergillus fumigatus

<400> SEQUENCE: 22

```
Met Ala Val Ala Lys Ser Ile Ala Ala Val Leu Val Ala Leu Leu Pro
1               5                   10                  15

Gly Ala Leu Ala Gln Ala Asn Thr Ser Tyr Val Asp Tyr Asn Val Glu
                20                  25                  30

Ala Asn Pro Asp Leu Thr Pro Gln Ser Val Ala Thr Ile Asp Leu Ser
            35                  40                  45

Phe Pro Asp Cys Glu Asn Gly Pro Leu Ser Lys Thr Leu Val Cys Asp
        50                  55                  60

Thr Ser Ala Arg Pro His Asp Arg Ala Ala Leu Val Ser Met Phe
65                  70                  75                  80

Thr Phe Glu Glu Leu Val Asn Asn Thr Gly Asn Thr Ser Pro Gly Val
                85                  90                  95

Pro Arg Leu Gly Leu Pro Pro Tyr Gln Val Trp Ser Glu Ala Leu His
            100                 105                 110

Gly Leu Asp Arg Ala Asn Phe Thr Asn Glu Gly Glu Tyr Ser Trp Ala
        115                 120                 125

Thr Ser Phe Pro Met Pro Ile Leu Thr Met Ser Ala Leu Asn Arg Thr
130                 135                 140

Leu Ile Asn Gln Ile Ala Thr Ile Ile Ala Thr Gln Gly Arg Ala Phe
145                 150                 155                 160

Asn Asn Val Gly Arg Tyr Gly Leu Asp Val Tyr Ala Pro Asn Ile Asn
                165                 170                 175

Ala Phe Arg Ser Ala Met Trp Gly Arg Gly Gln Glu Thr Pro Gly Glu
            180                 185                 190

Asp Ala Tyr Cys Leu Ala Ser Ala Tyr Ala Tyr Glu Tyr Ile Thr Gly
        195                 200                 205

Ile Gln Gly Gly Val Asp Pro Glu His Leu Lys Leu Val Ala Thr Ala
210                 215                 220

Lys His Tyr Ala Gly Tyr Asp Leu Glu Asn Trp Asp Gly His Ser Arg
225                 230                 235                 240

Leu Gly Asn Asp Met Asn Ile Thr Gln Gln Glu Leu Ser Glu Tyr Tyr
                245                 250                 255

Thr Pro Gln Phe Leu Val Ala Ala Arg Asp Ala Lys Val His Ser Val
            260                 265                 270

Met Cys Ser Tyr Asn Ala Val Asn Gly Val Pro Ser Cys Ala Asn Ser
        275                 280                 285

Phe Phe Leu Gln Thr Leu Leu Arg Asp Thr Phe Gly Phe Val Glu Asp
    290                 295                 300

Gly Tyr Val Ser Ser Asp Cys Asp Ser Ala Tyr Asn Val Trp Asn Pro
305                 310                 315                 320

His Glu Phe Ala Ala Asn Ile Thr Gly Ala Ala Ala Asp Ser Ile Arg
                325                 330                 335

Ala Gly Thr Asp Ile Asp Cys Gly Thr Thr Tyr Gln Tyr Tyr Phe Gly
            340                 345                 350
```

```
Glu Ala Phe Asp Glu Gln Glu Val Thr Arg Ala Glu Ile Glu Arg Gly
        355                 360                 365

Val Ile Arg Leu Tyr Ser Asn Leu Val Arg Leu Gly Tyr Phe Asp Gly
        370                 375                 380

Asn Gly Ser Val Tyr Arg Asp Leu Thr Trp Asn Asp Val Val Thr Thr
385                 390                 395                 400

Asp Ala Trp Asn Ile Ser Tyr Glu Ala Ala Val Glu Gly Ile Val Leu
                405                 410                 415

Leu Lys Asn Asp Gly Thr Leu Pro Leu Ala Lys Ser Val Arg Ser Val
                420                 425                 430

Ala Leu Ile Gly Pro Trp Met Asn Val Thr Thr Gln Leu Gln Gly Asn
        435                 440                 445

Tyr Phe Gly Pro Ala Pro Tyr Leu Ile Ser Pro Leu Asn Ala Phe Gln
        450                 455                 460

Asn Ser Asp Phe Asp Val Asn Tyr Ala Phe Gly Thr Asn Ile Ser Ser
465                 470                 475                 480

His Ser Thr Asp Gly Phe Ser Glu Ala Leu Ser Ala Ala Lys Lys Ser
                485                 490                 495

Asp Val Ile Ile Phe Ala Gly Gly Ile Asp Asn Thr Leu Glu Ala Glu
        500                 505                 510

Ala Met Asp Arg Met Asn Ile Thr Trp Pro Gly Asn Gln Leu Gln Leu
        515                 520                 525

Ile Asp Gln Leu Ser Gln Leu Gly Lys Pro Leu Ile Val Leu Gln Met
        530                 535                 540

Gly Gly Gly Gln Val Asp Ser Ser Ser Leu Lys Ser Asn Lys Asn Val
545                 550                 555                 560

Asn Ser Leu Ile Trp Gly Gly Tyr Pro Gly Gln Ser Gly Gly Gln Ala
                565                 570                 575

Leu Leu Asp Ile Ile Thr Gly Lys Arg Ala Pro Ala Gly Arg Leu Val
                580                 585                 590

Val Thr Gln Tyr Pro Ala Glu Tyr Ala Thr Gln Phe Pro Ala Thr Asp
        595                 600                 605

Met Ser Leu Arg Pro His Gly Asn Asn Pro Gly Gln Thr Tyr Met Trp
        610                 615                 620

Tyr Thr Gly Thr Pro Val Tyr Glu Phe Gly His Gly Leu Phe Tyr Thr
625                 630                 635                 640

Thr Phe His Ala Ser Leu Pro Gly Thr Gly Lys Asp Lys Thr Ser Phe
                645                 650                 655

Asn Ile Gln Asp Leu Leu Thr Gln Pro His Pro Gly Phe Ala Asn Val
                660                 665                 670

Glu Gln Met Pro Leu Leu Asn Phe Thr Val Thr Ile Thr Asn Thr Gly
        675                 680                 685

Lys Val Ala Ser Asp Tyr Thr Ala Met Leu Phe Ala Asn Thr Thr Ala
        690                 695                 700

Gly Pro Ala Pro Tyr Pro Asn Lys Trp Leu Val Gly Phe Asp Arg Leu
705                 710                 715                 720

Ala Ser Leu Glu Pro His Arg Ser Gln Thr Met Thr Ile Pro Val Thr
                725                 730                 735

Ile Asp Ser Val Ala Arg Thr Asp Glu Ala Gly Asn Arg Val Leu Tyr
        740                 745                 750

Pro Gly Lys Tyr Glu Leu Ala Leu Asn Asn Glu Arg Ser Val Val Leu
        755                 760                 765
```

Gln Phe Val Leu Thr Gly Arg Glu Ala Val Ile Phe Lys Trp Pro Val
770                 775                 780

Gln Gln Gln Ile Ser Ser Ala
785             790

<210> SEQ ID NO 23
<211> LENGTH: 2502
<212> TYPE: DNA
<213> ORGANISM: Thermoascus aurantiacus

<400> SEQUENCE: 23

| | | | | |
|---|---|---|---|---|
| atgcgcgcaa | ttggacttct | gccaggcatc | atcggcattg | ctggtgctgc ctgtccttac | 60 |
| atgacaggcg | agctgccgcg | ctccttcgcc | gagaaccctc | atgctatcaa ccgtcgtgct | 120 |
| gagggtggtg | gtggtgccgc | tgccgagacg | gagaagttcc | tgtctcagtt ctacctgaac | 180 |
| gacaacgaca | ccttcatgac | caccgatgtt | ggcggtccaa | ttgaggatca gaacagtctc | 240 |
| agcgctggtg | acagaggtcc | taccctgctg | gaggacttca | tcctccgtca aaagatccag | 300 |
| cgctttgacc | atgagcgggt | aggttgatct | ttactttcgg | ccttcttcga gcggggtgat | 360 |
| attaaaacag | gtaataggtg | cccgagcgtg | ctgtccatgc | ccgaggagcg ggagcgcatg | 420 |
| gcgtgttcac | atcctacgca | gactggtcca | acatcactgc | cgcttccttc ctgtctgctg | 480 |
| caggaaagga | gacacctgtc | tttgtccggt | tctccactgt | agcaggaagc agaggaagcg | 540 |
| cagacacggc | gcgtgacgtg | cacggtttcg | cgacgaggtt | ctacacggat gaagggaact | 600 |
| tcggtaggca | actatcatgc | tctctttaaa | tgttctcgat | ctgacagcca gcagacattg | 660 |
| tcggcaacaa | catccctgtc | ttcttcattc | aagatgcgat | ccagttcccc gacctgatcc | 720 |
| atgctgtcaa | gcccagcccg | aacaacgaga | tccctcaggc | cgcaaccgcc catgactctg | 780 |
| cctgggactt | tttcagccag | cagccgagct | ctttgcatac | tctgttctgg gctatggccg | 840 |
| gtcatggcat | tcctcgttcc | tacaggaaca | tggatggctt | cggcatccac accttccgct | 900 |
| ttgtgacgga | cgatggagct | tccaagctcg | tcaagttcca | ctggacgtcg ctgcagggca | 960 |
| aggcgagcct | tgtgtgggaa | gaggcacagg | ccgtggctgg | aaagaacgcg gactatcacc | 1020 |
| gccaggactt | gtgggacgca | atcgaggctg | aaggtaccc | tgagtgggag gtaggctctc | 1080 |
| cctgctatgt | atggatgtgc | cagaagctta | ataatggcct | agctcggcgt gcaaatcatg | 1140 |
| gatgaggaag | accagctgcg | ctttggcttc | gatctgttgg | acccgaccaa gatcgttccc | 1200 |
| gaggaatacg | tgcccatcac | gaagctcgga | agatgcagc | tcaaccgcaa cccgctgaac | 1260 |
| tacttcgccg | agactgaaca | gatcatggtc | agttcgccac | cgtgttcggt tgctcgttgc | 1320 |
| tgaagtgcta | acttgcaaca | gttccaaccg | ggtcacgttg | tccgtggcat tgatttcacc | 1380 |
| gaggaccctc | tgctccaggg | acgtctcttc | tcttacctcg | acaccagct caaccgccac | 1440 |
| ggaggtccga | acttcgagca | gatccccatc | aaccggccac | gcactccaat tcacaacaac | 1500 |
| aaccgtgacg | gagccggtat | gctagcccat | gtattccttt | ctttatgcat ttttatatga | 1560 |
| tgcgttctaa | cggcaacagc | gcaaatgtac | atccccctga | caaggcggc gtacacccc | 1620 |
| aacactctga | caacggctc | ccccaagcag | gccaaccaga | cggtcggaaa gggcttcttc | 1680 |
| acgactccag | gccggacggc | aagcggcagg | cttgtgcgcg | ccgtcagctc aaccttcgcc | 1740 |
| gacgtctggt | cgcagcctcg | tctgttctac | aactccctcg | tgccggcgga gcagcagttc | 1800 |
| ctgatcaacg | cgatccgctt | tgagacggcc | cacatcacga | gcgacgtcgt gaagaacaac | 1860 |
| gtcatcatcc | agctgaaccg | cgtgagcaac | aacctcgcca | agagagtcgc ccgggccatc | 1920 |
| ggtgtcgcgg | agcccgagcc | agacccaacc | ttgtaccaca | caacaagac cgccaacgtc | 1980 |

```
ggggtgttcg gcaagccgct cgccagactc gacggcctgc aggtcggggt cctcgccacc   2040
gtcaacaagc ccgactcgat caagcaggcc gccagcctga aggccagctt cgcggcggac   2100
aacgtcgacg tcaaggtcgt cgcggagcgc ctcgccgacg gcgtcgacga gacctactcg   2160
gccgccgacg cggtcaactt cgacgccatc ctggtcgcca acggcgctga gggcctcttc   2220
gcgcgcgaca gcttcaccgc caggccggcc aactcgacca ccgcgacgct ctaccccgcg   2280
ggccgcccgc tccagatcct ggtcgacggg ttccgctacg gcaagccggt cggggcgctc   2340
ggcagcggcg ccaaggcgct cgacgcagcg gagatttcga cgacccgggc cggcgtgtac   2400
gtcgccaact cgacgaccga cagcttcatc aatggcgtca gggacggtct gcggacgttc   2460
aagttcctgg accggttcgc gattgacgag gatgctgagt ga                      2502

<210> SEQ ID NO 24
<211> LENGTH: 740
<212> TYPE: PRT
<213> ORGANISM: Thermoascus aurantiacus

<400> SEQUENCE: 24

Met Arg Ala Ile Gly Leu Leu Pro Gly Ile Ile Gly Ile Ala Gly Ala
1               5                   10                  15

Ala Cys Pro Tyr Met Thr Gly Glu Leu Pro Arg Ser Phe Ala Glu Asn
            20                  25                  30

Pro His Ala Ile Asn Arg Arg Ala Glu Gly Gly Gly Ala Ala Ala
        35                  40                  45

Glu Thr Glu Lys Phe Leu Ser Gln Phe Tyr Leu Asn Asp Asn Asp Thr
    50                  55                  60

Phe Met Thr Thr Asp Val Gly Gly Pro Ile Glu Asp Gln Asn Ser Leu
65                  70                  75                  80

Ser Ala Gly Asp Arg Gly Pro Thr Leu Leu Glu Asp Phe Ile Leu Arg
                85                  90                  95

Gln Lys Ile Gln Arg Phe Asp His Glu Arg Val Pro Glu Arg Ala Val
            100                 105                 110

His Ala Arg Gly Ala Gly Ala His Gly Val Phe Thr Ser Tyr Ala Asp
        115                 120                 125

Trp Ser Asn Ile Thr Ala Ala Ser Phe Leu Ser Ala Ala Gly Lys Glu
    130                 135                 140

Thr Pro Val Phe Val Arg Phe Ser Thr Val Ala Gly Ser Arg Gly Ser
145                 150                 155                 160

Ala Asp Thr Ala Arg Asp Val His Gly Phe Ala Thr Arg Phe Tyr Thr
                165                 170                 175

Asp Glu Gly Asn Phe Asp Ile Val Gly Asn Asn Ile Pro Val Phe Phe
            180                 185                 190

Ile Gln Asp Ala Ile Gln Phe Pro Asp Leu Ile His Ala Val Lys Pro
        195                 200                 205

Ser Pro Asn Asn Glu Ile Pro Gln Ala Ala Thr Ala His Asp Ser Ala
    210                 215                 220

Trp Asp Phe Phe Ser Gln Gln Pro Ser Ser Leu His Thr Leu Phe Trp
225                 230                 235                 240

Ala Met Ala Gly His Gly Ile Pro Arg Ser Tyr Arg Asn Met Asp Gly
                245                 250                 255

Phe Gly Ile His Thr Phe Arg Phe Val Thr Asp Asp Gly Ala Ser Lys
            260                 265                 270

Leu Val Lys Phe His Trp Thr Ser Leu Gln Gly Lys Ala Ser Leu Val
```

-continued

```
                275                 280                 285
Trp Glu Glu Ala Gln Ala Val Ala Gly Lys Asn Ala Asp Tyr His Arg
    290                 295                 300
Gln Asp Leu Trp Asp Ala Ile Glu Ala Gly Arg Tyr Pro Glu Trp Glu
305                 310                 315                 320
Leu Gly Val Gln Ile Met Asp Glu Glu Gln Leu Arg Phe Gly Phe
                325                 330                 335
Asp Leu Leu Asp Pro Thr Lys Ile Val Pro Glu Glu Tyr Val Pro Ile
                340                 345                 350
Thr Lys Leu Gly Lys Met Gln Leu Asn Arg Asn Pro Leu Asn Tyr Phe
            355                 360                 365
Ala Glu Thr Glu Gln Ile Met Phe Gln Pro Gly His Val Val Arg Gly
        370                 375                 380
Ile Asp Phe Thr Glu Asp Pro Leu Leu Gln Gly Arg Leu Phe Ser Tyr
385                 390                 395                 400
Leu Asp Thr Gln Leu Asn Arg His Gly Gly Pro Asn Phe Glu Gln Ile
                405                 410                 415
Pro Ile Asn Arg Pro Arg Thr Pro Ile His Asn Asn Arg Asp Gly
                420                 425                 430
Ala Ala Gln Met Tyr Ile Pro Leu Asn Lys Ala Ala Tyr Thr Pro Asn
            435                 440                 445
Thr Leu Asn Asn Gly Ser Pro Lys Gln Ala Asn Gln Thr Val Gly Lys
        450                 455                 460
Gly Phe Phe Thr Thr Pro Gly Arg Thr Ala Ser Gly Arg Leu Val Arg
465                 470                 475                 480
Ala Val Ser Ser Thr Phe Ala Asp Val Trp Ser Gln Pro Arg Leu Phe
                485                 490                 495
Tyr Asn Ser Leu Val Pro Ala Glu Gln Gln Phe Leu Ile Asn Ala Ile
            500                 505                 510
Arg Phe Glu Thr Ala His Ile Thr Ser Asp Val Val Lys Asn Asn Val
        515                 520                 525
Ile Ile Gln Leu Asn Arg Val Ser Asn Asn Leu Ala Lys Arg Val Ala
    530                 535                 540
Arg Ala Ile Gly Val Ala Glu Pro Glu Pro Asp Pro Thr Leu Tyr His
545                 550                 555                 560
Asn Asn Lys Thr Ala Asn Val Gly Val Phe Gly Lys Pro Leu Ala Arg
                565                 570                 575
Leu Asp Gly Leu Gln Val Gly Val Leu Ala Thr Val Asn Lys Pro Asp
            580                 585                 590
Ser Ile Lys Gln Ala Ala Ser Leu Lys Ala Ser Phe Ala Ala Asp Asn
        595                 600                 605
Val Asp Val Lys Val Val Glu Arg Leu Ala Asp Gly Val Asp Glu
    610                 615                 620
Thr Tyr Ser Ala Ala Asp Ala Val Asn Phe Asp Ala Ile Leu Val Ala
625                 630                 635                 640
Asn Gly Ala Glu Gly Leu Phe Ala Arg Asp Ser Phe Thr Ala Arg Pro
                645                 650                 655
Ala Asn Ser Thr Thr Ala Thr Leu Tyr Pro Ala Gly Arg Pro Leu Gln
            660                 665                 670
Ile Leu Val Asp Gly Phe Arg Tyr Gly Lys Pro Val Gly Ala Leu Gly
        675                 680                 685
Ser Gly Ala Lys Ala Leu Asp Ala Ala Glu Ile Ser Thr Thr Arg Ala
    690                 695                 700
```

Gly Val Tyr Val Ala Asn Ser Thr Thr Asp Ser Phe Ile Asn Gly Val
705                 710                 715                 720

Arg Asp Gly Leu Arg Thr Phe Lys Phe Leu Asp Arg Phe Ala Ile Asp
                725                 730                 735

Glu Asp Ala Glu
            740

<210> SEQ ID NO 25
<211> LENGTH: 1599
<212> TYPE: DNA
<213> ORGANISM: Aspergillus fumigatus

<400> SEQUENCE: 25

| | | | | | |
|---|---|---|---|---|---|
| atgctggcct | ccaccttctc | ctaccgcatg | tacaagaccg | cgctcatcct | ggccgccctt | 60 |
| ctgggctctg | gccaggctca | gcaggtcggt | acttcccagg | cggaagtgca | tccgtccatg | 120 |
| acctggcaga | gctgcacggc | tggcggcagc | tgcaccacca | caacggcaa | ggtggtcatc | 180 |
| gacgcgaact | ggcgttgggt | gcacaaagtc | ggcgactaca | ccaactgcta | caccggcaac | 240 |
| acctgggaca | cgactatctg | ccctgacgat | gcgacctgcg | catccaactg | cgcccttgag | 300 |
| ggtgccaact | acgaatccac | ctatggtgtg | accgccagcg | gcaattccct | ccgcctcaac | 360 |
| ttcgtcacca | ccagccagca | gaagaacatt | ggctcgcgtc | tgtacatgat | gaaggacgac | 420 |
| tcgacctacg | agatgtttaa | gctgctgaac | caggagttca | ccttcgatgt | cgatgtctcc | 480 |
| aacctcccct | gcggtctcaa | cggtgctctg | tactttgtcg | ccatggacgc | cgacggtggc | 540 |
| atgtccaagt | acccaaccaa | caaggccggt | gccaagtacg | gtactggata | ctgtgactcg | 600 |
| cagtgccctc | gcgacctcaa | gttcatcaac | ggtcaggcca | cgtcgaagg | gtggcagccc | 660 |
| tcctccaacg | atgccaatgc | gggtaccggc | aaccacgggt | cctgctgcgc | ggagatggat | 720 |
| atctgggagg | ccaacagcat | ctccacggcc | ttcacccccc | atccgtgcga | cacgccccggc | 780 |
| caggtgatgt | gcaccggtga | tgcctgcggt | ggcacctaca | gctccgaccg | ctacggcggc | 840 |
| acctgcgacc | ccgacggatg | tgatttcaac | tccttccgcc | agggcaacaa | gaccttctac | 900 |
| ggccctggca | tgaccgtcga | caccaagagc | aagtttaccg | tcgtcaccca | gttcatcacc | 960 |
| gacgacggca | cctccagcgg | caccctcaag | gagatcaagc | gcttctacgt | gcagaacggc | 1020 |
| aaggtgatcc | ccaactcgga | gtcgacctgg | accggcgtca | gcggcaactc | catcaccacc | 1080 |
| gagtactgca | ccgcccagaa | gagcctgttc | caggaccaga | cgtcttcga | aaagcacggc | 1140 |
| ggcctcgagg | gcatgggtgc | tgccctcgcc | cagggtatgg | ttctcgtcat | gtccctgtgg | 1200 |
| gatgatcact | cggccaacat | gctctggctc | gacagcaact | acccgaccac | tgcctcttcc | 1260 |
| accactcccg | gcgtcgcccg | tggtacctgc | gacatctcct | ccggcgtccc | tgcggatgtc | 1320 |
| gaggcgaacc | accccgacgc | ctacgtcgtc | tactccaaca | tcaaggtcgg | ccccatcggc | 1380 |
| tcgaccttca | cagcggtgg | ctcgaacccc | ggtggcggaa | ccaccacgac | aactaccacc | 1440 |
| cagcctacta | ccaccacgac | cacggctgga | accctggcg | caccggagt | cgcacagcac | 1500 |
| tatggccagt | gtggtggaat | cggatggacc | ggacccacaa | cctgtgccag | cccttatacc | 1560 |
| tgccagaagc | tgaatgatta | ttactctcag | tgcctgtag | | | 1599 |

<210> SEQ ID NO 26
<211> LENGTH: 532
<212> TYPE: PRT
<213> ORGANISM: Aspergillus fumigatus

<400> SEQUENCE: 26

```
Met Leu Ala Ser Thr Phe Ser Tyr Arg Met Tyr Lys Thr Ala Leu Ile
1               5                   10                  15

Leu Ala Ala Leu Leu Gly Ser Gly Gln Ala Gln Val Gly Thr Ser
            20                  25                  30

Gln Ala Glu Val His Pro Ser Met Thr Trp Gln Ser Cys Thr Ala Gly
        35                  40                  45

Gly Ser Cys Thr Thr Asn Asn Gly Lys Val Val Ile Asp Ala Asn Trp
    50                  55                  60

Arg Trp Val His Lys Val Gly Asp Tyr Thr Asn Cys Tyr Thr Gly Asn
65                  70                  75                  80

Thr Trp Asp Thr Thr Ile Cys Pro Asp Asp Ala Thr Cys Ala Ser Asn
                85                  90                  95

Cys Ala Leu Glu Gly Ala Asn Tyr Glu Ser Thr Tyr Gly Val Thr Ala
                100                 105                 110

Ser Gly Asn Ser Leu Arg Leu Asn Phe Val Thr Thr Ser Gln Gln Lys
        115                 120                 125

Asn Ile Gly Ser Arg Leu Tyr Met Met Lys Asp Asp Ser Thr Tyr Glu
    130                 135                 140

Met Phe Lys Leu Leu Asn Gln Glu Phe Thr Phe Asp Val Asp Val Ser
145                 150                 155                 160

Asn Leu Pro Cys Gly Leu Asn Gly Ala Leu Tyr Phe Val Ala Met Asp
                165                 170                 175

Ala Asp Gly Gly Met Ser Lys Tyr Pro Thr Asn Lys Ala Gly Ala Lys
                180                 185                 190

Tyr Gly Thr Gly Tyr Cys Asp Ser Gln Cys Pro Arg Asp Leu Lys Phe
        195                 200                 205

Ile Asn Gly Gln Ala Asn Val Glu Gly Trp Gln Pro Ser Ser Asn Asp
    210                 215                 220

Ala Asn Ala Gly Thr Gly Asn His Gly Ser Cys Cys Ala Glu Met Asp
225                 230                 235                 240

Ile Trp Glu Ala Asn Ser Ile Ser Thr Ala Phe Thr Pro His Pro Cys
                245                 250                 255

Asp Thr Pro Gly Gln Val Met Cys Thr Gly Asp Ala Cys Gly Gly Thr
                260                 265                 270

Tyr Ser Ser Asp Arg Tyr Gly Gly Thr Cys Asp Pro Asp Gly Cys Asp
        275                 280                 285

Phe Asn Ser Phe Arg Gln Gly Asn Lys Thr Phe Tyr Gly Pro Gly Met
    290                 295                 300

Thr Val Asp Thr Lys Ser Lys Phe Thr Val Val Thr Gln Phe Ile Thr
305                 310                 315                 320

Asp Asp Gly Thr Ser Ser Gly Thr Leu Lys Glu Ile Lys Arg Phe Tyr
                325                 330                 335

Val Gln Asn Gly Lys Val Ile Pro Asn Ser Glu Ser Thr Trp Thr Gly
                340                 345                 350

Val Ser Gly Asn Ser Ile Thr Thr Glu Tyr Cys Thr Ala Gln Lys Ser
        355                 360                 365

Leu Phe Gln Asp Gln Asn Val Phe Glu Lys His Gly Gly Leu Glu Gly
    370                 375                 380

Met Gly Ala Ala Leu Ala Gln Gly Met Val Leu Val Met Ser Leu Trp
385                 390                 395                 400

Asp Asp His Ser Ala Asn Met Leu Trp Leu Asp Ser Asn Tyr Pro Thr
                405                 410                 415
```

```
Thr Ala Ser Ser Thr Thr Pro Gly Val Ala Arg Gly Thr Cys Asp Ile
            420                 425                 430

Ser Ser Gly Val Pro Ala Asp Val Glu Ala Asn His Pro Asp Ala Tyr
        435                 440                 445

Val Val Tyr Ser Asn Ile Lys Val Gly Pro Ile Gly Ser Thr Phe Asn
    450                 455                 460

Ser Gly Gly Ser Asn Pro Gly Gly Thr Thr Thr Thr Thr Thr
465             470              475                 480

Gln Pro Thr Thr Thr Thr Thr Ala Gly Asn Pro Gly Gly Thr Gly
                485                 490                 495

Val Ala Gln His Tyr Gly Gln Cys Gly Gly Ile Gly Trp Thr Gly Pro
        500                 505                 510

Thr Thr Cys Ala Ser Pro Tyr Thr Cys Gln Lys Leu Asn Asp Tyr Tyr
        515                 520                 525

Ser Gln Cys Leu
    530

<210> SEQ ID NO 27
<211> LENGTH: 1713
<212> TYPE: DNA
<213> ORGANISM: Aspergillus fumigatus

<400> SEQUENCE: 27
atgaagcacc ttgcatcttc catcgcattg actctactgt tgcctgccgt gcaggcccag        60
cagaccgtat ggggccaatg tatgttctgg ctgtcactgg aataagactg tatcaactgc      120
tgatatgctt ctaggtggcg gccaaggctg gtctggcccg acgagctgtg ttgccggcgc      180
agcctgtagc acactgaatc cctgtatgtt agatatcgtc ctgagtggag acttatactg      240
acttccttag actacgctca gtgtatcccg ggagccaccg cgacgtccac caccctcacg      300
acgacgacgg cggcgacgac gacatcccag accaccacca aacctaccac gactggtcca      360
actacatccg cacccaccgt gaccgcatcc ggtaacccgt tcagcggcta ccagctgtat      420
gccaacccct actactcctc cgaggtccat actctggcca tgccttctct gcccagctcg      480
ctgcagccca aggctagtgc tgttgctgaa gtgccctcat ttgtttggct gtaagtggcc      540
ttatcccaat actgagacca actctctgac agtcgtagcg acgttgccgc caaggtgccc      600
actatgggaa cctacctggc cgacattcag gccaagaaca aggccggcgc caaccctcct      660
atcgctggta tcttcgtggt ctacgacttg ccggaccgtg actgcgccgc tctggccagt      720
aatggcgagt actcaattgc caacaacggt gtggccaact acaaggcgta cattgacgcc      780
atccgtgctc agctggtgaa gtactctgac gttcacacca tcctcgtcat cggtaggccg      840
tacacctccg ttgcgcgccg cctttctctg acatcttgca gaacccgaca gcttggccaa      900
cctggtgacc aacctcaacg tcgccaaatg cgccaatgcg cagagcgcct acctggagtg      960
tgtcgactat gctctgaagc agctcaacct gcccaacgtc gccatgtacc tcgacgcagg     1020
tatgcctcac ttcccgcatt ctgtatccct tccagacact aactcatcag gccatgcggg     1080
ctggctcgga tggcccgcca acttgggccc cgccgcaaca ctcttcgcca agtctacac      1140 cgacgcgggt tccccgcgg ctgttcgtgg cctggccacc aacgtcgcca actacaacgc     1200
ctggtcgctc agtacctgcc cctcctacac ccagggagac cccaactgcg acgagaagaa     1260
gtacatcaac gccatggcgc ctcttctcaa ggaagccggc ttcgatgccc acttcatcat     1320
ggatacctgt aagtgcttat tccaatcgcc gatgtgtgcc gactaatcaa tgtttcagcc     1380
cggaatggcg tccagcccac gaagcaaaac gcctggggtg actggtgcaa cgtcatcggc     1440
```

```
accggcttcg gtgttcgccc ctcgactaac accggcgatc cgctccagga tgcctttgtg   1500
tggatcaagc cggtggaga gagtgatggc acgtccaact cgacttcccc ccggtatgac    1560
gcgcactgcg gatatagtga tgctctgcag cctgctcctg aggctggtac ttggttccag   1620
gtatgtcatc cattagccag atgagggata agtgactgac ggacctaggc ctactttgag   1680
cagcttctga ccaacgctaa cccgtccttt taa                                1713
```

<210> SEQ ID NO 28
<211> LENGTH: 454
<212> TYPE: PRT
<213> ORGANISM: Aspergillus fumigatus

<400> SEQUENCE: 28

```
Met Lys His Leu Ala Ser Ser Ile Ala Leu Thr Leu Leu Pro Ala
1               5                   10                  15

Val Gln Ala Gln Gln Thr Val Trp Gly Gln Cys Gly Gly Gln Gly Trp
            20                  25                  30

Ser Gly Pro Thr Ser Cys Val Ala Gly Ala Ala Cys Ser Thr Leu Asn
        35                  40                  45

Pro Tyr Tyr Ala Gln Cys Ile Pro Gly Ala Thr Ala Thr Ser Thr Thr
50                  55                  60

Leu Thr Thr Thr Thr Ala Ala Thr Thr Thr Ser Gln Thr Thr Thr Lys
65                  70                  75                  80

Pro Thr Thr Thr Gly Pro Thr Thr Ser Ala Pro Thr Val Thr Ala Ser
                85                  90                  95

Gly Asn Pro Phe Ser Gly Tyr Gln Leu Tyr Ala Asn Pro Tyr Tyr Ser
            100                 105                 110

Ser Glu Val His Thr Leu Ala Met Pro Ser Leu Pro Ser Ser Leu Gln
        115                 120                 125

Pro Lys Ala Ser Ala Val Ala Glu Val Pro Ser Phe Val Trp Leu Asp
130                 135                 140

Val Ala Ala Lys Val Pro Thr Met Gly Thr Tyr Leu Ala Asp Ile Gln
145                 150                 155                 160

Ala Lys Asn Lys Ala Gly Ala Asn Pro Ile Ala Gly Ile Phe Val
                165                 170                 175

Val Tyr Asp Leu Pro Asp Arg Asp Cys Ala Ala Leu Ala Ser Asn Gly
            180                 185                 190

Glu Tyr Ser Ile Ala Asn Asn Gly Val Ala Asn Tyr Lys Ala Tyr Ile
        195                 200                 205

Asp Ala Ile Arg Ala Gln Leu Val Lys Tyr Ser Asp Val His Thr Ile
210                 215                 220

Leu Val Ile Glu Pro Asp Ser Leu Ala Asn Leu Val Thr Asn Leu Asn
225                 230                 235                 240

Val Ala Lys Cys Ala Asn Ala Gln Ser Ala Tyr Leu Glu Cys Val Asp
                245                 250                 255

Tyr Ala Leu Lys Gln Leu Asn Leu Pro Asn Val Ala Met Tyr Leu Asp
            260                 265                 270

Ala Gly His Ala Gly Trp Leu Gly Trp Pro Ala Asn Leu Gly Pro Ala
        275                 280                 285

Ala Thr Leu Phe Ala Lys Val Tyr Thr Asp Ala Gly Ser Pro Ala Ala
    290                 295                 300

Val Arg Gly Leu Ala Thr Asn Val Ala Asn Tyr Asn Ala Trp Ser Leu
305                 310                 315                 320
```

Ser Thr Cys Pro Ser Tyr Thr Gln Gly Asp Pro Asn Cys Asp Glu Lys
            325                 330                 335

Lys Tyr Ile Asn Ala Met Ala Pro Leu Leu Lys Glu Ala Gly Phe Asp
        340                 345                 350

Ala His Phe Ile Met Asp Thr Ser Arg Asn Gly Val Gln Pro Thr Lys
            355                 360                 365

Gln Asn Ala Trp Gly Asp Trp Cys Asn Val Ile Gly Thr Gly Phe Gly
        370                 375                 380

Val Arg Pro Ser Thr Asn Thr Gly Asp Pro Leu Gln Asp Ala Phe Val
385                 390                 395                 400

Trp Ile Lys Pro Gly Gly Glu Ser Asp Gly Thr Ser Asn Ser Thr Ser
                405                 410                 415

Pro Arg Tyr Asp Ala His Cys Gly Tyr Ser Asp Ala Leu Gln Pro Ala
            420                 425                 430

Pro Glu Ala Gly Thr Trp Phe Gln Ala Tyr Phe Glu Gln Leu Leu Thr
        435                 440                 445

Asn Ala Asn Pro Ser Phe
    450

<210> SEQ ID NO 29
<211> LENGTH: 681
<212> TYPE: DNA
<213> ORGANISM: Thielavia terrestris

<400> SEQUENCE: 29

```
atgctcgcaa acggtgccat cgtcttcctg gccgccgccc tcggcgtcag tggccactac      60
acctggccac gggttaacga cggcgccgac tggcaacagg tccgtaaggc ggacaactgg     120
caggacaacg gctacgtcgg ggatgtcacg tcgccacaga tccgctgttt ccaggcgacc     180
ccgtccccgg ccccatccgt cctcaacacc acggccggct cgaccgtgac ctactgggcc     240
aaccccgacg tctaccaccc cgggcctgtg cagttttaca tggcccgcgt gcccgatggc     300
gaggacatca actcgtggaa cggcgacggc gccgtgtggt tcaaggtgta cgaggaccat     360 cctaccttg cgctcagct cacatggccc agcacgggca agagctcgtt cgcggttccc      420 atcccccgt gcatcaagtc cggctactac ctcctccggg cggagcaaat cggcctgcac     480
gtcgcccaga gcgtaggcgg agcgcagttc tacatctcat gcgcccagct cagcgtcacc     540
ggcggcggca gcaccgagcc gccgaacaag gtggccttcc ccggcgctta cagtgcgacg     600
gacccgggca ttctgatcaa catctactac cctgttccca cgtcctacca gaaccccggc     660
ccggccgtct tcagctgctg a                                              681
```

<210> SEQ ID NO 30
<211> LENGTH: 226
<212> TYPE: PRT
<213> ORGANISM: Thielavia terrestris

<400> SEQUENCE: 30

Met Leu Ala Asn Gly Ala Ile Val Phe Leu Ala Ala Ala Leu Gly Val
1               5                   10                  15

Ser Gly His Tyr Thr Trp Pro Arg Val Asn Asp Gly Ala Asp Trp Gln
            20                  25                  30

Gln Val Arg Lys Ala Asp Asn Trp Gln Asp Asn Gly Tyr Val Gly Asp
        35                  40                  45

Val Thr Ser Pro Gln Ile Arg Cys Phe Gln Ala Thr Pro Ser Pro Ala
    50                  55                  60

-continued

```
Pro Ser Val Leu Asn Thr Thr Ala Gly Ser Thr Val Thr Tyr Trp Ala
 65              70                  75                  80

Asn Pro Asp Val Tyr His Pro Gly Pro Val Gln Phe Tyr Met Ala Arg
             85                  90                  95

Val Pro Asp Gly Glu Asp Ile Asn Ser Trp Asn Gly Asp Gly Ala Val
            100                 105                 110

Trp Phe Lys Val Tyr Glu Asp His Pro Thr Phe Gly Ala Gln Leu Thr
        115                 120                 125

Trp Pro Ser Thr Gly Lys Ser Ser Phe Ala Val Pro Ile Pro Pro Cys
        130                 135                 140

Ile Lys Ser Gly Tyr Tyr Leu Leu Arg Ala Glu Gln Ile Gly Leu His
145                 150                 155                 160

Val Ala Gln Ser Val Gly Gly Ala Gln Phe Tyr Ile Ser Cys Ala Gln
            165                 170                 175

Leu Ser Val Thr Gly Gly Gly Ser Thr Glu Pro Pro Asn Lys Val Ala
            180                 185                 190

Phe Pro Gly Ala Tyr Ser Ala Thr Asp Pro Gly Ile Leu Ile Asn Ile
        195                 200                 205

Tyr Tyr Pro Val Pro Thr Ser Tyr Gln Asn Pro Gly Pro Ala Val Phe
    210                 215                 220

Ser Cys
225
```

TWO-STAGE PROCESS FOR ENZYMATIC HYDROLYSIS OF LIGNOCELLULOSIC BIOMASS

CROSS-REFERENCE TO RELATED APPLICATIONS

This application is a 35 U.S.C. 371 national application of international application no. PCT/US2016/022101 filed Mar. 11, 2016 which claims priority of the benefit under 35 U.S.C. 119 of U.S. provisional application no. 62/132,120 filed Mar. 12, 2015 the contents of which are fully incorporated herein by reference.

REFERENCE TO A SEQUENCE LISTING

This application contains a Sequence Listing in computer readable form, which is incorporated herein by reference.

FIELD OF THE INVENTION

The present invention relates generally to processes for enhancing enzymatic hydrolysis of biomass by conducting hydrolysis in at least two stages, where in a stage a first enzyme composition comprising a cellulolytic enzyme and an oxidoreductase and/or an AA9 (GH61) polypeptide having cellulolytic enhancing activity is added, followed by a latter stage in which a second enzyme composition comprising one or more cellulases is added. The invention also relates to processes for obtaining hydrolysis products and fermentation products using processes of the invention.

DESCRIPTION OF RELATED ART

Renewable energy sources provide an alternative to current fossil fuel dependence. Production of ethanol as an energy source includes the basic steps of hydrolysis and fermentation. These steps are integrated within larger processes to obtain ethanol from various source materials.

Lignocellulosic biomass is comprised of cellulose, hemicellulose and lignin. To make the biomass accessible for hydrolysis, pretreatment is often performed, which may increase availability of the material for hydrolysis and thereby increase yields from hydrolysis processes. Selection of a pretreatment method may depend on many factors, such as biomass type, source and composition.

While pretreatment methods are effective to render the biomass available for hydrolysis, such methods may also generate inhibitors to hydrolysis and/or fermentation. Ideally, a selected pretreatment method will balance these considerations, maximizing availability of the biomass for hydrolysis, while minimizing formation of inhibitors.

However, selection of a pretreatment method alone may not be sufficient to both minimize formation of inhibitors and maximize the availability of the biomass for hydrolysis. Various detoxification and preconditioning processes have been developed in order to address some of these issues, and further prepare the pretreated biomass for hydrolysis.

In the hydrolysis step the source material is hydrolyzed to break down cellulose and/or hemicellulose to fermentable sugars. Commonly, enzymatic hydrolysis is utilized, but the persistent presence of inhibitors (e.g., phenolics, monomers, oligomers, xylooligomers, acids, degradation products, etc.), as well as other limitations (e.g., high viscosity) may limit the yield achieved through hydrolysis.

Methods of pretreatment or detoxification have been described, such as in WO2013/148504, describing processes of treating pretreated biomass with a mixture of phenol oxidizing enzyme and a hemicellulase, WO2012/061517, describing processes of pretreating with GH61, and WO2008/134259, describing processes of detoxifying pretreated biomass with a phenol oxidizing enzyme, however additional processes for improving hydrolysis yields would be useful to the industry.

There is therefore a need in the art for additional processes of hydrolyzing lignocellulosic biomass that addresses the inhibitors that may be present from pretreatment and improves the production of fermentable sugars and/or fermentation yields. The present invention provides such processes.

SUMMARY OF THE INVENTION

Described herein are processes for hydrolyzing lignocellulosic material to improve yields of the resultant sugars for fermentation. The present invention is based on the surprising discovery that providing enzymes to the hydrolysis process in a divided manner, comprising at least two different enzyme compositions, increases the yield of glucose and/or xylose in the resultant hydrolyzate as compared to adding all enzymes for enzymatic hydrolysis simultaneously. As such, the invention provides a multi stage hydrolysis process in which the enzyme compositions are added in separate stages.

Thus in one aspect, the invention relates to a process of multi-stage hydrolysis of a lignocellulosic material, the process comprising: a) a step of contacting a lignocellulosic material with a first enzyme composition comprising one or more cellulolytic enzymes and at least one of an oxidoreductase and an AA9 (GH61) polypeptide having cellulolytic enhancing activity; and b) a saccharification step comprising combining the material of step a) with a second enzyme composition comprising one or more cellulases, wherein the first enzyme composition and the second enzyme composition are different enzyme compositions and wherein the process provides increased glucose yield compared to administration of enzymes in a single stage hydrolysis.

In another aspect, the invention relates to a process of producing a fermentation product from a lignocellulosic material, the process comprising the steps of: hydrolyzing the lignocellulosic material, comprising: a) a step of contacting a lignocellulosic material with a first enzyme composition comprising one or more cellulolytic enzymes and at least one of at least one of an oxidoreductase and an AA9 (GH61) polypeptide having cellulolytic enhancing activity; and b) a saccharification step comprising combining the material of step a) with a second enzyme composition comprising one or more cellulases, wherein the first enzyme composition and the second enzyme composition are different enzyme compositions and wherein the process provides increased glucose yield compared to administration of enzymes in a single stage hydrolysis; and fermenting the hydrolyzate to produce a fermentation product.

In a further aspect, the invention relates to a process of increasing a sugar (e.g., glucose, xylose) yield of hydrolysis of a lignocellulosic material, the process comprising the steps of: a) a step of contacting a lignocellulosic material with a first enzyme composition comprising one or more cellulolytic enzymes and at least one of an oxidoreductase and an AA9 (GH61) polypeptide having cellulolytic enhancing activity; and b) a saccharification step comprising combining the material of step a) with a second enzyme composition comprising one or more cellulases, wherein the first enzyme composition and the second enzyme composition are different enzyme compositions and wherein the process provides increased sugar yield compared to administration of enzymes in a single stage hydrolysis.

DEFINITIONS

Acetylxylan esterase: The term "acetylxylan esterase" means a carboxylesterase (EC 3.1.1.72) that catalyzes the hydrolysis of acetyl groups from polymeric xylan, acetylated xylose, acetylated glucose, alpha-napthyl acetate, and p-nitrophenyl acetate. Acetylxylan esterase activity can be determined using 0.5 mM p-nitrophenylacetate as substrate in 50 mM sodium acetate pH 5.0 containing 0.01% TWEEN™ 20 (polyoxyethylene sorbitan monolaurate). One unit of acetylxylan esterase is defined as the amount of enzyme capable of releasing 1 μmole of p-nitrophenolate anion per minute at pH 5, 25° C.

Allelic variant: The term "allelic variant" means any of two or more (e.g., several) alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-L-arabinofuranosidase: The term "alpha-L-arabinofuranosidase" means an alpha-L-arabinofuranoside arabinofuranohydrolase (EC 3.2.1.55) that catalyzes the hydrolysis of terminal non-reducing alpha-L-arabinofuranoside residues in alpha-L-arabinosides. The enzyme acts on alpha-L-arabinofuranosides, alpha-L-arabinans containing (1,3)- and/or (1,5)-linkages, arabinoxylans, and arabinogalactans. Alpha-L-arabinofuranosidase is also known as arabinosidase, alpha-arabinosidase, alpha-L-arabinosidase, alpha-arabinofuranosidase, polysaccharide alpha-L-arabinofuranosidase, alpha-L-arabinofuranoside hydrolase, L-arabinosidase, or alpha-L-arabinanase. Alpha-L-arabinofuranosidase activity can be determined using 5 mg of medium viscosity wheat arabinoxylan (Megazyme International Ireland, Ltd., Bray, Co. Wicklow, Ireland) per ml of 100 mM sodium acetate pH 5 in a total volume of 200 μl for 30 minutes at 40° C. followed by arabinose analysis by AMINEX® HPX-87H column chromatography (Bio-Rad Laboratories, Inc., Hercules, Calif., USA).

Alpha-glucuronidase: The term "alpha-glucuronidase" means an alpha-D-glucosiduronate glucuronohydrolase (EC 3.2.1.139) that catalyzes the hydrolysis of an alpha-D-glucuronoside to D-glucuronate and an alcohol. Alpha-glucuronidase activity can be determined according to de Vries, 1998, *J. Bacteriol.* 180: 243-249. One unit of alpha-glucuronidase equals the amount of enzyme capable of releasing 1 μmole of glucuronic or 4-O-methylglucuronic acid per minute at pH 5, 40° C.

Auxiliary Activity 9 polypeptide: The term "Auxiliary Activity 9 polypeptide" or "AA9 polypeptide" means a polypeptide classified as a lytic polysaccharide monooxygenase (Quinlan et al., 2011, *Proc. Natl. Acad. Sci. USA* 208: 15079-15084; Phillips et al., 2011, *ACS Chem. Biol.* 6: 1399-1406; Lin et al., 2012, *Structure* 20: 1051-1061). AA9 polypeptides were formerly classified into the glycoside hydrolase Family 61 (GH61) according to Henrissat, 1991, *Biochem. J.* 280: 309-316, and Henrissat and Bairoch, 1996, *Biochem. J.* 316: 695-696.

AA9 polypeptides enhance the hydrolysis of a cellulosic material by an enzyme having cellulolytic activity. Cellulolytic enhancing activity can be determined by measuring the increase in reducing sugars or the increase of the total of cellobiose and glucose from the hydrolysis of a cellulosic material by cellulolytic enzyme under the following conditions: 1-50 mg of total protein/g of cellulose in pretreated corn stover (PCS), wherein total protein is comprised of 50-99.5% w/w cellulolytic enzyme protein and 0.5-50% w/w protein of an AA9 polypeptide for 1-7 days at a suitable temperature, such as 40° C.-80° C., e.g., 40° C., 45° C., 50° C., 55° C., 60° C., 65° C., 70° C., 75° C., or 80° C., and a suitable pH, such as 4-9, e.g., 4.0, 4.5, 5.0, 5.5, 6.0, 6.5, 7.0, 7.5, 8.0, 8.5, or 9.0, compared to a control hydrolysis with equal total protein loading without cellulolytic enhancing activity (1-50 mg of cellulolytic protein/g of cellulose in PCS).

AA9 polypeptide enhancing activity can be determined using a mixture of CELLUCLAST® 1.5 L (Novozymes A/S, Bagsvrd, Denmark) and beta-glucosidase as the source of the cellulolytic activity, wherein the beta-glucosidase is present at a weight of at least 2-5% protein of the cellulase protein loading. In one aspect, the beta-glucosidase is an *Aspergillus oryzae* beta-glucosidase (e.g., recombinantly produced in *Aspergillus oryzae* according to WO 02/095014). In another aspect, the beta-glucosidase is an *Aspergillus fumigatus* beta-glucosidase (e.g., recombinantly produced in *Aspergillus oryzae* as described in WO 02/095014).

AA9 polypeptide enhancing activity can also be determined by incubating an AA9 polypeptide with 0.5% phosphoric acid swollen cellulose (PASC), 100 mM sodium acetate pH 5, 1 mM $MnSO_4$, 0.1% gallic acid, 0.025 mg/ml of *Aspergillus fumigatus* beta-glucosidase, and 0.01% TRITON® X-100 (4-(1,1,3,3-tetramethylbutyl)phenyl-polyethylene glycol) for 24-96 hours at 40° C. followed by determination of the glucose released from the PASC.

AA9 polypeptide enhancing activity can also be determined according to WO 2013/028928 for high temperature compositions.

AA9 polypeptides enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

The AA9 polypeptide can also be used in the presence of a soluble activating divalent metal cation according to WO 2008/151043 or WO 2012/122518, e.g., copper.

The AA9 polypeptide can be used in the presence of a dioxy compound, a bicylic compound, a heterocyclic compound, a nitrogen-containing compound, a quinone compound, a sulfur-containing compound, or a liquor obtained from a pretreated cellulosic or hemicellulosic material such as pretreated corn stover (WO 2012/021394, WO 2012/021395, WO 2012/021396, WO 2012/021399, WO 2012/021400, WO 2012/021401, WO 2012/021408, and WO 2012/021410).

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. Beta-glucosidase activity can be determined using p-nitrophenyl-beta-D-glucopyranoside as substrate according to the procedure of Venturi et al., 2002, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20.

Beta-xylosidase: The term "beta-xylosidase" means a beta-D-xyloside xylohydrolase (E.C. 3.2.1.37) that catalyzes the exo-hydrolysis of short beta (1→4)-xylooligosaccharides to remove successive D-xylose residues from non-reducing termini. Beta-xylosidase activity can be determined using 1 mM p-nitrophenyl-beta-D-xyloside as substrate in 100 mM sodium citrate containing 0.01% TWEEN® 20 at pH 5, 40° C. One unit of beta-xylosidase is defined as 1.0 μmole of p-nitrophenolate anion produced per minute at 40° C., pH 5 from 1 mM p-nitrophenyl-beta-D-xyloside in 100 mM sodium citrate containing 0.01% TWEEN® 20.

Catalase: The term "catalase" means a hydrogen-peroxide:hydrogen-peroxide oxidoreductase (EC 1.11.1.6) that catalyzes the conversion of 2 $H_2O_2$ to $O_2$+2 $H_2O$. For purposes of the present invention, catalase activity is determined according to U.S. Pat. No. 5,646,025. One unit of catalase activity equals the amount of enzyme that catalyzes the oxidation of 1 μmole of hydrogen peroxide under the assay conditions.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cellobiohydrolase: The term "cellobiohydrolase" means a 1,4-beta-D-glucan cellobiohydrolase (E.C. 3.2.1.91 and E.C. 3.2.1.176) that catalyzes the hydrolysis of 1,4-beta-D-glucosidic linkages in cellulose, cellooligosaccharides, or any beta-1,4-linked glucose containing polymer, releasing cellobiose from the reducing end (cellobiohydrolase I) or non-reducing end (cellobiohydrolase II) of the chain (Teeri, 1997, *Trends in Biotechnology* 15: 160-167; Teeri et al., 1998, *Biochem. Soc. Trans.* 26: 173-178). Cellobiohydrolase activity can be determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581.

Cellulolytic enzyme, cellulolytic composition, or cellulase: The term "cellulolytic enzyme," "cellulolytic enzyme preparation", "cellulolytic composition", or "cellulase" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic enzyme activity include: (1) measuring the total cellulolytic enzyme activity, and (2) measuring the individual cellulolytic enzyme activities (endoglucanases, cellobiohydrolases, and beta-glucosidases) as reviewed in Zhang et al., 2006, *Biotechnology Advances* 24: 452-481. Total cellulolytic enzyme activity can be measured using insoluble substrates, including Whatman No 1 filter paper, microcrystalline cellulose, bacterial cellulose, algal cellulose, cotton, pretreated lignocellulose, etc. The most common total cellulolytic activity assay is the filter paper assay using Whatman No 1 filter paper as the substrate. The assay was established by the International Union of Pure and Applied Chemistry (IUPAC) (Ghose, 1987, *Pure Appl. Chem.* 59: 257-68).

Cellulolytic enzyme activity can be determined by measuring the increase in production/release of sugars during hydrolysis of a cellulosic material by cellulolytic enzyme(s) under the following conditions: 1-50 mg of cellulolytic enzyme protein/g of cellulose in pretreated corn stover (PCS) (or other pretreated cellulosic material) for 3-7 days at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0, compared to a control hydrolysis without addition of cellulolytic enzyme protein. Typical conditions are 1 ml reactions, washed or unwashed PCS, 5% insoluble solids (dry weight), 50 mM sodium acetate pH 5, 1 mM $MnSO_4$, 50° C., 55° C., or 60° C., 72 hours, sugar analysis by an AMINEX® HPX-87H column (Bio-Rad Laboratories, Inc., Hercules, Calif., USA).

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endoglucanase: The term "endoglucanase" means a 4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3-1,4 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, supra). Endoglucanase activity can also be determined using carboxymethyl cellulose (CMC) as substrate according to the procedure of Ghose, 1987, supra, at pH 5, 40° C.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Feruloyl esterase: The term "feruloyl esterase" means a 4-hydroxy-3-methoxycinnamoyl-sugar hydrolase (EC 3.1.1.73) that catalyzes the hydrolysis of 4-hydroxy-3- methoxycinnamoyl (feruloyl) groups from esterified sugar, which is usually arabinose in natural biomass substrates, to produce ferulate (4-hydroxy-3-methoxycinnamate). Feruloyl esterase (FAE) is also known as ferulic acid esterase, hydroxycinnamoyl esterase, FAE-III, cinnamoyl ester hydrolase, FAEA, cinnAE, FAE-I, or FAE-II. Feruloyl esterase activity can be determined using 0.5 mM p-nitrophenylferulate as substrate in 50 mM sodium acetate pH 5.0. One unit of feruloyl esterase equals the amount of enzyme capable of releasing 1 μmole of p-nitrophenolate anion per minute at pH 5, 25° C.

Fragment: The term "fragment" means a polypeptide having one or more (e.g., several) amino acids absent from the amino and/or carboxyl terminus of a mature polypeptide main; wherein the fragment has enzyme activity. In one aspect, a fragment contains at least 85%, e.g., at least 90% or at least 95% of the amino acid residues of the mature polypeptide of an enzyme.

Hemicellulolytic enzyme, hemicellulolytic composition or hemicellulase: The term "hemicellulolytic enzyme", "hemicellulolytic enzyme preparation," "hemicellulolytic composition" or "hemicellulase" means one or more (e.g., several) enzymes that hydrolyze a hemicellulosic material. See, for example, Shallom and Shoham, 2003, Current Opinion In Microbiology 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, Pure & Appl. Chem. 59: 1739-1752, at a suitable temperature such as 40° C.-80° C., e.g., 50° C., 55° C., 60° C., 65° C., or 70° C., and a suitable pH such as 4-9, e.g., 5.0, 5.5, 6.0, 6.5, or 7.0.

Homologous 3' or 5' region: The term "homologous 3' region" means a fragment of DNA that is identical in sequence or has a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to a region in the genome and when combined with a homologous 5' region can target integration of a piece of DNA to a specific site in the genome by homologous recombination. The term "homologous 5' region" means a fragment of DNA that is identical in sequence to a region in the genome and when combined with a homologous 3' region can target integration of a piece of DNA to a specific site in the genome by homologous recombination. The homologous 5' and 3' regions must be linked in the genome which means they are on the same chromosome and within at least 200 kb of one another.

Homologous flanking region: The term "homologous flanking region" means a fragment of DNA that is identical or has a sequence identity of at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to a region in the genome and is located immediately upstream or downstream of a specific site in the genome into which extracellular DNA is targeted for integration.

Homologous repeat: The term "homologous repeat" means a fragment of DNA that is repeated at least twice in the recombinant DNA introduced into a host cell and which can facilitate the loss of the DNA, i.e., selectable marker that is inserted between two homologous repeats, by homologous recombination. A homologous repeat is also known as a direct repeat.

Host cell: The term "host cell" means any cell type that is susceptible to transformation, transfection, transduction, or the like with a nucleic acid construct or expression vector comprising a polynucleotide encoding a polypeptide. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Mature polypeptide: The term "mature polypeptide" means a polypeptide in its final form following translation and any post-translational modifications, such as N-terminal processing, C-terminal truncation, glycosylation, phosphorylation, etc. For instance, the mature polypeptide may be identified, using, e.g., the SignalP program (Nielsen et al., 1997, Protein Engineering 10: 1-6) that predicts a portion of the amino acid sequence as a signal peptide. As such, the mature polypeptide would be identified as the sequence lacking such predicted signal portion.

In one aspect, the mature polypeptide of a cellobiohydrolase I is amino acids 26 to 532 of SEQ ID NO: 2 based on the SignalP 3.0 program (Bendtsen et al., 2004, J. Mol. Biol. 340: 783-795) that predicts amino acids 1 to 25 of SEQ ID NO: 2 are a signal peptide. In another aspect, the mature polypeptide of a cellobiohydrolase II is amino acids 19 to 464 of SEQ ID NO: 4 based on the SignalP 3.0 program that predicts amino acids 1 to 18 of SEQ ID NO: 4 are a signal peptide. In another aspect, the mature polypeptide of a beta-glucosidase is amino acids 20 to 863 of SEQ ID NO: 6 based on the SignalP 3.0 program that predicts amino acids 1 to 19 of SEQ ID NO: 6 are a signal peptide. In another aspect, the mature polypeptide of an AA9 polypeptide is amino acids 26 to 253 of SEQ ID NO: 8 based on the SignalP 3.0 program that predicts amino acids 1 to 25 of SEQ ID NO: 8 are a signal peptide. In another aspect, the mature polypeptide of a GH10 xylanase is amino acids 21 to 405 of SEQ ID NO: 10 based on the SignalP 3.0 program that predicts amino acids 1 to 20 of SEQ ID NO: 10 are a signal peptide. In another aspect, the mature polypeptide of a beta-xylosidase is amino acids 22 to 796 of SEQ ID NO: 12 based on the SignalP 3.0 program that predicts amino acids 1 to 21 of SEQ ID NO: 12 are a signal peptide. In another aspect, the mature polypeptide of an endoglucanase I is amino acids 23 to 459 of SEQ ID NO: 14 based on the SignalP 3.0 program that predicts amino acids 1 to 22 of SEQ ID NO: 14 are a signal peptide. In another aspect, the mature polypeptide of an endoglucanase II is amino acids 22 to 418 of SEQ ID NO: 16 based on the SignalP 3.0 program that predicts amino acids 1 to 21 of SEQ ID NO: 16 are a signal peptide. In another aspect, the mature polypeptide of a beta-glucosidase variant is amino acids 20 to 863 of SEQ ID NO: 18 based on the SignalP 3.0 program that predicts amino acids 1 to 19 of SEQ ID NO: 18 are a signal peptide. In another aspect, the mature polypeptide of a GH10 xylanase is amino acids 20 to 397 of SEQ ID NO: 20 based on the SignalP 3.0 program that predicts amino acids 1 to 19 of SEQ ID NO: 20 are a signal peptide. In another aspect, the mature polypeptide of a beta-xylosidase is amino acids 21 to 792 of SEQ ID NO: 22 based on the SignalP 3.0 program that predicts amino acids 1 to 20 of SEQ ID NO: 22 are a signal peptide. In another aspect, the mature polypeptide of a catalase is amino acids 17 to 740 of SEQ ID NO: 24 based on the SignalP 3.0 program that predicts amino acids 1 to 16 of SEQ ID NO: 24 are a signal peptide. In another aspect, the mature polypeptide of a cellobiohydrolase I is amino acids 27 to 532 of SEQ ID NO: 26 based on the SignalP 3.0 program that predicts amino acids 1 to 26 of SEQ ID NO: 26 are a signal peptide. In another aspect, the mature polypeptide of a cellobiohydrolase II is amino acids 20 to 454 of SEQ ID NO: 28 based on the SignalP 3.0 program that predicts amino acids 1 to 19 of SEQ ID NO: 28 are a signal peptide. In another aspect, the mature polypeptide of an AA9 is amino acids 19 to 226 of SEQ ID NO: 30 based on the SignalP 3.0 program that predicts amino acids 1 to 18 of SEQ ID NO: 30 are a signal peptide.

It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having enzyme activity.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent Enzyme: The term "parent" means an enzyme to which an alteration is made to produce a variant. The parent may be a naturally occurring (wild-type) polypeptide or a variant thereof.

Pretreated cellulosic or hemicellulosic material: The term "pretreated cellulosic or hemicellulosic material" means a cellulosic or hemicellulosic material derived from biomass by treatment with heat and dilute sulfuric acid, alkaline pretreatment, neutral pretreatment, or any pretreatment known in the art.

Pretreated corn stover: The term "Pretreated Corn Stover" or "PCS" means a cellulosic material derived from corn stover by treatment with heat and dilute sulfuric acid, alkaline pretreatment, neutral pretreatment, or any pretreatment known in the art.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of
Alignment–Total Number of Gaps in Alignment)

Solid-Liquid Separation: Solid-liquid separation may be achieved in any way, including using a screw press, centrifugation, belt press, drum filter, hydrocyclone and/or filter press, or any kind of apparatus which can handle solid/liquid separation, including gravity-fed systems or apparatuses.

Subsequence: The term "subsequence" means a polynucleotide having one or more (e.g., several) nucleotides absent from the 5' and/or 3' end of a mature polypeptide coding sequence, wherein the subsequence encodes a fragment having enzyme activity. In one aspect, a subsequence contains at least 85%, e.g., at least 90% or at least 95% of the nucleotides of the mature polypeptide coding sequence of an enzyme.

Transformant: The term "transformant" means a cell which has taken up extracellular DNA (foreign, artificial or modified) and expresses the gene(s) contained therein.

Transformation: The term "transformation" means the introduction of extracellular DNA into a cell, i.e., the genetic alteration of a cell resulting from the direct uptake, incorporation and expression of exogenous genetic material (exogenous DNA) from its surroundings and taken up through the cell membrane(s).

Variant: The term "variant" means a polypeptide having enzyme or enzyme enhancing activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

Whole broth preparation: The term "whole broth preparation" means a composition produced by a naturally-occurring source, i.e., a naturally-occurring microorganism that is unmodified with respect to the cellulolytic and/or hemicellulolytic enzymes produced by the naturally-occurring microorganism, or a non-naturally-occurring source, i.e., a non-naturally-occurring microorganism, e.g., mutant, that is unmodified with respect to the cellulolytic and/or hemicellulolytic enzymes produced by the non-naturally-occurring microorganism.

Wild-Type Enzyme: The term "wild-type" enzyme means an enzyme expressed by a naturally occurring microorganism, such as a bacterium, yeast, or filamentous fungus found in nature.

Xylan-containing material: The term "xylan-containing material" means any material comprising a plant cell wall polysaccharide containing a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino)glucuronoxylans, (glucurono)arabinoxylans, arabinoxylans, and complex heteroxylans. See, for example, Ebringerova et al., 2005, *Adv. Polym. Sci.* 186: 1-67.

In processes of the present invention, any material containing xylan may be used. In a preferred aspect, the xylan-containing material is lignocellulose.

Xylan degrading activity or xylanolytic activity: The term "xylan degrading activity" or "xylanolytic activity" means a biological activity that hydrolyzes xylan-containing material. The two basic approaches for measuring xylanolytic activity include: (1) measuring the total xylanolytic activity, and (2) measuring the individual xylanolytic activities (e.g., endoxylanases, beta-xylosidases, arabinofuranosidases, alpha-glucuronidases, acetylxylan esterases, feruloyl esterases, and alpha-glucuronyl esterases). Recent progress in assays of xylanolytic enzymes was summarized in several publications including Biely and Puchard, 2006, *Journal of the Science of Food and Agriculture* 86(11): 1636-1647; Spanikova and Biely, 2006, *FEBS Letters* 580(19): 4597-4601; Herrmann et al., 1997, *Biochemical Journal* 321: 375-381.

Total xylan degrading activity can be measured by determining the reducing sugars formed from various types of xylan, including, for example, oat spelt, beechwood, and larchwood xylans, or by photometric determination of dyed xylan fragments released from various covalently dyed xylans. A common total xylanolytic activity assay is based on production of reducing sugars from polymeric 4-O-methyl glucuronoxylan as described in Bailey et al., 1992, Interlaboratory testing of methods for assay of xylanase activity, *Journal of Biotechnology* 23(3): 257-270. Xylanase activity can also be determined with 0.2% AZCL-arabinoxylan as substrate in 0.01% TRITON® X-100 and 200 mM sodium phosphate pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6.

Xylan degrading activity can be determined by measuring the increase in hydrolysis of birchwood xylan (Sigma Chemical Co., Inc., St. Louis, Mo., USA) by xylan-degrading enzyme(s) under the following typical conditions: 1 ml reactions, 5 mg/ml substrate (total solids), 5 mg of xylanolytic protein/g of substrate, 50 mM sodium acetate pH 5, 50° C., 24 hours, sugar analysis using p-hydroxybenzoic acid hydrazide (PHBAH) assay as described by Lever, 1972, *Anal. Biochem.* 47: 273-279.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. Xylanase activity can be determined with 0.2% AZCL-arabinoxylan as substrate in 0.01% TRITON® X-100 and 200 mM sodium phosphate pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6.

Reference to "about" a value or parameter herein includes aspects that are directed to that value or parameter per se. For example, description referring to "about X" includes the aspect "X".

As used herein and in the appended claims, the singular forms "a," "or," and "the" include plural referents unless the context clearly dictates otherwise. It is understood that the aspects of the invention described herein include "consisting" and/or "consisting essentially of" aspects.

Unless defined otherwise or clearly indicated by context, all technical and scientific terms used herein have the same meaning as commonly understood by one of ordinary skill in the art to which this invention belongs.

DETAILED DESCRIPTION

Figure 1:
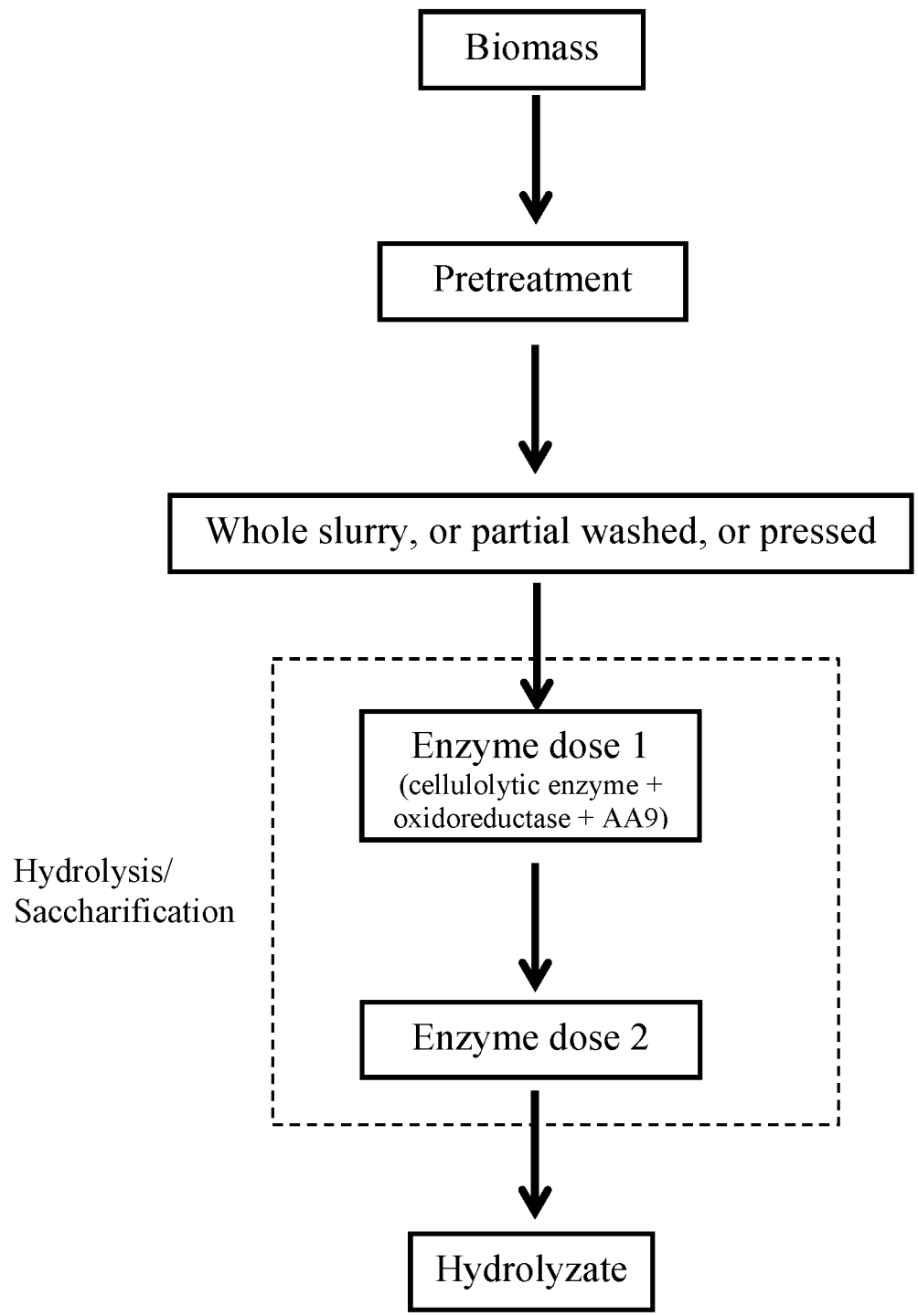
FIG. 1 is a flowchart illustrating a general process scheme of the invention, where dose 1 is an enzyme composition comprising one or more cellulolytic enzymes and at least one of an oxidoreductase and an AA9 (GH61) polypeptide having cellulolytic enhancing activity and dose 2 is an enzyme composition comprising cellulases.

Described herein are processes for improving the sugar yield from a hydrolysis process comprising administration of enzymes for hydrolysis as at least two different enzyme compositions in at least two different stages of hydrolysis. Further described are processes of multi-stage hydrolysis and processes of fermentation incorporating such improved sugar yield processes. Also described are enzyme compositions suitable for use in the processes and/or methods described herein.

The present inventors have surprisingly found that by conducting hydrolysis in at least two stages, a first stage comprising contacting a pretreated lignocellulose-containing material with a first enzyme composition comprising one or more cellulolytic enzymes and at least one of an oxidoreductase and an AA9 (GH61) polypeptide having cellulolytic enhancing activity, followed by a latter stage in which a second enzyme composition comprising cellulases is added, the overall hydrolysis yield can be increased. In another embodiment, the first enzyme composition comprises at least a catalase.

Increase of the yield is achieved as compared to the yield obtained from an equivalent process not utilizing a multi-stage process as described herein. In one embodiment the yield is increased relative to a process in which all enzymes for enzymatic hydrolysis are added in a single stage. In another embodiment the yield is increased relative to a process in which all enzymes for enzymatic hydrolysis are blended prior to administration in a single-stage hydrolysis. In still another embodiment the yield is increased relative to a process in which all enzymes for enzymatic hydrolysis are added in a constant feed in a single-stage hydrolysis. In a further embodiment the yield is increased such that a lower total enzyme dose can be used to achieve a same yield relative to the enzyme dose required in an equivalent process not utilizing a multi-stage process as described herein.

The first and second enzyme compositions are different from one another. As used herein, "different" refers to a first enzyme composition and a second enzyme composition that are not the same as one another. The first enzyme composition and the second enzyme composition may be comprised of different enzymes and/or may comprise different amounts of components. Both the first and second enzyme compositions have hydrolytic activity on the cellulosic substrate. In an embodiment the first enzyme composition comprises an oxidoreductase and an AA9 (GH61) polypeptide having cellulolytic enhancing activity. In a further embodiment the first enzyme composition comprises a catalase and an AA9 (GH61) polypeptide having cellulolytic enhancing activity. In a still further embodiment the first enzyme composition comprises at least a catalase. In a still further embodiment the first enzyme composition comprises at least an AA9 (GH61) polypeptide having cellulolytic enhancing activity.

Taken together, the first and second enzyme compositions provide up to about 100% of the total enzymes added during enzymatic hydrolysis. In an embodiment the first enzyme composition provides about 1 to about 99%, e.g., about 10% to about 90%, about 40% to about 80%, about 50% to about 70% of the total enzyme protein added in hydrolysis.

Cellulosic Material

Processes of the present invention are carried out using cellulosic material. The term "cellulosic material" means any material containing cellulose. The predominant polysaccharide in the primary cell wall of biomass is cellulose, the second most abundant is hemicellulose, and the third is pectin. The secondary cell wall, produced after the cell has stopped growing, also contains polysaccharides and is strengthened by polymeric lignin covalently cross-linked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix.

Cellulose is generally found, for example, in the stems, leaves, hulls, husks, and cobs of plants or leaves, branches, and wood of trees. The cellulosic material may be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred embodiment, the cellulosic material is any biomass material. In another preferred embodiment the cellulosic material is lignocellulose-containing biomass material. In another preferred embodiment, the cellulosic material is lignocellulose, which comprises cellulose, hemicelluloses, and lignin.

In an embodiment, the cellulosic material is agricultural residue, herbaceous material (including energy crops), municipal solid waste, pulp and paper mill residue, waste paper, or wood (including forestry residue).

In another embodiment, the cellulosic material is *arundo*, bagasse, bamboo, corn cob, corn fiber, corn stover, *miscanthus*, rice straw, switchgrass, or wheat straw.

In one embodiment, the cellulosic material is fiber, such as corn fiber or wheat fiber. Fiber, such as corn or wheat fiber, may be obtained by fractionation. Fractionation technologies are well-known in the art. In one embodiment the cellulosic material is fiber obtained from dry fractionation processes. In one embodiment the cellulosic material is fiber obtained from wet fractionation processes.

In another embodiment, the cellulosic material is aspen, *eucalyptus*, fir, pine, poplar, spruce, or willow.

In another embodiment, the cellulosic material is algal cellulose, bacterial cellulose, cotton linter, filter paper, microcrystalline cellulose (e.g., AVICEL®), or phosphoric-acid treated cellulose.

In another embodiment, the cellulosic material is an aquatic biomass. As used herein the term "aquatic biomass" means biomass produced in an aquatic environment by a photosynthesis process. The aquatic biomass may be algae, emergent plants, floating-leaf plants, or submerged plants.

The cellulosic material may be used as is or may be subjected to pretreatment, using conventional methods known in the art, as described more fully herein. In a preferred embodiment, the cellulosic material is pretreated.

Hemicellulosic Material

The term "hemicellulosic material" means any material comprising hemicelluloses. Hemicelluloses include xylan, glucuronoxylan, arabinoxylan, glucomannan, and xyloglucan. These polysaccharides contain many different sugar monomers. Sugar monomers in hemicellulose can include xylose, mannose, galactose, rhamnose, and arabinose. Hemicelluloses contain most of the D-pentose sugars. Xylose is in most cases the sugar monomer present in the largest amount, although in softwoods mannose can be the most abundant sugar. Xylan contains a backbone of beta-(1-4)-linked xylose residues. Xylans of terrestrial plants are heteropolymers possessing a beta-(1-4)-D-xylopyranose backbone, which is branched by short carbohydrate chains. They comprise D-glucuronic acid or its 4-O-methyl ether, L-arabinose, and/or various oligosaccharides, composed of D-xylose, L-arabinose, D- or L-galactose, and D-glucose. Xylan-type polysaccharides can be divided into homoxylans and heteroxylans, which include glucuronoxylans, (arabino) glucuronoxylans, (glucurono)arabinoxylans, arabinoxylans, and complex heteroxylans. See, for example, Ebringerova et al., 2005, Adv. Polym. Sci. 186: 1-67. Hemicellulosic material is also known herein as "xylan-containing material".

Sources for hemicellulosic material are essentially the same as those for cellulosic material described herein. It is understood herein that the hemicellulose may be in the form of lignocellulose, a plant cell wall material containing lignin, cellulose, and hemicellulose in a mixed matrix. In a preferred embodiment, the hemicellulosic material is any biomass material. In another preferred embodiment, the hemicellulosic material is lignocellulose, which comprises cellulose, hemicelluloses, and lignin.

Pretreatment of Cellulosic Material

In practicing the processes of the present invention, the cellulosic material used may be pretreated by any pretreatment process known in the art, used to disrupt plant cell wall components of cellulosic or hemicellulosic material (Chandra et al., 2007, *Adv. Biochem. Engin./Biotechnol.* 108: 67-93; Galbe and Zacchi, 2007, *Adv. Biochem. Engin./Biotechnol.* 108: 41-65; Hendriks and Zeeman, 2009, *Bioresource Technology* 100: 10-18; Mosier et al., 2005, *Bioresource Technology* 96: 673-686; Taherzadeh and Karimi, 2008, *Int. J. Mol. Sci.* 9: 1621-1651; Yang and Wyman, 2008, *Biofuels Bioproducts and Biorefining-Biofpr.* 2: 26-40).

The cellulosic or hemicellulosic material may also be subjected to particle size reduction, sieving, pre-soaking, wetting, washing, and/or conditioning prior to or with additional pretreatment methods, using methods known in the art or as otherwise described herein.

Conventional pretreatments include, but are not limited to, steam pretreatment (with or without explosion), dilute acid pretreatment, hot water pretreatment, alkaline pretreatment, lime pretreatment, wet oxidation, wet explosion, ammonia fiber explosion, organosolv pretreatment, and biological pretreatment. Additional pretreatments include ammonia percolation, ultrasound, electroporation, microwave, supercritical $CO_2$, supercritical $H_2O$, ozone, ionic liquid, and gamma irradiation pretreatments.

In an embodiment the cellulosic or hemicellulosic material is pretreated before hydrolysis and/or fermentation. Pretreatment is preferably performed prior to the hydrolysis. Alternatively, the pretreatment can be carried out simultaneously with enzyme hydrolysis to release fermentable sugars, such as glucose, xylose, and/or cellobiose. In most cases the pretreatment step itself results in some conversion of biomass to fermentable sugars (even in absence of enzymes).

Steam Pretreatment. In steam pretreatment, the cellulosic or hemicellulosic material is heated to disrupt the plant cell wall components, including lignin, hemicellulose, and cellulose to make the cellulose and other fractions, e.g., hemicellulose, accessible to enzymes. The cellulosic material is passed to or through a reaction vessel where steam is injected to increase the temperature to the required temperature and pressure and is retained therein for the desired reaction time. Steam pretreatment is preferably performed at 140-250° C., e.g., 160-200° C. or 170-190° C., where the optimal temperature range depends on optional addition of a chemical catalyst. Residence time for the steam pretreatment is preferably 1-60 minutes, e.g., 1-30 minutes, 1-20 minutes, 3-12 minutes, or 4-10 minutes, where the optimal residence time depends on the temperature and optional addition of a chemical catalyst. Steam pretreatment allows for relatively high solids loadings, so that the cellulosic material is generally only moist during the pretreatment. The steam pretreatment is often combined with an explosive discharge of the material after the pretreatment, which is known as steam explosion, that is, rapid flashing to atmospheric pressure and turbulent flow of the material to increase the accessible surface area by fragmentation (Duff and Murray, 1996, *Bioresource Technology* 855: 1-33; Galbe and Zacchi, 2002, *Appl. Microbiol. Biotechnol.* 59: 618-628; U.S. Patent Application No. 2002/0164730). During steam pretreatment, hemicellulose acetyl groups are cleaved and the resulting acid autocatalyzes partial hydrolysis of the hemicellulose to monosaccharides and oligosaccharides. Lignin is removed to only a limited extent.

Chemical Pretreatment: The term "chemical pretreatment" refers to any chemical pretreatment that promotes the separation and/or release of cellulose, hemicellulose, and/or lignin. Such a pretreatment may convert crystalline cellulose to amorphous cellulose. Examples of suitable chemical pretreatment processes include, for example, dilute acid pretreatment, lime pretreatment, wet oxidation, ammonia fiber/freeze expansion (AFEX), ammonia percolation (APR), ionic liquid, and organosolv pretreatments.

A chemical catalyst such as $H_2SO_4$ or $SO_2$ (typically 0.3 to 5% w/w) is sometimes added prior to steam pretreatment, which decreases the time and temperature, increases the recovery, and improves enzymatic hydrolysis (Ballesteros et al., 2006, *Appl. Biochem. Biotechnol.* 129-132: 496-508; Varga et al., 2004, *Appl. Biochem. Biotechnol.* 113-116: 509-523; Sassner et al., 2006, *Enzyme Microb. Technol.* 39: 756-762). In dilute acid pretreatment, the cellulosic material is mixed with dilute acid, typically $H_2SO_4$, and water to form a slurry, heated by steam to the desired temperature, and after a residence time flashed to atmospheric pressure. The dilute acid pretreatment may be performed with a number of reactor designs, e.g., plug-flow reactors, counter-current reactors, or continuous counter-current shrinking bed reactors (Duff and Murray, 1996, supra; Schell et al., 2004, *Bioresource Technology* 91: 179-188; Lee et al., 1999, *Adv. Biochem. Eng. Biotechnol.* 65: 93-115).

Several methods of pretreatment under alkaline conditions may also be used. These alkaline pretreatments include, but are not limited to, sodium hydroxide, lime, wet oxidation, ammonia percolation (APR), and ammonia fiber/freeze expansion (AFEX) pretreatment.

Lime pretreatment is performed with calcium oxide or calcium hydroxide at temperatures of 85-150° C. and residence times from 1 hour to several days (Wyman et al., 2005, *Bioresource Technology* 96: 1959-1966; Mosier et al., 2005, supra). WO 2006/110891, WO 2006/110899, WO 2006/110900, and WO 2006/110901 disclose pretreatment methods using ammonia.

Wet oxidation is a thermal pretreatment performed typically at 180-200° C. for 5-15 minutes with addition of an oxidative agent such as hydrogen peroxide or over-pressure of oxygen (Schmidt and Thomsen, 1998, *Bioresource Technology* 64: 139-151; Palonen et al., 2004, *Appl. Biochem. Biotechnol.* 117: 1-17; Varga et al., 2004, *Biotechnol. Bioeng.* 88: 567-574; Martin et al., 2006, *J. Chem. Technol. Biotechnol.* 81: 1669-1677). The pretreatment is performed preferably at 1-40% dry matter, e.g., 2-30% dry matter or 5-20% dry matter, and often the initial pH is increased by the addition of alkali such as sodium carbonate.

A modification of the wet oxidation pretreatment method, known as wet explosion (combination of wet oxidation and steam explosion) can handle dry matter up to 30%. In wet explosion, the oxidizing agent is introduced during pretreatment after a certain residence time. The pretreatment is then ended by flashing to atmospheric pressure (WO 2006/032282).

Ammonia fiber expansion (AFEX) involves treating the cellulosic material with liquid or gaseous ammonia at moderate temperatures such as 90-150° C. and high pressure such as 17-20 bar for 5-10 minutes, where the dry matter content can be as high as 60% (Gollapalli et al., 2002, *Appl. Biochem. Biotechnol.* 98: 23-35; Chundawat et al., 2007, *Biotechnol. Bioeng.* 96: 219-231; Alizadeh et al., 2005, *Appl. Biochem. Biotechnol.* 121: 1133-1141; Teymouri et al., 2005, *Bioresource Technology* 96: 2014-2018). During AFEX pretreatment cellulose and hemicelluloses remain relatively intact. Lignin-carbohydrate complexes are cleaved.

Organosolv pretreatment delignifies the cellulosic material by extraction using aqueous ethanol (40-60% ethanol) at 160-200° C. for 30-60 minutes (Pan et al., 2005, *Biotechnol. Bioeng.* 90: 473-481; Pan et al., 2006, *Biotechnol. Bioeng.* 94: 851-861; Kurabi et al., 2005, *Appl. Biochem. Biotechnol.* 121: 219-230). Sulphuric acid is usually added as a catalyst. In organosolv pretreatment, the majority of hemicellulose and lignin is removed.

Other examples of suitable pretreatment methods are described by Schell et al., 2003, *Appl. Biochem. Biotechnol.* 105-108: 69-85, and Mosier et al., 2005, supra, and U.S. Published Application 2002/0164730.

In one embodiment, the chemical pretreatment is preferably carried out as a dilute acid treatment, and more preferably as a continuous dilute acid treatment. The acid is typically sulfuric acid, but other acids may also be used, such as acetic acid, citric acid, nitric acid, phosphoric acid, tartaric acid, succinic acid, hydrogen chloride, or mixtures thereof. Mild acid treatment is conducted in the pH range of preferably 1-5, e.g., 1-4 or 1-2.5. In one embodiment, the acid concentration is in the range from preferably 0.01 to 10 wt. % acid, e.g., 0.05 to 5 wt. % acid or 0.1 to 2 wt. % acid. The acid is contacted with the cellulosic material and held at a temperature in the range of preferably 140-200° C., e.g., 165-190° C., for periods ranging from 1 to 60 minutes.

In another embodiment, pretreatment takes place in an aqueous slurry. In preferred embodiments, the cellulosic material is present during pretreatment in amounts preferably between 10-80 wt. %, e.g., 20-70 wt. % or 30-60 wt. %, such as around 40 wt. %. The pretreated cellulosic material may be unwashed or washed using any method known in the art, e.g., washed with water.

Mechanical Pretreatment or Physical Pretreatment: The term "mechanical pretreatment" or "physical pretreatment" refers to any pretreatment that promotes size reduction of particles. For example, such pretreatment may involve various types of grinding or milling (e.g., dry milling, wet milling, or vibratory ball milling).

The cellulosic material may be pretreated both physically (mechanically) and chemically. Mechanical or physical pretreatment may be coupled with steaming/steam explosion, hydrothermolysis, dilute or mild acid treatment, high temperature, high pressure treatment, irradiation (e.g., microwave irradiation), or combinations thereof. In one embodiment, high pressure means pressure in the range of preferably about 100 to about 400 psi, e.g., about 150 to about 250 psi. In another embodiment, high temperature means temperature in the range of about 100 to about 300° C., e.g., about 140 to about 200° C. In a preferred embodiment, mechanical or physical pretreatment is performed in a batch-process using a steam gun hydrolyzer system that uses high pressure and high temperature as defined above, e.g., a Sunds Hydrolyzer available from Sunds Defibrator AB, Sweden. The physical and chemical pretreatments may be carried out sequentially or simultaneously, as desired.

Accordingly, in a preferred embodiment, the cellulosic material is subjected to physical (mechanical) or chemical pretreatment, or any combination thereof, to promote the separation and/or release of cellulose, hemicellulose, and/or lignin.

Biological Pretreatment: The term "biological pretreatment" refers to any biological pretreatment that promotes the separation and/or release of cellulose, hemicellulose, and/or lignin from the cellulosic material. Biological pretreatment techniques may involve applying lignin-solubilizing microorganisms and/or enzymes (see, for example, Hsu, T.-A., 1996, Pretreatment of biomass, in *Handbook on Bioethanol: Production and Utilization*, Wyman, C. E., ed., Taylor & Francis, Washington, D.C., 179-212; Ghosh and Singh, 1993, *Adv. Appl. Microbiol.* 39: 295-333; McMillan, J. D., 1994, Pretreating lignocellulosic biomass: a review, in *Enzymatic Conversion of Biomass for Fuels Production*, Himmel, M. E., Baker, J. O., and Overend, R. P., eds., ACS Symposium Series 566, American Chemical Society, Washington, D.C., chapter 15; Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Olsson and Hahn-Hagerdal, 1996, *Enz. Microb. Tech.* 18: 312-331; and Vallander and Eriksson, 1990, *Adv. Biochem. Eng./Biotechnol.* 42: 63-95).

Hydrolysis (Saccharification)

In hydrolysis, the cellulosic material, e.g., pretreated lignocellulose, is hydrolyzed to break down cellulose and/or hemicellulose to fermentable sugars, such as glucose, cellobiose, xylose, xylulose, arabinose, mannose, galactose, and/or soluble oligosaccharides. In processes described herein, hydrolysis is performed enzymatically by two or more enzyme compositions administered in two or more stages.

In conversion of biomass substrates to ethanol and other fuels, particularly in large scale operations, many factors may limit the resultant yield. Specifically addressing such limitations may allow an increase in yield from hydrolysis and, subsequently, fermentation.

While it is desirable in saccharification to provide efficient conversion of biomass to fermentable sugars, simply increasing the solids loading does not always produce a corresponding increase in converted product. In fact, as the solids loading is increased, a decrease in enzymatic digestion is generally observed. Such decrease may be attributable to factors such as increased viscosity, difficulty of maintaining enzyme distribution, and increased generation of inhibitors.

In large scale biomass processing, handling of high solids is necessary. However, attempting to process high solids in a batchwise manner will result in a high viscosity, which may result in a slurry that is difficult to pump or stir or otherwise requiring additional means for handling. One method of addressing viscosity has been to operate in a continuous or semi-continuous manner in which the substrate and/or enzymes are fed to a reactor, continuously or periodically.

Inhibitors may provide a further hurdle in achieving high yields. Known inhibitors may include, but are not limited to, phenolics, sugar monomers, sugar oligomers, xylooligomers, acids (e.g., acetic acid), and degradation products.

Various methods of pretreatment or detoxification have been shown to individually address inhibitors in pretreated biomass. It has been shown that use of phenol oxidizing enzymes in a detoxification process (WO2008/134259) or in combination with hemicellulases (WO2013/148504) can reduce inhibition of hydrolysis.

It has further been shown that pretreatment with a GH61 polypeptide (WO 2012/061517) can decrease the recalcitrance of cellulosic material to enzyme hydrolysis.

The inventors have surprisingly discovered that by using a multi-stage hydrolysis with administration of enzymes in at least two separate doses, hydrolysis yields can be increased, without requiring large amounts of total enzyme protein.

Processing of cellulosic material according to the present invention can be implemented using any conventional biomass processing apparatus configured to operate in accordance with embodiments of the invention.

A conventional apparatus can include a fed-batch stirred reactor, a batch stirred reactor, a continuous flow stirred reactor with ultrafiltration, and/or a continuous plug-flow column reactor (de Castilhos Corazza et al., 2003, *Acta Scientiarum. Technology* 25: 33-38; Gusakov and Sinitsyn, 1985, *Enz. Microb. Technol.* 7: 346-352), an attrition reactor (Ryu and Lee, 1983, *Biotechnol. Bioeng.* 25: 53-65). Additional reactor types include fluidized bed, upflow blanket, immobilized, and extruder type reactors for hydrolysis and/or fermentation.

The hydrolysis can be carried out as a batch process or series of batch processes. The hydrolysis can be carried out as a batch or continuous process, or series of batch or series of continuous processes, where the cellulosic or hemicellulosic material is fed gradually to, for example, an enzyme-containing hydrolysis solution. The hydrolysis may also be carried out as a series of batch and continuous processes.

Operation of multiple reactors in series allows for closer control of elements within each reactor, e.g., temperature, pH, mixing, concentration, and the like. Therefore in an embodiment of the invention comprising a multi-stage hydrolysis, at least two stages are carried out in separate reactors. In a preferred embodiment, each stage of a multi-stage hydrolysis is carried out in a separate reactor. In a further preferred embodiment, at least one stage in a multi-stage hydrolysis is carried out in a continuously operating reactor (e.g., CSTR). In a still further preferred embodiment, a continuous reactor in a multi-stage hydrolysis process is a continuously stirred tank reactor (CSTR) reactor, in series with at least one additional reactor. In another preferred embodiment, a continuously stirred reactor is followed in series with at least one additional reactor. In yet another preferred embodiment, a continuously stirred reactor is followed in series by at least one batch reactor.

Continuous operation, such as in use of a CSTR, provides advantages of continuous production and a steady state of operation once the reactor is running. Use of a continuous reactor permits management of high viscosity unhydrolyzed substrate, which also permits operation with higher total solids than might be available in a batch reactor. Semi-batch and semi-continuous operation may permit control of environmental conditions and provide additional flexibility, compared to pure batch processes for selection of optimal conditions. For large scale hydrolysis processes, continuous operation is often preferred to eliminate downtime and to maximize production, though semi-batch and semi-continuous operation may also be used.

The present inventors have discovered that improved hydrolysis yields can be achieved through administration of enzymes in at least two separate doses in a multi-stage hydrolysis. Such improvement is achieved while keeping enzyme loading low.

As described herein, hydrolysis of cellulosic material is performed enzymatically by two or more enzyme compositions in two or more stages of hydrolysis. In an embodiment the invention provides processes including multi-stage hydrolysis comprising a first stage of hydrolysis comprising adding enzymes to initiate hydrolysis while reducing inhibitors and/or reducing viscosity or otherwise increasing the susceptibility of the cellulosic material to further enzymatic hydrolysis and a second stage of hydrolysis comprising adding additional hydrolyzing enzymes, where the enzyme composition added in the first stage differs from the enzyme composition added in the second stage. In an embodiment, such multi-stage processes are sufficient to improve or increase sugar yields as compared to yields from a process that does not use a multi-stage enzyme administration.

In an embodiment of the invention, processes of the invention include a first stage hydrolysis comprising administration of a first enzyme composition, where the enzyme activity is sufficient to reduce the inhibitors, e.g., phenolics, as compared to the inhibitors present in a pretreated lignocellulosic material not subjected to such a first step of hydrolysis. In a further embodiment, the enzyme activity of the first enzyme composition is sufficient to reduce the viscosity as compared to the viscosity of a pretreated lignocellulosic material not subjected to such a first step of hydrolysis. In a still further embodiment, the enzyme activity of the first enzyme composition is sufficient to increase the susceptibility of the cellulosic material to additional enzymatic hydrolysis in a subsequent stage. In yet another embodiment, the enzyme activity of the first enzyme composition is sufficient to saccharify at least a portion of the cellulosic material, to result in production of fermentable sugars.

Processes of the invention further comprise a subsequent (e.g., second) stage of hydrolysis, comprising administration of one or more cellulases, where such administration is sufficient to saccharify at least a portion of the product of the first stage of hydrolysis, to result in production of fermentable sugars.

The present invention therefore relates to processes of multi-stage hydrolysis of a lignocellulosic material, the process comprising: a) a step of contacting a lignocellulosic material with a first enzyme composition comprising one or more cellulolytic enzymes and at least one of an oxidoreductase and an AA9 (GH61) polypeptide having cellulolytic enhancing activity; and b) a saccharification step comprising combining the material of step a) with a second enzyme composition comprising one or more cellulases, wherein the first enzyme composition and the second enzyme composition are different enzyme compositions and wherein the process provides increased glucose yield compared to administration of enzymes in a single stage hydrolysis. In one embodiment, the processes further comprise recovering the hydrolyzate. Soluble products of degradation of the cellulosic material can be separated from insoluble cellulosic material using a method known in the art such as, for example, centrifugation, filtration, or gravity settling. In an embodiment the first enzyme composition is added in a first stage of hydrolysis and the second enzyme composition is added in a later (e.g., second) stage of hydrolysis. In a further embodiment, the stages of hydrolysis are conducted at a pH independently selected from about 4.0 to about 5.5. In a still further embodiment, the first stage of hydrolysis is conducted at a different pH than the second stage of hydrolysis. In another embodiment, the stages of hydrolysis are conducted at a temperature independently selected from about 40° C. to about 60° C. In still another embodiment, the second enzyme composition is added at least about 1 hour to about 24 hours following contacting of the lignocellulosic material and the first enzyme composition.

The present invention still further relates to processes of increasing a sugar yield of hydrolysis of a lignocellulosic material, the process comprising: a) a step of contacting a lignocellulosic material with a first enzyme composition comprising one or more cellulolytic enzymes and at least one of an oxidoreductase and an AA9 (GH61) polypeptide having cellulolytic enhancing activity; and b) a saccharification step comprising combining the material of step a) with a second enzyme composition comprising one or more cellulases, wherein the first enzyme composition and the second enzyme composition are different enzyme compositions and wherein the process provides increased sugar yield compared to administration of enzymes in a single stage hydrolysis. In an embodiment the first enzyme composition is added in a first stage of hydrolysis and the second enzyme composition is added in a later (e.g., second) stage of hydrolysis. In a further embodiment, the stages of hydrolysis are conducted at a pH independently selected from about 4.0 to about 5.5. In a still further embodiment, the first stage of hydrolysis is conducted at a different pH than the second stage of hydrolysis. In another embodiment, the stages of hydrolysis are conducted at a temperature independently selected from about 40° C. to about 60° C. In still another embodiment, the second enzyme composition is added at least about 1 hour to about 24 hours following contacting of the lignocellulosic material and the first enzyme composition. In another embodiment the increased sugar yield is increased glucose or increased xylose.

Enzymatic hydrolysis (i.e., saccharification) is preferably carried out in a suitable aqueous environment under conditions that may be readily determined by one skilled in the art. In one embodiment, hydrolysis is performed under conditions suitable for the activity of the enzyme composition, preferably optimal for the enzyme composition.

The hydrolysis is generally performed in stirred-tank reactors or fermentors under controlled pH, dissolved oxygen (DO) levels, temperature, and mixing conditions. Suitable process time, temperature, DO levels, and pH conditions may readily be determined by one skilled in the art.

As used herein "multi-stage hydrolysis" or "multi-stage saccharification" refers to a hydrolysis performed in two or more stages. Stages of hydrolysis may include, but are not limited to, use of one or more reactors, variations in temperature during the hydrolysis process, variations in pH during the hydrolysis process, variations in DO levels during the hydrolysis process, variations in mixing or stirring, variations in timing (e.g., length of time of each stage) during the hydrolysis process, and variations of enzyme addition during the hydrolysis process. In various embodiments of the invention, stages of hydrolysis may comprise one or more of: different reactors, different temperatures, different pH, different dissolved oxygen (DO) levels, different mixing/stirring, and administration of different enzyme compositions.

For example, the hydrolysis may last up to 200 hours, but is typically performed for preferably about 12 to about 120 hours, e.g., about 16 to about 72 hours or about 24 to about 48 hours. In an embodiment of the invention a first stage of hydrolysis is carried out for about 3 to about 30 hours, e.g., about 15 to about 30 hours. In another embodiment of the invention a second stage of hydrolysis is carried out for about 45 to about 100 hours, e.g., about 50 to about 72 hours.

The hydrolysis temperature is in the range of preferably about 25° C. to about 70° C., e.g., about 30° C. to about 65° C., about 40° C. to about 60° C., or about 50° C. to about 55° C. In one embodiment the first stage of hydrolysis and the second stage of hydrolysis are performed at about the same temperature. In another embodiment a first stage of hydrolysis has a temperature that is varied from the temperature of a second stage of hydrolysis.

The pH of hydrolysis is in the range of preferably about 3 to about 8, e.g., about 3.5 to about 7, about 4 to about 6, or about 4.5 to about 5.5. In an embodiment of the invention the pH of a first stage and a second stage are independently selected from a pH of about 4.0 to about 5.5, i.e., about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, or about 5.5. In an embodiment a first stage of hydrolysis has a pH that is varied from the pH of a second stage of hydrolysis. In another embodiment a first stage of hydrolysis has a pH that is lower than the pH of a second stage of hydrolysis.

The dry solids content is in the range of preferably about 5 to about 50 wt. %, e.g., about 10 to about 40 wt. %, about 15 to about 30 wt. % or about 10 to about 20 wt. %.

In a preferred embodiment, the invention provides processes comprising a multi-stage hydrolysis in which a different enzyme composition is provided in each stage. In an embodiment the hydrolysis is conducted in more than one reactor in series.

Processes of the invention produce sugars and/or fermentation products from pretreated cellulosic material. The pre-treatment may be any pre-treatment as described herein. Processes of the invention may further include a solid-liquid separation step resulting in a solid fraction and a liquid fraction. In an embodiment the solid-liquid separation is step is carried out after preconditioning, but before hydrolysis.

In an embodiment the solid fraction resulting from the solid-liquid separation step is further treated. In another embodiment the liquid fraction resulting from the solid-liquid separation step is further treated. Each of the solid and liquid fractions may be hydrolyzed and then fermented. In an embodiment the liquid fraction is mixed with the solid fraction and hydrolyzed and fermented together.

Enzymes for Hydrolysis

The present invention relates to use of enzymes in a multi-stage hydrolysis comprising administration of the enzymes as two or more enzyme compositions. In an embodiment the invention comprises administration of different enzyme compositions in a multi-stage hydrolysis process. Preferably, a first enzyme composition administered in a first step of a multi-stage hydrolysis process is sufficient to reduce inhibitors in a substrate-containing slurry. In a further embodiment the first enzyme composition is sufficient to reduce phenolic inhibitors in a substrate-containing slurry. In a still further embodiment, the enzyme activity of the first enzyme composition is further sufficient to increase the susceptibility of the cellulosic material to additional enzymatic hydrolysis in a subsequent stage. In yet another embodiment, the enzyme activity of the first enzyme composition is further sufficient to saccharify at least a portion of the cellulosic material, to result in production of fermentable sugars.

In an embodiment a first enzyme composition of the invention comprises one or more cellulolytic enzymes and at least one of an oxidoreductase and an AA9 (GH61) polypeptide having cellulolytic enhancing activity.

In one embodiment a first enzyme composition of the invention comprises an oxidoreductase. In a preferred embodiment the oxidoreductase is a catalase. In a still further embodiment a first enzyme composition comprises an oxidoreductase and one or more additional enzymes selected from the group consisting of AA9 (GH61) polypeptides, phenol oxidizing enzymes, peroxidases, xylanases, β-xylosidases, acetyl xylan esterases, feruloyl esterases, α-glucuronidases, α-L-arabinofuranosidases, endoglucanases, cellobiohydrolases, β-glucosidases, and lytic polysaccharide monooxygenases. In a further preferred embodiment, a first enzyme composition comprises an oxidoreductase and one or more additional enzymes selected from the group consisting of a cellobiohydrolase, an endoglucanase, a beta-glucosidase, an AA9 (GH61) polypeptide, a xylanase, and a xylosidase. In a still further embodiment a first enzyme composition comprises a catalase and an AA9 (GH61) polypeptide. In yet another embodiment a first enzyme composition comprises a catalase and a beta-glucosidase.

In another embodiment a first enzyme composition of the invention comprises an AA9 (GH61) polypeptide. In a further embodiment a first enzyme composition comprises an AA9 (GH61) polypeptide and one or more additional enzymes selected from the group consisting of phenol oxidizing enzymes, peroxidases, xylanases, β-xylosidases, acetyl xylan esterases, feruloyl esterases, α-glucuronidases, α-L-arabinofuranosidases, endoglucanases, cellobiohydrolases, β-glucosidases, and lytic polysaccharide monooxygenases.

A multi-stage hydrolysis process of the invention may comprise administration of one or more enzyme compositions in addition to a first enzyme composition. In an embodiment, a multi-stage hydrolysis process of the invention further comprises administration of a second enzyme composition comprising one or more cellulases. In a particular embodiment a second enzyme composition is administered in a step of a multi-stage hydrolysis process that is subsequent to a first step in which a first enzyme composition is administered.

One or more (e.g., several) components of the enzymes in the enzyme composition may be native proteins, recombinant proteins, or a combination of native proteins and recombinant proteins. For example, one or more (e.g., several) components may be native proteins of a cell, which is used as a host cell to express recombinantly one or more (e.g., several) other components of the enzyme compositions. It is understood herein that the recombinant proteins may be heterologous (e.g., foreign) and/or native to the host cell. One or more (e.g., several) components of the enzyme compositions may be produced as monocomponents, which are then combined to form the enzyme compositions. The compositions may be protein broths, mixtures of protein broths, and/or monocomponent proteins. The enzyme compositions may be a combination of multicomponent and monocomponent protein preparations. The compositions may be further combined with one or more additional enzyme compositions.

The effective amounts of the enzymes and polypeptides of an enzyme composition of the present invention in deconstructing a cellulosic or hemicellulosic material depend on several factors including, but not limited to, the cellulosic or hemicellulosic material, the concentration of cellulosic or hemicellulosic material, the pretreatment(s) of the cellulosic or hemicellulosic material, temperature, time, pH, and inclusion of fermenting organism (e.g., yeast for Simultaneous Saccharification and Fermentation).

In a particular embodiment of the invention, the invention provides a multi-stage hydrolysis process, wherein a first enzyme composition is added in a first stage of hydrolysis. In a further embodiment of the invention, the invention provides a multi-stage hydrolysis process, wherein a second enzyme composition is added in a second or subsequent stage of hydrolysis, following administration of a first enzyme composition in a prior stage of hydrolysis.

The first enzyme composition is present as about 1% to about 99%, e.g., about 10% to about 90%, about 40% to about 80%, or about 50% to about 70% of the total enzyme protein added during hydrolysis. The second enzyme composition is present as about 99% to about 1%, e.g., about 80% to about 10%, about 60% to about 20%, or about 50% to about 30% of the total enzyme protein added during hydrolysis. In a preferred embodiment, the combined first enzyme composition and second enzyme composition comprise 100% of the total enzyme protein added during hydrolysis.

In one embodiment, an effective amount of total enzyme protein added during hydrolysis to the cellulosic material is about 0.1 to about 15 mg, e.g., about 0.5 to about 15 mg, about 0.5 to about 9 mg, or about 0.5 to about 6 mg per g of the cellulosic material. In a preferred embodiment the total enzyme protein added during hydrolysis comprising all enzyme compositions added in all stages of hydrolysis is about 4 to about 10 mg, or about 4 to about 6 mg per g of the cellulosic material.

The enzymes may be present or added during hydrolysis (i.e., saccharification) in amounts effective from about 0.001 to about 5.0 wt % of solids (TS), more preferably from about 0.025 to about 4.0 wt % of solids, and most preferably from about 0.005 to about 2.0 wt % of solids (TS).

The enzymes in enzyme compositions of the invention may be derived or obtained from any suitable origin, including, archaeal, bacterial, fungal, yeast, plant, or animal origin. The term "obtained" also means herein that the enzyme may have been produced recombinantly in a host organism employing methods described herein, wherein the recombinantly produced enzyme is either native or foreign to the host organism or has a modified amino acid sequence, e.g., having one or more (e.g., several) amino acids that are deleted, inserted and/or substituted, i.e., a recombinantly produced enzyme that is a mutant and/or a fragment of a native amino acid sequence or an enzyme produced by nucleic acid shuffling processes known in the art. Encompassed within the meaning of a native enzyme are natural variants and within the meaning of a foreign enzyme are variants obtained by, e.g., site-directed mutagenesis or shuffling.

Each polypeptide may be a bacterial polypeptide. For example, each polypeptide may be a Gram-positive bacterial polypeptide having enzyme activity, or a Gram-negative bacterial polypeptide having enzyme activity.

Each polypeptide may also be a fungal polypeptide, e.g., a yeast polypeptide or a filamentous fungal polypeptide.

Chemically modified or protein engineered mutants of polypeptides may also be used.

One or more (e.g., several) components of the enzyme preparations or compositions may be a recombinant component, i.e., produced by cloning of a DNA sequence encoding the single component and subsequent cell transformed with the DNA sequence and expressed in a host (see, for example, WO 91/17243 and WO 91/17244). The host may be a heterologous host (enzyme is foreign to host), but the host may under certain conditions also be a homologous host (enzyme is native to host). Monocomponent cellulolytic proteins may also be prepared by purifying such a protein from a fermentation broth.

In a particular embodiment a first enzyme composition comprises one or more cellulolytic enzymes and at least one of an oxidoreductase and an AA9 (GH61) polypeptide having cellulolytic enhancing activity. In a preferred embodiment the oxidoreductase is a catalase. In a further embodiment a first enzyme composition comprises an oxidoreductase and/or an AA9 (GH61) polypeptide and one or more additional enzymes selected from the group consisting of a cellobiohydrolase, a beta-glucosidase, an AA9 (GH61) polypeptide, a xylanase, a xylosidase, a phenol oxidase, a peroxidase, an endo-1,4-β-xylanase, an acetyl xylan esterase (AXE), a ferulolyl esterase, an α-glucuronidase, an α-L-arabinofuranosidase, an endoglucanase, and a lytic polysaccharide monooxygenase (LPMO). In a further embodiment the first enzyme composition has activity in reduction of phenolic inhibitors of hydrolysis and hydrolysis of at least a portion of the cellulosic material.

Examples of cellulolytic enzymes useful in processes of the present invention include, but are not limited to endoglucanases, cellobiohydrolases and beta-glucosidases.

Examples of oxidoreductases useful in processes of the present invention include, but are not limited to, catalases, laccases and peroxidases, such as *Aspergillus fumigatus* catalase, *Aspergillus lentilus* catalase, *Aspergillus niger* catalase, *Aspergillus oryzae* catalase, *Humicola insolens* catalase, *Neurospora crassa* catalase, *Penicillium emersonii* catalase, *Scytalidium thermophilum* catalase, *Talaromyces stipitatus* catalase, *Thermoascus aurantiacus* catalase (GENSEQP™ Accession No. BAC11005), *Coprinus cinereus* laccase, *Myceliophthora thermophila* laccase, *Polyporus pinsitus* laccase, *Pycnoporus cinnabarinus* laccase, *Rhizoctonia solani* laccase, *Streptomyces coelicolor* laccase, *Coprinus cinereus* peroxidase, Soy peroxidase, Royal palm peroxidase, lytic polysaccharide monooxygenase from *Thermoascus aurantiacus*, and lytic polysaccharide monooxygenase from *Penicillium emersonii*. In one embodiment, oxidoreductases of the invention may include, but are not limited to phenol oxidizing enzymes and lytic polysaccharide monooxygenases (LPMO).

In one aspect, the catalase is selected from the group consisting of: (i) a catalase comprising or consisting of the mature polypeptide of SEQ ID NO: 24; (ii) a catalase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 24; (iii) a catalase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 23; and (iv) a catalase encoded by a polynucleotide that hybridizes under at least high stringency conditions, e.g., very high stringency conditions, with the mature polypeptide coding sequence of SEQ ID NO: 23 or the full-length complement thereof.

In the processes of the present invention, any AA9 (GH61) polypeptide may be used as a component of an enzyme composition. In an embodiment the AA9 is heterologous to a host cell in which it is expressed.

Examples of AA9 (GH61) polypeptides useful in the processes of the present invention include, but are not limited to, AA9 polypeptides from *Aspergillus aculeatus* (WO 2012/125925), *Aspergillus fumigatus* (WO 2010/138754), *Aurantiporus alborubescens* (WO 2012/122477), *Chaetomium thermophilum* (WO 2012/101206), *Humicola insolens* (WO 2012/146171), *Malbranchea cinnamomea* (WO 2012/101206), *Myceliophthora thermophila* (WO 2009/085935, WO 2009/085859, WO 2009/085864, WO 2009/085868, WO 2009/033071, WO 2012/027374, and WO 2012/068236), *Penicillium pinophilum* (WO 2011/005867), *Penicillium* sp. (*emersonii*) (WO 2011/041397, WO 2012/000892 and GENSEQP™ Accession No. BAL61510), *Penicillium thomii* (WO 2012/122477), *Talaromyces emersonii* (WO 2012/000892), *Talaromyces leycettanus* (WO 2012/101206), *Talaromyces stipitatus* (WO 2012/135659), *Talaromyces thermophilus* (WO 2012/129697 and WO 2012/130950), *Thermoascus aurantiacus* (WO 2005/074656 and WO 2010/065830), *Thermoascus crustaceous* (WO 2011/041504), *Thermoascus* sp. (WO 2011/039319), *Thermomyces lanuginosus* (WO 2012/113340, WO 2012/129699, WO 2012/130964, and WO 2012/129699), *Thielavia terrestris* (WO 2005/074647, WO 2008/148131, WO 2011/035027, and GENSEQP™ Accession No. AYB51150), *Trametes versicolor* (WO 2012/092676 and WO 2012/093149), *Trichoderma reesei* (WO 2007/089290 and WO 2012/149344), and *Trichophaea saccata* (WO 2012/122477).

Examples of AA9 (GH61) polypeptides useful in the processes of the present invention further include, but are not limited to, amino acid sequences having at least 35%, e.g., at least 40%, at least 45%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of any of the foregoing AA9 polypeptides.

In another aspect, the AA9 polypeptide having cellulolytic enhancing activity is selected from the group consisting of: (i) an AA9 polypeptide having cellulolytic enhancing activity comprising or consisting of the mature polypeptide of SEQ ID NO: 8; (ii) an AA9 polypeptide having cellulolytic enhancing activity comprising or consisting of an amino acid sequence having at least 35%, e.g., at least 40%, at least 45%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 8; (iii) an AA9 polypeptide having cellulolytic enhancing activity encoded by a polynucleotide comprising or consisting of a nucleotide sequence having at least 35%, e.g., at least 40%, at least 45%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 7; and (iv) an AA9 polypeptide having cellulolytic enhancing activity encoded by a polynucleotide that hybridizes under at least high stringency conditions, e.g., very high stringency conditions, with the mature polypeptide coding sequence of SEQ ID NO: 7 or the full-length complement thereof. In one embodiment, the AA9 polypeptide is used in the presence of a soluble activating divalent metal cation according to WO 2008/151043, e.g., manganese or copper.

In another embodiment, the AA9 polypeptide is used in the presence of a dioxy compound, a bicylic compound, a heterocyclic compound, a nitrogen-containing compound, a quinone compound, a sulfur-containing compound, or a liquor obtained from a pretreated cellulosic material such as pretreated corn stover (WO 2012/021394, WO 2012/021395, WO 2012/021396, WO 2012/021399, WO 2012/021400, WO 2012/021401, WO 2012/021408, and WO 2012/021410).

In one embodiment, such a compound is added at a molar ratio of the compound to glucosyl units of cellulose of about $10^{-6}$ to about 10, e.g., about $10^{-6}$ to about 7.5, about $10^{-6}$ to about 5, about $10^{-6}$ to about 2.5, about $10^{-6}$ to about 1, about $10^{-5}$ to about 1, about $10^{-5}$ to about $10^{-1}$, about $10^{-4}$ to about $10^{-1}$, about $10^{-3}$ to about $10^{-1}$, or about $10^{-3}$ to about $10^{-2}$. In another embodiment, an effective amount of such a compound is about 0.1 µM to about 1 M, e.g., about 0.5 µM to about 0.75 M, about 0.75 µM to about 0.5 M, about 1 µM to about 0.25 M, about 1 µM to about 0.1 M, about 5 µM to about 50 mM, about 10 µM to about 25 mM, about 50 µM to about 25 mM, about 10 µM to about 10 mM, about 5 µM to about 5 mM, or about 0.1 mM to about 1 mM.

The term "liquor" means the solution phase, either aqueous, organic, or a combination thereof, arising from treatment of a lignocellulose and/or hemicellulose material in a slurry, or monosaccharides thereof, e.g., xylose, arabinose, mannose, etc., under conditions as described in WO 2012/021401, and the soluble contents thereof. A liquor for cellulolytic enhancement of an AA9 polypeptide may be produced by treating a lignocellulose or hemicellulose material (or feedstock) by applying heat and/or pressure, optionally in the presence of a catalyst, e.g., acid, optionally in the presence of an organic solvent, and optionally in combination with physical disruption of the material, and then separating the solution from the residual solids. Such conditions determine the degree of cellulolytic enhancement obtainable through the combination of liquor and an AA9 polypeptide during hydrolysis of a cellulosic substrate by a cellulolytic enzyme composition. The liquor may be separated from the treated material using a method standard in the art, such as filtration, sedimentation, or centrifugation.

In one embodiment, an effective amount of the liquor to cellulose is about $10^{-6}$ to about 10 g per g of cellulose, e.g., about $10^{-6}$ to about 7.5 g, about $10^{-6}$ to about 5 g, about $10^{-6}$ to about 2.5 g, about $10^{-6}$ to about 1 g, about $10^{-5}$ to about 1 g, about $10^{-5}$ to about $10^{-1}$ g, about $10^{-4}$ to about $10^{-1}$ g, about $10^{-3}$ to about $10^{-1}$ g, or about $10^{-3}$ to about $10^{-2}$ g per g of cellulose.

Examples of bacterial endoglucanases that may be used in the present invention, include, but are not limited to, *Acidothermus cellulolyticus* endoglucanase (WO 91/05039; WO 93/15186; U.S. Pat. No. 5,275,944; WO 96/02551; U.S. Pat. No. 5,536,655; WO 00/70031; WO 05/093050), *Erwinia carotovara* endoglucanase (Saarilahti et al., 1990, *Gene* 90: 9-14), *Thermobifida fusca* endoglucanase III (WO 05/093050), and *Thermobifida fusca* endoglucanase V (WO 05/093050).

Examples of fungal endoglucanases that may be used in the present invention, include, but are not limited to, *Aspergillus aculeatus* endoglucanase (Ooi et al., 1990, *Nucleic Acids Research* 18: 5884), *Aspergillus kawachii* endoglucanase (Sakamoto et al., 1995, *Current Genetics* 27: 435-439), *Fusarium oxysporum* endoglucanase (GenBank:L29381), *Humicola grisea* var. *thermoidea* endoglucanase (GenBank: AB003107), *Humicola insolens* endoglucanase V, *Melanocarpus albomyces* endoglucanase (GenBank:MAL515703), *Myceliophthora thermophila* CBS 117.65 endoglucanase, *Neurospora crassa* endoglucanase (GenBank:XM_324477), *Thermoascus aurantiacus* endoglucanase I (GenBank: AF487830), *Trichoderma reesei* endoglucanase I (Penttila et al., 1986, *Gene* 45: 253-263), *Trichoderma reesei* Cel7B endoglucanase I (GenBank:M15665), *Trichoderma reesei* endoglucanase II (Saloheimo et al., 1988, *Gene* 63:11-22), *Trichoderma reesei* Cel5A endoglucanase II (GenBank: M19373), *Trichoderma reesei* endoglucanase III (Okada et al., 1988, *Appl. Environ. Microbiol.* 64: 555-563, GenBank: AB003694), *Trichoderma reesei* endoglucanase V (Saloheimo et al., 1994, *Molecular Microbiology* 13: 219-228, GenBank:Z33381), and *Trichoderma reesei* strain No. VTT-D-80133 endoglucanase (GenBank:M15665).

In another embodiment, an enzyme composition of the invention further comprises a *Trichoderma* endoglucanase I or a homolog thereof. In another aspect, an enzyme composition further comprises a *Trichoderma reesei* endoglucanase I or a homolog thereof. In another aspect, an enzyme composition further comprises a *Trichoderma reesei* Cel7B endoglucanase I (GENBANK™ accession no. M15665) or homolog thereof. In another aspect, the *Trichoderma reesei* endoglucanase I or a homolog thereof is native to the host cell.

In another aspect, an enzyme composition of the invention further or even further comprises a *Trichoderma* endoglucanase II or a homolog thereof. In another aspect, an enzyme composition further comprises a *Trichoderma reesei* endoglucanase II or a homolog thereof. In another aspect, an enzyme composition further comprises a *Trichoderma reesei* Cel5A endoglucanase II (GENBANK™ accession no. M19373) or a homolog thereof. In another aspect, the *Trichoderma reesei* endoglucanase II or a homolog thereof is native to the host cell.

Examples of cellobiohydrolases useful in the present invention include, but are not limited to, *Aspergillus aculeatus* cellobiohydrolase II (WO 2011/059740), *Aspergillus fumigatus* cellobiohydrolase I (GENSEQP™ Accession No. AZI04842), *Aspergillus fumigatus* cellobiohydrolase II (GENSEQP™ Accession No. AZI04854), *Chaetomium thermophilum* cellobiohydrolase I, *Chaetomium thermophilum* cellobiohydrolase II, *Humicola insolens* cellobiohydrolase I, *Myceliophthora thermophila* cellobiohydrolase II (WO 2009/042871), *Penicillium occitanis* cellobiohydrolase I (GenBank:AY690482), *Talaromyces emersonii* cellobiohydrolase I (GenBank:AF439936), *Thielavia hyrcanie* cellobiohydrolase II (WO 2010/141325), *Thielavia terrestris* cellobiohydrolase II (CEL6A, WO 2006/074435), *Trichoderma reesei* cellobiohydrolase I, *Trichoderma reesei* cellobiohydrolase II, *Trichophaea saccata* cellobiohydrolase II (WO 2010/057086), *Talaromyces leycettanus* cellobiohydrolase I (GENSEQP™ Accession No. AZY49536), and *Talaromyces leycettanus* cellobiohydrolase II (GENSEQP™ Accession No. AZY49446).

Examples of beta-glucosidases useful in the present invention include, but are not limited to, beta-glucosidases from *Aspergillus aculeatus* (Kawaguchi et al., 1996, *Gene* 173: 287-288), *Aspergillus fumigatus* (GENSEQP™ Accession No. AEA33202), an *Aspergillus fumigatus* variant such as GENSEQP™ Accession No. AZU67153, *Aspergillus oryzae* (WO 02/095014) or the fusion protein having beta-glucosidase activity disclosed in WO 2008/057637, *Penicillium brasilianum* IBT 20888 (WO 2007/019442 and WO 2010/088387), *Thielavia terrestris* (WO 2011/035029), *Trichophaea saccata* (WO 2007/019442) and *Trichoderma reesei*.

Other useful endoglucanases, cellobiohydrolases, and beta-glucosidases are disclosed in numerous Glycosyl Hydrolase families using the classification according to Henrissat, 1991, *Biochem. J.* 280: 309-316, and Henrissat and Bairoch, 1996, *Biochem. J.* 316: 695-696.

Examples of xylanases useful in the processes of the present invention include, but are not limited to, xylanases from *Aspergillus aculeatus* (GeneSeqP:AAR63790; WO 94/21785), *Aspergillus fumigatus* (WO 2006/078256), *Penicillium pinophilum* (WO 2011/041405), *Penicillium* sp. (WO 2010/126772), *Talaromyces lanuginosus* GH11 (WO 2012/130965), *Talaromyces thermophilus* GH11 (WO 2012/130950), *Thielavia terrestris* NRRL 8126 (WO 2009/079210), *Trichophaea saccata* GH10 (WO 2011/057083), and *Talaromyces leycettanus* GH10 (GENSEQP™ Accession No. BAK46118).

Examples of beta-xylosidases useful in the processes of the present invention include, but are not limited to, beta-xylosidases from *Aspergillus fumigatus* (GENSEQP™ Accession No. AZI05042; WO 2013/028928), *Neurospora crassa* (SwissProt:Q7SOW4), *Trichoderma reesei* (UniProtKB/TrEMBL:Q92458), *Trichoderma reesei* such as the mature polypeptide of GENSEQP™ Accession No. AZI04896, and *Talaromyces emersonii* (SwissProt: Q8X212).

Examples of acetylxylan esterases useful in the processes of the present invention include, but are not limited to, acetylxylan esterases from *Aspergillus aculeatus* (WO 2010/108918), *Chaetomium globosum* (UniProt:Q2GWX4), *Chaetomium gracile* (GeneSeqP:AAB82124), *Humicola insolens* DSM 1800 (WO 2009/073709), *Hypocrea jecorina* (WO 2005/001036), *Myceliophtera thermophila* (WO 2010/014880), *Neurospora crassa* (UniProt:q7s259), *Phaeosphaeria nodorum* (UniProt:Q0UHJ1), and *Thielavia terrestris* NRRL 8126 (WO 2009/042846).

Examples of feruloyl esterases (ferulic acid esterases) useful in the processes of the present invention include, but are not limited to, feruloyl esterases from *Humicola insolens* DSM 1800 (WO 2009/076122), *Neosartorya fischeri* (UniProt:A1D9T4), *Neurospora crassa* (UniProt:Q9HGR3), *Penicillium aurantiogriseum* (WO 2009/127729), and *Thielavia terrestris* (WO 2010/053838 and WO 2010/065448).

Examples of arabinofuranosidases useful in the processes of the present invention include, but are not limited to, arabinofuranosidases from *Aspergillus niger* (GeneSeqP: AAR94170), *Humicola insolens* DSM 1800 (WO 2006/114094 and WO 2009/073383), and *M. giganteus* (WO 2006/114094).

Examples of alpha-glucuronidases useful in the processes of the present invention include, but are not limited to, alpha-glucuronidases from *Aspergillus clavatus* (UniProt: alcc12), *Aspergillus fumigatus* (SwissProt:Q4WW45), *Aspergillus niger* (UniProt:Q96WX9), *Aspergillus terreus* (SwissProt: Q0CJP9), *Humicola insolens* (WO 2010/014706), *Penicillium aurantiogriseum* (WO 2009/068565), *Talaromyces emersonii* (UniProt:Q8X211), and *Trichoderma reesei* (UniProt:Q99024).

In an embodiment, a first enzyme composition of the invention comprises an enzyme sufficient to reduce the inhibitors, e.g., phenolics, in a substrate-containing slurry. In an embodiment an oxidoreductaseis present in the first enzyme composition as about 0% to about 25% of the total protein added during hydrolysis, e.g., about 0.25% to about 20%, about 0.5% to about 15%, about 0.75% to about 10%, about 1% to about 9.5%, about 1.25% to about 9%, about 1.5% to about 8%, or about 1.75% to about 8% of the total enzyme protein added during hydrolysis. In another embodiment, the first enzyme composition comprises an effective amount of a polypeptide having oxidoreductase activity to the cellulosic or hemicellulosic material of about 0.001 to about 0.5 mg, e.g., about 0.05 to about 0.5 mg, about 0.05 to about 0.25 mg, or about 0.08 to about 0.1 mg per g of the cellulosic or hemicellulosic material. In still another embodiment an oxidoreductase is present in the first enzyme composition as a laccase and is present as about 0% to about 7% of the total protein added during hydrolysis, e.g., about 0.01% to about 5%, about 0.02% to about 3%, about 0.03% to about 2%, about 0.04% to about 1.5%, or about 0.05 to about 1.25%, of the total enzyme protein added during hydrolysis. In another embodiment, the first enzyme composition comprises an effective amount of a polypeptide having laccase activity to the cellulosic or hemicellulosic material of about 0.01 to about 0.2 mg, e.g., about 0.005 to about 0.1 mg, or about 0.002 to about 0.05 mg per g of the cellulosic or hemicellulosic material.

In an embodiment an AA9 (GH61) is present in the first enzyme composition as about 0% to about 25% of the total protein added during hydrolysis, e.g., about 2.5% to about 25%, about 5% to about 25%, about 7.5% to about 20%, about 10% to about 19%, or about 12% to about 18%, of the total enzyme protein added during hydrolysis. In another embodiment, the first enzyme composition comprises an effective amount of a polypeptide having AA9 activity to the cellulosic or hemicellulosic material of about 0.1 to about 1.0 mg, e.g., about 0.1 to about 0.5, or about 0.2 to about 0.5 mg per g of the cellulosic or hemicellulosic material.

In one embodiment, the amount of cellobiohydrolase I in an enzyme composition of the present invention is about 5% to about 60% of the total enzyme protein added during hydrolysis, e.g., about 7.5% to about 55%, about 10% to about 50%, about 12.5% to about 45%, about 15% to about 40%, about 17.5% to about 35%, and about 20% to about 30% of the total enzyme protein added during hydrolysis.

In another embodiment, the amount of cellobiohydrolase II in an enzyme composition of the present invention is about 2.0 to about 40% of the total enzyme protein added during hydrolysis, e.g., about 3.0% to about 35%, about 4.0% to about 30%, about 5% to about 25%, about 6% to about 20%, about 7% to about 15%, and about 7.5% to about 12% of the total enzyme protein added during hydrolysis.

In another embodiment, the amount of beta-glucosidase in an enzyme composition of the present invention is about 0% to about 30% of the total enzyme protein added during hydrolysis, e.g., about 1% to about 27.5%, about 1.5% to about 25%, about 2% to about 22.5%, about 3% to about 20%, about 4% to about 19%, about 4.5% to about 18%, about 5% to about 17%, and about 6% to about 16% of the total enzyme protein added during hydrolysis.

In another embodiment, the amount of xylanase in an enzyme composition of the present invention is about 0% to about 30% of the total enzyme protein added during hydrolysis, e.g., about 0.5% to about 30%, about 1.0% to about 27.5%, about 1.5% to about 25%, about 2% to about 22.5%, about 2.5% to about 20%, about 3% to about 19%, about 3.5% to about 18%, and about 4% to about 17% of the total enzyme protein added during hydrolysis.

In another embodiment, the amount of beta-xylosidase in an enzyme composition of the present invention is about 0% to about 50% of the total enzyme protein added during hydrolysis, e.g., about 0.5% to about 30%, about 1.0% to about 27.5%, about 1.5% to about 25%, about 2% to about 22.5%, about 2.5% to about 20%, about 3% to about 19%, about 3.5% to about 18%, and about 4% to about 17% of the total enzyme protein added during hydrolysis.

In another embodiment, the amount of endoglucanase I in an enzyme composition of the present invention is about 0.5% to about 30% of the total enzyme protein added during hydrolysis, e.g., about 1.0% to about 25%, about 2% to about 20%, about 4% to about 25%, about 5% to about 20%, about 6% to about 15%, and about 7% to about 12% of the total enzyme protein added during hydrolysis.

In another embodiment, the amount of endoglucanase II in an enzyme composition of the present invention is about 0.5% to about 30% of the total protein of the enzyme composition, e.g., about 1.0% to about 25%, about 2% to about 20%, about 4% to about 25%, about 5% to about 20%, about 6% to about 15%, and about 7% to about 12% of the total enzyme protein added during hydrolysis.

The amount of protein can be determined as described in Example 3.

In a particular embodiment a first enzyme composition is derived from *Trichoderma reesei*, further comprising a cellobiohydrolase I of SEQ ID NO: 2, a cellobiohydrolase II of SEQ ID NO: 4, an endoglucanase I of SEQ ID NO: 14, an endoglucanase II of SEQ ID NO: 16, a catalase of SEQ ID NO: 24, and/or an AA9 (GH61) polypeptide having cellulolytic enhancing activity of SEQ ID NO: 8.

In an embodiment a second enzyme composition comprises one or more cellulases. In a further embodiment a second enzyme composition comprises a cellulolytic enzyme composition comprising one or more (e.g., several) enzymes selected from the group consisting of a cellobiohydrolase, an endoglucanase, a beta glucosidase and an AA9 polypeptide having cellulolytic enhancing activity.

In a further embodiment a second enzyme composition comprises one or more hemicellulases. In an embodiment, the hemicellulase is preferably one or more (e.g., several) enzymes selected from the group consisting of an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase.

In an embodiment the second enzyme composition is or comprises a commercial cellulolytic enzyme preparation. Examples of commercial cellulolytic enzyme preparations suitable for use in the present invention include, for example, CELLIC® CTec (Novozymes A/S), CELLIC® CTec2 (Novozymes A/S), CELLIC® Ctec3 (Novozymes A/S), CELLUCLAST® (Novozymes A/S), CELLUZYME™ (Novozymes A/S), CEREFLO® (Novo Nordisk A/S), and ULTRAFLO® (Novozymes A/S), ACCELLERASE® (Danisco US Inc.), LAMINEX® (Danisco US Inc.), SPEZYME® CP (Danisco US Inc.), ROHAMENT® 7069 W (AB Enzymes), FIBREZYME® LDI (Dyadic International, Inc.), FIBREZYME® LBR (Dyadic International, Inc.), or VISCOSTAR™ 150L (Dyadic International, Inc.).

In an embodiment the second enzyme composition is or comprises a commercial hemicellulolytic enzyme preparation. Examples of commercial hemicellulolytic enzyme preparations suitable for use in the present invention include, for example, SHEARZYME™ (Novozymes A/S), CELLIC® HTec (Novozymes A/S), CELLIC® HTec2 (Novozymes A/S), CELLIC® HTec3 (Novozymes A/S), VISCOZYME® (Novozymes A/S), ULTRAFLO® (Novozymes A/S), PULPZYME® HC (Novozymes A/S), MULTIFECT® Xylanase (Danisco US Inc.), ACCELLERASE® XY (Danisco US Inc.), ACCELLERASE® XC (Danisco US Inc.), ACCELLERASE® TRIO (Danisco US Inc.), ECOPULP® TX-200A (Roal Oy LLC), HSP 6000 Xylanase (DSM), DEPOL™ 333P (Biocatalysts Limit, Wales, UK), DEPOL™ 740L. (Biocatalysts Limit, Wales, UK), and DEPOL™ 762P (Biocatalysts Limit, Wales, UK), ALTERNA FUEL 100P (Dyadic), and ALTERNA FUEL 200P (Dyadic).

As described herein, a first enzyme composition is added during a first stage of hydrolysis and a second enzyme composition is added in a subsequent (e.g., second) or latter stage of hydrolysis. In one embodiment enzyme compositions are comprised of component enzyme compositions. In an embodiment the components of the first enzyme composition are mixed or blended prior to addition to the reactor. In a further embodiment the components of the first enzyme composition are added simultaneously or sequentially to the reactor. In another embodiment, the components of the second enzyme composition are mixed or blended prior to addition to the reactor. In another embodiment the first enzyme composition and the second enzyme composition are added in different stages of hydrolysis in a multi-stage hydrolysis process. In a further embodiment, the first enzyme composition, or component parts thereof, is added to a reactor before, concurrent with, or after addition of the lignocellulosic material to the reactor. In a still further embodiment, the second enzyme composition, or component parts thereof, is added to a reactor after addition of the lignocellulosic material and the first enzyme composition to the reactor.

One or more (e.g., several) of the enzymes added during hydrolysis may be wild-type proteins expressed by the host strain, recombinant proteins, or a combination of wild-type proteins expressed by the host strain and recombinant proteins. For example, one or more (e.g., several) enzymes may be native proteins of a cell, which is used as a host cell to express recombinantly the enzymes added during hydrolysis.

In another aspect, the enzyme compositions can further comprise a whole broth preparation of a *Trichoderma* strain. In another aspect, the enzyme compositions can further comprise a whole broth preparation of a *Trichoderma reesei* strain.

In another aspect, the enzyme compositions can further comprise a whole broth preparation of a *Talaromyces emersonii* strain.

In another aspect, the enzyme compositions can further comprise a whole broth preparation of a *Myceliophthora* strain. In another aspect, the enzyme compositions can further comprise a whole broth preparation of a *Myceliophthora thermophila* strain.

The enzyme compositions may be prepared in accordance with methods known in the art and may be in the form of a liquid or a dry composition. The compositions may be stabilized in accordance with methods known in the art.

The enzyme compositions may result from a single fermentation or may be a blend of two or more fermentations, e.g., three, four, five, six, seven, etc. fermentations. For example, one fermentation may produce cellulases (e.g., endoglucanases, cellobiohydrolases, beta-glucosidase) and a second fermentation may produce hemicellulases (e.g., xylanase and beta-xylosidase), which are then blended in a specific ratio, e.g., 10/90 v/v, 25/75 v/v, 50:50 v/v, 75:25 v/v, or 90/10 v/v, respectively, to produce an enzyme composition. In another example, one fermentation may produce cellulases (e.g., endoglucanases, cellobiohydrolases, beta-glucosidase), a second fermentation may produce hemicellulases (e.g., xylanase and beta-xylosidase), and a third fermentation may produce an AA9 (GH61) polypeptide, which are then blended in a specific ratio, e.g., 10:80:20 v/v/v, 20:60:20 v/v/v, 40:40:20 v/v/v, 40:20:40 v/v/v, or 50:10:40 v/v/v, respectively, to produce an enzyme composition.

The enzyme compositions may be in any form suitable for use, such as, for example, a crude fermentation broth with or without cells removed, a cell lysate with or without cellular debris, a semi-purified or purified enzyme preparation, or a *Trichoderma* host cell as a source of the enzymes. The enzyme compositions may be a dry powder or granulate, a non-dusting granulate, a liquid, a stabilized liquid, or a stabilized protected enzyme. Liquid enzyme preparations may, for instance, be stabilized by adding stabilizers such as a sugar, a sugar alcohol or another polyol, and/or lactic acid or another organic acid according to established processes.

The enzyme compositions may also be a fermentation broth formulation or a cell composition. The fermentation broth product further comprises additional ingredients used in the fermentation process, such as, for example, cells (including, the host cells containing the gene encoding the polypeptide of the present invention which are used to produce the polypeptide), cell debris, biomass, fermentation media and/or fermentation products. In some embodiments, the composition is a cell-killed whole broth containing organic acid(s), killed cells and/or cell debris, and culture medium.

The term "fermentation broth" refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains live cells, killed cells and/or cell debris. In one embodiment, the composition comprises live cells. In another embodiment, killed cells, and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis (e.g., expression of cellulase and/or glucosidase enzyme(s)). In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid slurry, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by the methods described in WO 90/15861 or WO 2010/096673.

The fermentation may be any method of cultivation of a cell resulting in the expression or isolation of an enzyme or protein. Fermentation may, therefore, be understood as comprising shake flask cultivation, or small-scale or large-scale fermentation (including continuous, batch, fed-batch, or solid state fermentations) in laboratory or industrial fermentors performed in a suitable medium and under conditions allowing the enzyme to be expressed or isolated. The resulting enzymes produced by the methods described above may be recovered from the fermentation medium and purified by conventional procedures.

Fermentation

The fermentable sugars obtained from the hydrolyzed cellulosic material may be fermented by one or more (e.g., several) fermenting microorganisms capable of fermenting the sugars directly or indirectly into a desired fermentation product.

"Fermentation" or "fermentation process" refers to any fermentation process or any process comprising a fermentation step. Fermentation processes also include fermentation processes used in the consumable alcohol industry (e.g., beer and wine), dairy industry (e.g., fermented dairy products), leather industry, and tobacco industry. The fermentation conditions depend on the desired fermentation product and fermenting organism and may easily be determined by one skilled in the art.

In the fermentation step, sugars, released from the cellulosic material as a result of the pretreatment and enzymatic hydrolysis steps, are fermented to a product, e.g., ethanol, by a fermenting organism, such as yeast. Hydrolysis (saccharification) and fermentation may be separate or simultaneous. Hydrolysis as described herein includes multi-stage hydrolysis. Where hydrolysis and fermentation are simultaneous, fermentation is carried out with one or more stages of hydrolysis.

Hydrolysis (saccharification) and fermentation, separate or simultaneous, include, but are not limited to, separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); and direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step (Philippidis, G. P., 1996, Cellulose bioconversion technology, in Handbook on Bioethanol: Production and Utilization, Wyman, C. E., ed., Taylor & Francis, Washington, D.C., 179-212). SSCF involves the co-fermentation of multiple sugars (Sheehan and Himmel, 1999, Biotechnol. Prog. 15: 817-827). HHF involves a separate hydrolysis step, and in addition a simultaneous saccharification and hydrolysis step, which can be carried out in the same reactor. The steps in an HHF process can be carried out at different temperatures, i.e., high temperature enzymatic saccharification followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product (Lynd et al., 2002, Microbiol. Mol. Biol. Reviews 66: 506-577). It is understood herein that any method known in the art comprising pretreatment, enzymatic hydrolysis (saccharification), fermentation, or a combination thereof, can be used in the practicing processes of the present invention.

Still further, the invention relates to processes of producing a fermentation product from a lignocellulosic material, the process comprising: a) a step of contacting a lignocellulosic material with a first enzyme composition comprising one or more cellulolytic enzymes and at least one of an oxidoreductase and an AA9 (GH61) polypeptide having cellulolytic enhancing activity; and b) a saccharification step comprising combining the material of step a) with a second enzyme composition comprising one or more cellulases, wherein the first enzyme composition and the second enzyme composition are different enzyme compositions and wherein the process provides increased glucose yield compared to administration of enzymes in a single stage hydrolysis; and fermenting the hydrolyzate to produce a fermentation product. In an embodiment the first enzyme composition is added in a first stage of hydrolysis and the second enzyme composition is added in a later (e.g., second) stage of hydrolysis. In a further embodiment, the stages of hydrolysis are conducted at a pH independently selected from about 4.0 to about 5.5. In a still further embodiment, the first stage of hydrolysis is conducted at a different pH than the second stage of hydrolysis. In another embodiment, the stages of hydrolysis are conducted at a temperature independently selected from about 40° C. to about 60° C. In still another embodiment, the second enzyme composition is added at least about 1 hour to about 24 hours following contacting of the lignocellulosic material and the first enzyme composition.

The present invention also relates to processes of fermenting a lignocellulosic material, comprising: fermenting the lignocellulosic material with one or more (e.g., several) fermenting microorganisms, wherein the lignocellulosic material is hydrolyzed with 1) a first enzyme composition comprising one or more cellulolytic enzymes and at least one of an oxidoreductase and an AA9 (GH61) polypeptide having cellulolytic enhancing activity and 2) a second enzyme composition comprising one or more cellulases to form a hydrolyzate, wherein the first enzyme composition and the second enzyme composition are different enzyme compositions and wherein the process provides increased glucose yield compared to administration of enzymes in a single stage hydrolysis. In one embodiment, the fermenting of the cellulosic material produces a fermentation product. In another embodiment, the processes further comprise recovering the fermentation product from the fermentation.

Any suitable hydrolyzed cellulosic material may be used in the fermentation step in practicing the present invention. The material is generally selected based on economics, i.e., costs per equivalent sugar potential, and recalcitrance to enzymatic conversion.

The term "fermentation medium" is understood herein to refer to a medium before the fermenting microorganism(s) is (are) added, such as, a medium resulting from a saccharification process, as well as a medium used in a simultaneous saccharification and fermentation process (SSF).

Suitable fermenting organisms used according of processes of the invention are described below in the "Fermenting Organism"-section below Fermenting Organism "Fermenting organism" or "fermenting microorganism" refers to any microorganism, including bacterial and fungal organisms, suitable for use in a desired fermentation process to produce a fermentation product. The fermenting organism can be hexose and pentose fermenting organisms, or a combination thereof. Both hexose and pentose fermenting organisms are well known in the art. Suitable fermenting organisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting microorganisms that can ferment hexose sugars include bacterial and fungal organisms, such as yeast. Yeast include strains of *Candida, Kluyveromyces*, and *Saccharomyces*, e.g., *Candida sonorensis, Kluyveromyces marxianus*, and *Saccharomyces cerevisiae*. Preferred yeast includes strains of the *Saccharomyces* spp., preferably *Saccharomyces cerevisiae*.

Examples of fermenting organisms that can ferment pentose sugars include bacterial and fungal organisms, such as some yeast. Xylose fermenting yeast include strains of *Candida*, preferably *C. sheatae* or *C. sonorensis*; and strains of *Pichia*, e.g., *P. stipitis*, such as *P. stipitis* CBS 5773. Pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans, Clostridium acetobutylicum, Clostridium thermocellum, Clostridium phytofermentans, Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans*; *Candida*, such as *C. sonorensis, C. methanosorbosa, C. diddensiae, C. parapsilosis, C. naedodendra, C. blankii, C. entomophilia, C. brassicae, C. pseudotropicalis, C. boidinii, C. utilis*, and *C. scehatae; Clostridium*, such as *C. acetobutylicum, C. thermocellum*, and *C. phytofermentans; E. coli*, especially *E. coli* strains that have been genetically modified to improve the yield of ethanol; *Geobacillus* sp.; *Hansenula*, such as *Hansenula anomala*; *Klebsiella*, such as *K. oxytoca*; *Kluyveromyces*, such as *K. marxianus*, *K. lactis*, *K. thermotolerans*, and *K. fragilis*; *Schizosaccharomyces*, such as *S. pombe*; *Thermoanaerobacter*, such as *Thermoanaerobacter saccharolyticum*; and *Zymomonas*, such as *Zymomonas mobilis*.

Commercially available yeast suitable for ethanol production include, e.g., BIO-FERM® AFT and XR (Lallemand Specialities, Inc., USA), ETHANOL RED® yeast (Lesaffre et Co, pagnie, France), FALI® (AB Mauri Food Inc., USA), FERMIOL® (Rymco International AG, Denmark), GERT STRAND™ (Gert Strand AB, Sweden), and SUPERSTART™ and THERMOSACC® fresh yeast (Lallemand Specialities, Inc., USA).

In an aspect, the fermenting organism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (cofermentation) (Chen and Ho, 1993, *Appl. Biochem. Biotechnol.* 39-40: 135-147; Ho et al., 1998, *Appl. Environ. Microbiol.* 64: 1852-1859; Kotter and Ciriacy, 1993, *Appl. Microbiol. Biotechnol.* 38: 776-783; Walfridsson et al., 1995, *Appl. Environ. Microbiol.* 61: 4184-4190; Kuyper et al., 2004, *FEMS Yeast Research* 4: 655-664; Beall et al., 1991, *Biotech. Bioeng.* 38: 296-303; Ingram et al., 1998, *Biotechnol. Bioeng.* 58: 204-214; Zhang et al., 1995, *Science* 267: 240-243; Deanda et al., 1996, *Appl. Environ. Microbiol.* 62: 4465-4470; WO 03/062430).

In one aspect, the fermenting organism comprises one or more polynucleotides encoding one or more cellulolytic enzymes, hemicellulolytic enzymes, and accessory enzymes.

It is well known in the art that the organisms described above may also be used to produce other substances, as described herein.

The fermenting organism is typically added to the degraded cellulosic material or hydrolyzate and the fermentation is performed for about 8 to about 96 hours, such as about 24 to about 60 hours. The temperature is typically between about 26° C. to about 60° C., in particular about 32° C. or 50° C., and at about pH 3 to about pH 8, such as around pH 4-5, 6, or 7.

In one aspect, the yeast and/or another microorganism are applied to the degraded cellulosic material and the fermentation is performed for about 12 to about 96 hours, such as typically 24-60 hours. In another embodiment, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation may be found in, e.g., "The Alcohol Textbook" (Editors K. Jacques, TP. Lyons and D. R. Kelsall, Nottingham University Press, United Kingdom 1999), which is hereby incorporated by reference.

For ethanol production, following the fermentation the fermented slurry may be distilled to extract the ethanol. The ethanol obtained according to processes of the invention may be used as, e.g., fuel ethanol, drinking ethanol, i.e., potable neutral spirits, or industrial ethanol.

Fermentation Stimulators

A fermentation stimulator may be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products

Processes of the present invention can be used to saccharify the lignocellulosic material to fermentable sugars and to convert the fermentable sugars to many useful fermentation products, e.g., fuel (ethanol, n-butanol, isobutanol, biodiesel, jet fuel) and/or platform chemicals (e.g., acids, alcohols, ketones, gases, oils, and the like). The production of a desired fermentation product from the cellulosic material typically involves pretreatment, enzymatic hydrolysis (saccharification), and fermentation.

A fermentation product may be any substance derived from the fermentation. The fermentation product may be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g., pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product may also be protein as a high value product.

In one embodiment, the fermentation product is an alcohol. The term "alcohol" encompasses a substance that contains one or more hydroxyl moieties. The alcohol may be, but is not limited to, n-butanol, isobutanol, ethanol, methanol, arabinitol, butanediol, ethylene glycol, glycerin, glycerol, 1,3-propanediol, sorbitol, xylitol. See, for example, Gong et al., 1999, Ethanol production from renewable resources, in *Advances in Biochemical Engineering/Biotechnology*, Scheper, T., ed., Springer-Verlag Berlin Heidelberg, Germany, 65: 207-241; Silveira and Jonas, 2002, *Appl. Microbiol. Biotechnol.* 59: 400-408; Nigam and Singh, 1995, *Process Biochemistry* 30(2): 117-124; Ezeji et al., 2003, *World Journal of Microbiology and Biotechnology* 19(6): 595-603.

In another embodiment, the fermentation product is an alkane. The alkane may be an unbranched or a branched alkane. The alkane may be, but is not limited to, pentane, hexane, heptane, octane, nonane, decane, undecane, or dodecane.

In another embodiment, the fermentation product is a cycloalkane. The cycloalkane may be, but is not limited to, cyclopentane, cyclohexane, cycloheptane, or cyclooctane.

In another embodiment, the fermentation product is an alkene. The alkene may be an unbranched or a branched alkene. The alkene may be, but is not limited to, pentene, hexene, heptene, or octene.

In another embodiment, the fermentation product is an amino acid. The organic acid may be, but is not limited to, aspartic acid, glutamic acid, glycine, lysine, serine, or threonine. See, for example, Richard and Margaritis, 2004, *Biotechnology and Bioengineering* 87(4): 501-515.

In another embodiment, the fermentation product is a gas. The gas may be, but is not limited to, methane, $H_2$, $CO_2$, or CO. See, for example, Kataoka et al., 1997, *Water Science and Technology* 36(6-7): 41-47; and Gunaseelan, 1997, *Biomass and Bioenergy* 13(1-2): 83-114.

In another embodiment, the fermentation product is isoprene.

In another embodiment, the fermentation product is a ketone. The term "ketone" encompasses a substance that contains one or more ketone moieties. The ketone may be, but is not limited to, acetone.

In another embodiment, the fermentation product is an organic acid. The organic acid may be, but is not limited to, acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, or xylonic acid. See, for example, Chen and Lee, 1997, *Appl. Biochem. Biotechnol.* 63-65: 435-448.

In another embodiment, the fermentation product is polyketide.

Recovery

The fermentation product(s) may be optionally recovered from the fermentation medium using any method known in the art including, but not limited to, chromatography, electrophoretic procedures, differential solubility, distillation, or extraction. For example, alcohol is separated from the fermented cellulosic material and purified by conventional methods of distillation. Ethanol with a purity of up to about 96 vol. % may be obtained, which may be used as, for example, fuel ethanol, drinking ethanol, i.e., potable neutral spirits, or industrial ethanol.

The present invention is further described by the following paragraphs.

[1] A process of multi-stage hydrolysis of a lignocellulosic material, the process comprising:
  a) a step of contacting a lignocellulosic material with a first enzyme composition comprising one or more cellulolytic enzymes and at least one of an oxidoreductase and an AA9 polypeptide having cellulolytic enhancing activity; and
  b) a saccharification step comprising combining the material of step a) with a second enzyme composition comprising one or more cellulases,
  wherein the first enzyme composition and the second enzyme composition are different enzyme compositions and wherein the process provides increased glucose yield compared to administration of enzymes in a single stage hydrolysis.

[2] The process of paragraph 1, wherein the lignocellulosic material is pretreated.

[3] The process of paragraph 2, wherein the pretreated lignocellulosic material has been subjected to a pretreatment method selected from steam explosion, liquid hot water treatment and acid pretreatment.

[4] The process of any of paragraphs 1 to 3, wherein the lignocellulosic material is corn stover.

[5] The process of paragraph 4, wherein the lignocellulosic material is acid pretreated corn stover.

[6] The process of any of paragraphs 1 to 5, wherein the oxidoreductase is selected from the group consisting of a catalase, a peroxidase and a laccase.

[7] The process of paragraph 6, wherein the catalase or peroxidase is present in the first enzyme composition as about 1.75% to about 8% of the total enzyme protein added during hydrolysis.

[8] The process of paragraph 6, wherein the laccase is present in the first enzyme composition as about 0.05% to about 1.25% of the total enzyme protein added during hydrolysis.

[9] The process of any of paragraphs 1 to 8, wherein the first enzyme composition comprises a catalase selected from the group consisting of: (i) a catalase comprising or consisting of the mature polypeptide of SEQ ID NO: 24; (ii) a catalase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 24; (iii) a catalase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 23; and (iv) a catalase encoded by a polynucleotide that hybridizes under at least high stringency conditions, e.g., very high stringency conditions, with the mature polypeptide coding sequence of SEQ ID NO: 23 or the full-length complement thereof.

[10] The process of any of paragraphs 1 to 9, wherein the first enzyme composition comprises a lytic polysaccharide monooxygenase.

[11] The process of any of paragraphs 1 to 10, wherein the AA9 is present in the first enzyme composition as about 12% to about 18% of the total enzyme protein added during hydrolysis.

[12] The process of any of paragraphs 1 to 11, wherein the AA9 polypeptide is any AA9 polypeptide having cellulolytic enhancing activity.

[13] The process of any of paragraphs 1 to 12, wherein the AA9 polypeptide is selected from the group consisting of: (i) an AA9 polypeptide having cellulolytic enhancing activity comprising or consisting of the mature polypeptide of SEQ ID NO: 8; (ii) an AA9 polypeptide having cellulolytic enhancing activity comprising or consisting of an amino acid sequence having at least 40%, e.g., at least 45%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 8; (iii) an AA9 polypeptide having cellulolytic enhancing activity encoded by a polynucleotide comprising or consisting of a nucleotide sequence having at least 35%, e.g., at least 40%, at least 45%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 7; and (iv) an AA9 polypeptide having cellulolytic enhancing activity encoded by a polynucleotide that hybridizes under at least high stringency conditions, e.g., very high stringency conditions, with the mature polypeptide coding sequence of SEQ ID NO: 7 or the full-length complement thereof.

[14] The process of any of paragraphs 1 to 13, wherein the first enzyme composition comprises a cellobiohydrolase I, a cellobiohydrolase II, an endoglucanase I, an endoglucanase II, and an AA9 polypeptide having cellulolytic enhancing activity.

[15] The process of any of paragraphs 1 to 13, wherein the first enzyme composition comprises a cellobiohydrolase I, a cellobiohydrolase II, and an AA9 polypeptide having cellulolytic enhancing activity.

[16] The process of any of paragraphs 1 to 13, wherein the first enzyme composition comprises a cellobiohydrolase I, a cellobiohydrolase II, an endoglucanase I, an endoglucanase II, and an oxidoreductase.

[17] The process of any of paragraphs 1 to 13, wherein the first enzyme composition comprises a cellobiohydrolase I, a cellobiohydrolase II, and an oxidoreductase.

[18] The process of any of paragraphs 1 to 13, wherein the first enzyme composition comprises a cellobiohydrolase I, a cellobiohydrolase II, an endoglucanase I, an endoglucanase II, an AA9 polypeptide having cellulolytic enhancing activity and an oxidoreductase.

[19] The process of any of paragraphs 1 to 13, wherein the first enzyme composition comprises a cellobiohydrolase I, a cellobiohydrolase II, an AA9 polypeptide having cellulolytic enhancing activity and an oxidoreductase.

[20] The process of any of paragraphs 1 to 19, wherein the first enzyme composition further comprises at least one additional enzyme selected from the group consisting of phenol oxidizing enzymes, peroxidases, xylanases, β-xylosidases, acetyl xylan esterases, feruloyl esterases, α-glucuronidases, α-L-arabinofuranosidases, endoglucanases, cellobiohydrolases, β-glucosidases, and lytic polysaccharide monooxygenases.

[21] The process of any of paragraphs 1 to 20, wherein the second enzyme composition comprises a cellulase.

[22] The process of any of paragraphs 1 to 21, wherein the second enzyme composition is added about 1 hour to about 24 hours after combination of the lignocellulosic material and the first enzyme composition.

[23] The process of paragraph 22, wherein the second enzyme composition is added at least one hour after combination of the lignocellulosic material and the first enzyme composition.

[24] The process of paragraph 22, wherein the second enzyme composition is added at least five hours after combination of the lignocellulosic material and the first enzyme composition.

[25] The process of paragraph 22, wherein the second enzyme composition is added at least seven hours after combination of the lignocellulosic material and the first enzyme composition.

[26] The process of any of paragraphs 1 to 25, wherein step a) is performed at a different pH than the pH of step b).

[27] The process of any of paragraphs 1 to 26, wherein step a) is performed at a different temperature than the temperature of step b).

[28] The process of any of paragraphs 1 to 27, wherein step a) is performed at a different dissolved oxygen level temperature than the dissolved oxygen level of step b).

[29] A process of producing a fermentation product from a lignocellulosic material, the process comprising the steps of:
a) hydrolyzing the lignocellulosic material, comprising:
  1) a step of contacting a lignocellulosic material with a first enzyme composition comprising one or more cellulolytic enzymes and at least one of an oxidoreductase and an AA9 polypeptide having cellulolytic enhancing activity; and
  2) a saccharification step comprising combining the material of step a) with a second enzyme composition comprising one or more cellulases,
  wherein the first enzyme composition and the second enzyme composition are different enzyme compositions and wherein the process provides increased glucose yield compared to administration of enzymes in a single stage hydrolysis; and
b) fermenting the hydrolyzate to produce a fermentation product.

[30] The process of paragraph 29, wherein the lignocellulosic material is pretreated.

[31] The process of paragraph 30, wherein the pretreated lignocellulosic material has been subjected to a pretreatment method selected from steam explosion, liquid hot water treatment and acid pretreatment.

[32] The process of any of paragraphs 29 to 31, wherein the lignocellulosic material is corn stover.

[33] The process of paragraph 32, wherein the lignocellulosic material is acid pretreated corn stover.

[34] The process of any of paragraphs 29 to 33, wherein the oxidoreductase is selected from the group consisting of a catalase, a peroxidase and a laccase.

[35] The process of paragraph 34, wherein the catalase or peroxidase is present in the first enzyme composition as about 1.75% to about 8% of the total enzyme protein added during hydrolysis.

[36] The process of paragraph 34, wherein the laccase is present in the first enzyme composition as about 0.05% to about 1.25% of the total enzyme protein added during hydrolysis.

[37] The process of any of paragraphs 29 to 36, wherein the first enzyme composition comprises a catalase selected from the group consisting of: (i) a catalase comprising or consisting of the mature polypeptide of SEQ ID NO: 24; (ii) a catalase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 24; (iii) a catalase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 23; and (iv) a catalase encoded by a polynucleotide that hybridizes under at least high stringency conditions, e.g., very high stringency conditions, with the mature polypeptide coding sequence of SEQ ID NO: 23 or the full-length complement thereof.

[38] The process of any of paragraphs 29 to 37, wherein the first enzyme composition comprises a lytic polysaccharide monooxygenase.

[39] The process of any of paragraphs 29 to 38, wherein the AA9 is present in the first enzyme composition as about 12 to about 18% of the total enzyme protein added during hydrolysis.

[40] The process of any of paragraphs 29 to 39, wherein the AA9 polypeptide is any AA9 polypeptide having cellulolytic enhancing activity.

[41] The process of any of paragraphs 29 to 40, wherein the AA9 polypeptide is selected from the group consisting of: (i) an AA9 polypeptide having cellulolytic enhancing activity comprising or consisting of the mature polypeptide of SEQ ID NO: 8; (ii) an AA9 polypeptide having cellulolytic enhancing activity comprising or consisting of an amino acid sequence having at least 35%, e.g., at least 40%, at least 45%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 8; (iii) an AA9 polypeptide having cellulolytic enhancing activity encoded by a polynucleotide comprising or consisting of a nucleotide sequence having at least 35%, e.g., at least 40%, at least 45%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 7; and (iv) an AA9 polypeptide having cellulolytic enhancing activity encoded by a polynucleotide that hybridizes under at least high stringency conditions, e.g., very high stringency conditions, with the mature polypeptide coding sequence of SEQ ID NO: 7 or the full-length complement thereof.

[42] The process of any of paragraphs 29 to 41, wherein the first enzyme composition comprises a cellobiohydrolase I, a cellobiohydrolase II, and an AA9 polypeptide having cellulolytic enhancing activity.

[43] The process of any of paragraphs 29 to 41, wherein the first enzyme composition comprises a cellobiohydrolase I, a cellobiohydrolase II, an endoglucanase I, an endoglucanase II, and an oxidoreductase.

[44] The process of any of paragraphs 29 to 41, wherein the first enzyme composition comprises a cellobiohydrolase I, a cellobiohydrolase II, and an oxidoreductase.

[45] The process of any of paragraphs 29 to 41, wherein the first enzyme composition comprises a cellobiohydrolase I, a cellobiohydrolase II, an endoglucanase I, an endoglucanase II, an AA9 polypeptide having cellulolytic enhancing activity and an oxidoreductase.

[46] The process of any of paragraphs 29 to 41, wherein the first enzyme composition comprises a cellobiohydrolase I, a cellobiohydrolase II, an AA9 polypeptide having cellulolytic enhancing activity and an oxidoreductase.

[47] The process of any of paragraphs 29 to 46, wherein the first enzyme composition further comprises at least one additional enzyme selected from the group consisting of phenol oxidizing enzymes, peroxidases, endo-1,4-β-xylanases, β-xylosidases, acetyl xylan esterases, feruloyl esterases, α-glucuronidases, α-L-arabinofuranosidases, endoglucanases, cellobiohydrolases, β-glucosidases, and lytic polysaccharide monooxygenases.

[48] A process of increasing a sugar yield of hydrolysis of a lignocellulosic material, the process comprising the steps of:
a) a step of contacting a lignocellulosic material with a first enzyme composition comprising one or more cellulolytic enzymes and at least one of an oxidoreductase and an AA9 polypeptide having cellulolytic enhancing activity; and
b) a saccharification step comprising combining the material of step a) with a second enzyme composition comprising one or more cellulases,
wherein the first enzyme composition and the second enzyme composition are different enzyme compositions and wherein the process provides increased sugar yield compared to administration of enzymes in a single stage hydrolysis.

[49] The process of paragraph 48, wherein the lignocellulosic material is pretreated.

[50] The process of paragraph 49, wherein the pretreated lignocellulosic material has been subjected to a pretreatment method selected from steam explosion, liquid hot water treatment and acid pretreatment.

[51] The process of any of paragraphs 48 to 50, wherein the lignocellulosic material is corn stover.

[52] The process of paragraph 51, wherein the lignocellulosic material is acid pretreated corn stover.

[53] The process of any of paragraphs 48 to 52, wherein the oxidoreductase is selected from the group consisting of a catalase, a peroxidase and a laccase.

[54] The process of paragraph 53, wherein the catalase or peroxidase is present in the first enzyme composition as about 1.75% to about 8% of the total enzyme protein added during hydrolysis.

[55] The process of paragraph 53, wherein the laccase is present in the first enzyme composition as about 0.05% to about 1.25% of the total enzyme protein added during hydrolysis.

[56] The process of any of paragraphs 48 to 55, wherein the first enzyme composition comprises a catalase selected from the group consisting of: (i) a catalase comprising or consisting of the mature polypeptide of SEQ ID NO: 24; (ii) a catalase comprising or consisting of an amino acid sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 24; (iii) a catalase encoded by a polynucleotide comprising or consisting of a nucleotide sequence having at least 70%, e.g., at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 23; and (iv) a catalase encoded by a polynucleotide that hybridizes under at least high stringency conditions, e.g., very high stringency conditions, with the mature polypeptide coding sequence of SEQ ID NO: 23 or the full-length complement thereof.

[57] The process of any of paragraphs 48 to 56, wherein the AA9 is present in the first enzyme composition as about 12% to about 18% of the total enzyme protein added during hydrolysis.

[58] The process of any of paragraphs 48 to 57, wherein the AA9 polypeptide is any AA9 polypeptide having cellulolytic enhancing activity.

[59] The process of any of paragraphs 48 to 58, wherein the AA9 polypeptide is selected from the group consisting of: (i) an AA9 polypeptide having cellulolytic enhancing activity comprising or consisting of the mature polypeptide of SEQ ID NO: 8; (ii) an AA9 polypeptide having cellulolytic enhancing activity comprising or consisting of an amino acid sequence having at least 35%, e.g., at least 40%, at least 45%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the mature polypeptide of SEQ ID NO: 8; (iii) an AA9 polypeptide having cellulolytic enhancing activity encoded by a polynucleotide comprising or consisting of a nucleotide sequence having at least 35%, e.g., at least 40%, at least 45%, at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 7; and (iv) an AA9 polypeptide having cellulolytic enhancing activity encoded by a polynucleotide that hybridizes under at least high stringency conditions, e.g., very high stringency conditions, with the mature polypeptide coding sequence of SEQ ID NO: 7 or the full-length complement thereof.

[60] The process of any of paragraphs 48 to 59, wherein the first enzyme composition comprises a cellobiohydrolase I, a cellobiohydrolase II, and an AA9 polypeptide having cellulolytic enhancing activity.

[61] The process of any of paragraphs 48 to 59, wherein the first enzyme composition comprises a cellobiohydrolase I, a cellobiohydrolase II, an endoglucanase I, an endoglucanase II, and an oxidoreductase.

[62] The process of any of paragraphs 48 to 59, wherein the first enzyme composition comprises a cellobiohydrolase I, a cellobiohydrolase II, and an oxidoreductase.

[63] The process of any of paragraphs 48 to 59, wherein the first enzyme composition comprises a cellobiohydrolase I, a cellobiohydrolase II, an endoglucanase I, an endoglucanase II, an AA9 polypeptide having cellulolytic enhancing activity and an oxidoreductase.

[64] The process of any of paragraphs 48 to 59, wherein the first enzyme composition comprises a cellobiohydrolase I, a cellobiohydrolase II, an AA9 polypeptide having cellulolytic enhancing activity and an oxidoreductase.

[65] The process of any of paragraphs 48 to 64, wherein the first enzyme composition further comprises at least one additional enzyme selected from the group consisting of phenol oxidizing enzymes, peroxidases, xylanases, β-xylosidases, acetyl xylan esterases, feruloyl esterases, α-glucuronidases, α-L-arabinofuranosidases, endoglucanases, cellobiohydrolases, β-glucosidases, and lytic polysaccharide monooxygenases.

[66] The process of any of paragraphs 48 to 65, wherein the increased sugar yield is increased glucose yield.

The present invention is further described by the following examples that should not be construed as limiting the scope of the invention.

The following are referred to in the examples:

Cellulolytic Enzyme Preparation ("CPrep"):

Cellulolytic enzyme composition derived from *Trichoderma reesei* further comprising a cellobiohydrolase I of SEQ ID NO: 2, a cellobiohydrolase II of SEQ ID NO: 4, an AA9 (GH61) polypeptide having cellulolytic enhancing activity of SEQ ID NO: 8, a beta-glucosidase variant of SEQ ID NO: 18, a catalase of SEQ ID NO: 24, a GH10 xylanase of SEQ ID NO: 10, and a beta-xylosidase of SEQ ID NO: 12.

Xylanase Enzyme Preparation ("XPrep"):

Enzyme composition from *Trichoderma reesei*, further comprising a GH10 xylanase of SEQ ID NO: 10 and a beta-xylosidase of SEQ ID NO: 12.

The invention described and claimed herein is not to be limited in scope by the specific aspects or embodiments herein disclosed, since such are intended as illustrations of several aspects or embodiments of the invention. Any equivalent aspects or embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

EXAMPLES

Example 1

Improved Glucose Yield Using Five Day Two Stage Hydrolysis with First Enzyme Composition Comprising Catalase and/or GH61

Dilute acid steam exploded pre-treated corn stover and cobs was obtained from a 0.5 kg biomass mix of corn stover and corn cobs, mixed with sulfuric acid. The slurry was pressed to obtain a liquid stream and a solids portion. The solids portion was further subjected to pressing and steam explosion. The composition of each liquid and solids stream was analyzed using NREL protocol TP-510-48825, "Laboratory Analytical Procedure (LAP) Review and Integration: Pretreated Slurries" (issued August 2011).

The solids (8.6 g, TS 32.0%) and liquid stream liquor (5.9 g; TS 7.9%) were added to each rotisserie tube. A 10 mm in diameter metal ball was placed into each tube to increase mixing in rotisserie. The pH was adjusted to approximately pH 5.1 using 50% KOH. Additional tap water was added to bring the samples to 17% TS. The samples were incubated in 50° C. rotisserie for about 1 hour to allow the slurry to adjust pH and temperature. After incubation, the pH was approximately pH 4.9-5.0.

Enzyme dilutions were made as set forth in Table 1 below by weight/volume with deionized water and then dosed using positive displacement pipettes. The first enzyme dosing was after 1 hour (dose 1) and the second enzyme dosing was after 7 hours (dose 2) according to Table 1 below. After each enzyme dosing, the samples were vortexed and placed back into 55° C. rotisserie at 12-15 rpm.

TABLE 1

| Sample | Dose 1 (after 1 hr) | Dose 2 (after 7 hr) |
|---|---|---|
| 1 | Cat + GH61 + XPrep + BG (all) | |
| 2 | Cat + GH61 | XPrep + BG |
| 3 | GH61 + BG | XPrep + cat |
| 4 | Cat + BG | XPrep + GH61 |
| 5 | XPrep + cat + GH61 | BG |
| 6 | | Cat + GH61 + XPrep + BG (all) |

The total enzyme in dose 1 and dose 2 together is 4 mg EP/g of cellulose. Enzyme protein concentration was measured with the BCA protein assay as set forth in Example 3 Taken together the composition of dose 1 and dose 2 contains all enzymes of CPrep.

The amount of each enzyme composition used is listed in Table 2 below. Each enzyme composition comprises one or more specified enzymes, in addition to enzymes expressed by the host in which the composition is produced. For example, the specified enzymes in the "BG" composition are β-glucosidase (BG) and AA9 (GH61). The specified enzymes in the "XPrep" composition are a GH10 xylanase and a β-xylosidase. In the "cat" composition, the specified enzymes are catalase and AA9 (GH61). In the GH61 composition, the specified enzyme is GH61 protein.

In Sample 2, Dose 1 is a composition comprising a cellobiohydrolase I of SEQ ID NO: 2, a cellobiohydrolase II of SEQ ID NO: 4, an endoglucanase I of SEQ ID NO: 14, and endoglucanase II of SEQ ID NO: 16, an AA9 (GH61) polypeptide having cellulolytic enhancing activity of SEQ ID NO: 8, and a catalase of SEQ ID NO: 24 at a total of 2.4 mg protein/g cellulose and Dose 2 is a composition comprising a cellobiohydrolase I of SEQ ID NO: 2, a cellobiohydrolase II of SEQ ID NO: 4, an endoglucanase I of SEQ ID NO: 14, and endoglucanase II of SEQ ID NO: 16, a GH10 xylanase of SEQ ID NO: 10, a beta-xylosidase of SEQ ID NO: 12, a beta-glucosidase variant of SEQ ID NO: 18, and an AA9 (GH61) polypeptide of SEQ ID NO: 8, at a total of 1.6 mg protein/g cellulose. Each of Doses 1 and 2 may further comprise additional enzymes expressed by the host in which the composition is produced.

In Sample 3, Dose 1 is a composition comprising a cellobiohydrolase I of SEQ ID NO: 2, a cellobiohydrolase II of SEQ ID NO: 4, an endoglucanase I of SEQ ID NO: 14, and endoglucanase II of SEQ ID NO: 16, an AA9 (GH61) polypeptide having cellulolytic enhancing activity of SEQ ID NO: 8, and a beta-glucosidase variant of SEQ ID NO: 18, at a total of 1.8 mg protein/g cellulose and Dose 2 is a composition comprising a cellobiohydrolase I of SEQ ID NO: 2, a cellobiohydrolase II of SEQ ID NO: 4, an endoglucanase I of SEQ ID NO: 14, and endoglucanase II of SEQ ID NO: 16, a GH10 xylanase of SEQ ID NO: 10, and a beta-xylosidase of SEQ ID NO: 12, a catalase of SEQ ID NO: 24, and an AA9 (GH61) polypeptide of SEQ ID NO: 8, at a total of 2.2 mg protein/g cellulose. Each of Doses 1 and 2 may further comprise additional enzymes expressed by the host in which the composition is produced.

In Sample 4, Dose 1 is a composition comprising a cellobiohydrolase I of SEQ ID NO: 2, a cellobiohydrolase II of SEQ ID NO: 4, an endoglucanase I of SEQ ID NO: 14, and endoglucanase II of SEQ ID NO: 16, a catalase of SEQ ID NO: 24, a beta-glucosidase variant of SEQ ID NO: 18, and an AA9 (GH61) polypeptide of SEQ ID NO: 8, at a total of 2.2 mg protein/g cellulose and Dose 2 is a composition comprising a cellobiohydrolase I of SEQ ID NO: 2, a cellobiohydrolase II of SEQ ID NO: 4, an endoglucanase I of SEQ ID NO: 14, and endoglucanase II of SEQ ID NO: 16, a GH10 xylanase of SEQ ID NO: 10, a beta-xylosidase of SEQ ID NO: 12, and an AA9 (GH61) polypeptide of SEQ ID NO: 8, at a total of 1.8 mg protein/g cellulose. Each of Doses 1 and 2 may further comprise additional enzymes expressed by the host in which the composition is produced.

In Sample 5, Dose 1 is a composition comprising a cellobiohydrolase I of SEQ ID NO: 2, a cellobiohydrolase II of SEQ ID NO: 4, an endoglucanase I of SEQ ID NO: 14, and endoglucanase II of SEQ ID NO: 16, a GH10 xylanase of SEQ ID NO: 10, a beta-xylosidase of SEQ ID NO: 12, a catalase of SEQ ID NO: 24, and an AA9 (GH61) polypeptide of SEQ ID NO: 8, at a total of 3.2 mg protein/g cellulose and Dose 2 is a composition comprising a cellobiohydrolase I of SEQ ID NO: 2, a cellobiohydrolase II of SEQ ID NO: 4, an endoglucanase I of SEQ ID NO: 14, and endoglucanase II of SEQ ID NO: 16, a beta-glucosidase variant of SEQ ID NO: 18, and an AA9 (GH61) polypeptide of SEQ ID NO: 8, at a total of 0.8 mg protein/g cellulose. Each of Doses 1 and 2 may further comprise additional enzymes expressed by the host in which the composition is produced.

TABLE 2

|  | BG | XPrep | cat | GH61 |
|---|---|---|---|---|
| mg protein/g cellulose | 0.80 | 0.80 | 1.4 | 1.00 |

HPLC samples were taken on day 5 of hydrolysis. To sample a hydrolysate, 700 µL of slurry was removed and centrifuged at 14,000 rpm in a Spin-X centrifuge tube for 10 minutes. The filter was discarded and the filtrate was inactivated by addition of 40% sulphuric acid solution (1 µL per 100 µL of sample) and mixing by aspirating. Each inactivated filtrate was dispensed into tube with a pipette tip to avoid any solids on the tube top. Each inactivated filtrate was diluted 10× with 5 mM sulphuric acid in an HPLC vial (minimum volume: 0.5 mL). The content of glucose was then determined using an Agilent HPLC System equipped with an analytical BIO-RAD Aminex® HPX-87H column and a BIO-RAD Cation H refill guard column Aminex® 87H column for sugar detection.

Figure 2:
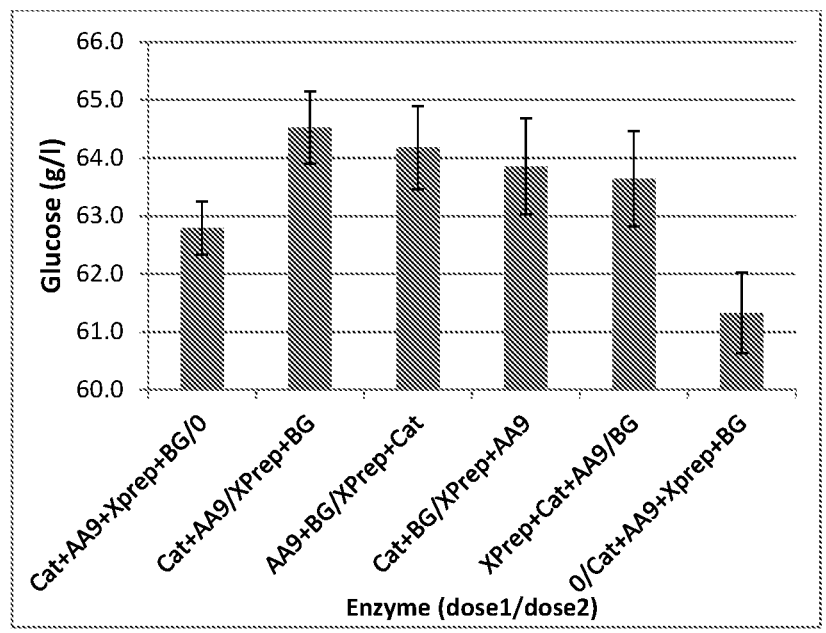
FIG. 2 is a graph showing the glucose yield results of the enzyme dosage schemes detailed in Example 1.

The 5 day glucose yield results are shown in FIG. 2. It can be seen that when an enzyme mix comprised of GH61 and catalase was dosed at 1 hr hydrolysis (i.e., dose 1), higher glucose yield was observed than dosing all of enzyme complex at once either at 1 hr in dose 1 or 7 hours in dose 2. High glucose yield was also achievable when the enzyme mix in dose 1 further contained hemicellulases such as xylanase and β-xylosidase in XPrep. When an enzyme mix in dose 1 comprises β-glucosidase and either GH61 or Catalase, higher glucose yield was obtained than dosing all of enzyme complex at once, either at 1 hour in dose 1 or at 7 hours in dose 2.

Example 2

Improved Glucose Yield Using Three Day Two Stage Hydrolysis with First Enzyme Composition Comprising Catalase and/or GH61

A biomass mix consisting of corn stover and corn cobs was cut and pretreated as described in Example 1.

For this study, enzyme compositions comprising one or more of four specialized enzymes (XPrep, BG, Catalase, and GH61) were used, each composition comprising one or more specified enzymes, in addition to enzymes expressed by the host in which the composition is produced. Each composition was dosed individually at either dose 1 or dose 2, according to the experimental design in Table 3 below.

TABLE 3

| | % dose of 4 mg protein/g cellulose | | | | | | | |
|---|---|---|---|---|---|---|---|---|
| Sam- | Dose 1 | | | | Dose 2 | | | |
| ple | XPrep | BG | Cat | GH61 | XPrep | BG | cat | GH61 |
| 1 | 20% | 30% | 40% | 10% | | | | |
| 2 | | | 40% | | 20% | 30% | | 10% |
| 3 | | | | 10% | 20% | 30% | 40% | |
| 4 | 20% | | 40% | | | | 30% | 10% |
| 5 | | 30% | 40% | | 20% | | | 10% |
| 6 | | | 40% | 10% | 20% | 30% | | |
| 7 | 20% | 30% | 40% | | | | | 10% |
| 8 | | 30% | 40% | 10% | 20% | | | |
| 9 | | | | | 20% | 30% | 40% | 10% |

XPrep is an enzyme composition as set forth above. The BG-containing enzyme composition is comprised of a cellobiohydrolase I of SEQ ID NO: 2, a cellobiohydrolase II of SEQ ID NO: 4, an endoglucanase I of SEQ ID NO: 14, and endoglucanase II of SEQ ID NO: 16, an AA9 (GH61) polypeptide having cellulolytic enhancing activity of SEQ ID NO: 8, and a beta-glucosidase variant of SEQ ID NO: 18. The catalase enzyme composition is a composition comprising a cellobiohydrolase I of SEQ ID NO: 2, a cellobiohydrolase II of SEQ ID NO: 4, an endoglucanase I of SEQ ID NO: 14, and endoglucanase II of SEQ ID NO: 16, an AA9 (GH61) polypeptide having cellulolytic enhancing activity of SEQ ID NO: 8, and a catalase of SEQ ID NO: 24. The AA9 enzyme composition is comprised of a composition comprising a cellobiohydrolase I of SEQ ID NO: 2, a cellobiohydrolase II of SEQ ID NO: 4, an endoglucanase I of SEQ ID NO: 14, and endoglucanase II of SEQ ID NO: 16, and an AA9 (GH61) polypeptide having cellulolytic enhancing activity of SEQ ID NO: 8.

The solid stream of acid pretreated corn stover and cobs (TS 32.0%) was weighed out into a large Kitchen-Aid mixing bowl. The liquor from the liquid stream of acid pretreated corn stover and cobs (TS 7.9%) was added by volume, assuming 1 mL=1 g. The slurry was homogenized at low speed, and then slowly pH adjusted using concentrated alkaline, 50% KOH, to approximately 5.3. The homogenized, pH adjusted slurry was measured for % total solids using a halogen moisture analyser. The slurry was then loaded into 24-deep well plates. A 24-well Porvair bottomless plate was sealed with a mylar seal and then the wells were filled with slurry. The Porvair plate was then used to transfer the slurry to a 24-deep well Kingfisher Flex round bottom plates by flipping the Porvair plate, removing the seal, and then lightly tapping to dispense the slurry. The 24-deep well plates were weighed before and after slurry loading. The weight of the total slurry loaded was divided by the number of wells in order to obtain the average slurry per well, and thus the average glucan content per well. The plates were incubated at 55° C. for 1 hour before Dose 1. Dose 2 was performed 6 hours after Dose 1. The enzymes were diluted weight/volume to account for density. Additional water and enzymes were dosed according to the experimental design by the Biomek-FX. Triplicate samples were divided between three separate plates. After each enzyme dosing, the plates were sealed with a 24-well rubber sealing mat and vigorously vortexed. Plates were vented and vortexed on days 1 and 3 and sampled for HPLC analysis on day 3.

HPLC sampling was performed by using a retractable multi-channel pipette; approximately 200 mL of hydrolysate was aspirated from each well and then dispensed into a 96-well 0.2 um filter plate. The filter plate was centrifuged for 5 minutes at 1.5 k rpm in a table centrifuge. The filtrate was collected in a 96-well collection plate with 1% (final concentration) H2SO4. The filtrate was then diluted into a 96-well dilution plate at 5× using 5 mM H2SO4 mobile phase. The content of glucose and xylose was then determined using an Agilent HPLC System equipped with an analytical BIO-RAD Aminex® HPX-87H column and a BIO-RAD Cation H refill guard column Aminex® 87H column for sugar detection. Standard deviation is shown as the standard deviation across all plates and samples to achieve the most accurate error factor.

Figure 3:
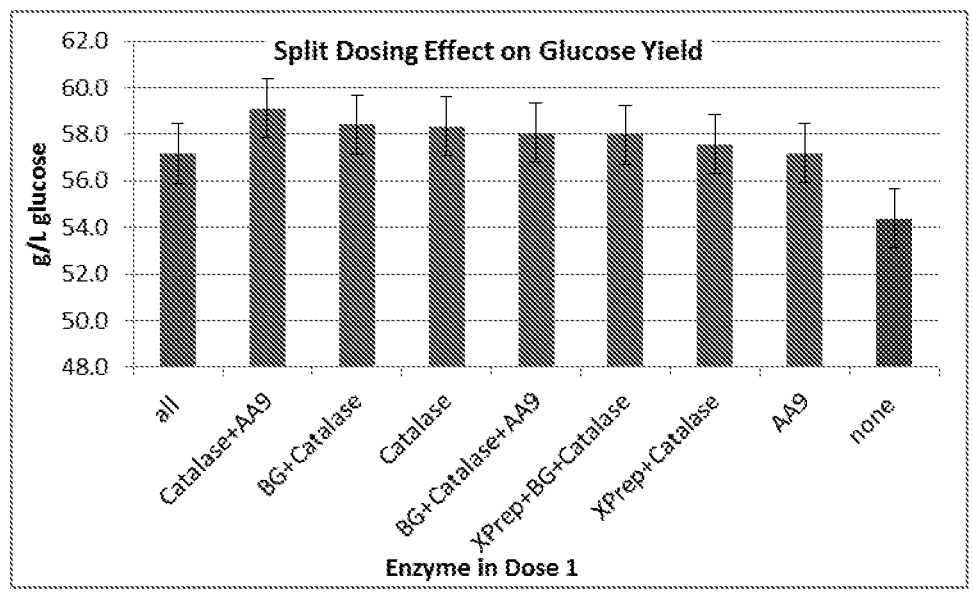
FIG. 3 is a graph showing the glucose yield results of the enzyme dosage schemes detailed in Example 2.

The day 3 hydrolysis results are shown in Table 4 below. When dose 1 contains catalase and/or GH61, a higher glucose or total glucose and xylose yield was achieved. The glucose results are also shown in FIG. 3. Catalase and GH61 were seen to release ~2 g/L glucose more than adding 100% of the enzyme load at Dose 1 (all) and ~4.5 g/L glucose more than adding 100% of the enzyme load at Dose 2 (none). When one or more enzymes (e.g., BG, or XPrep, or BG+XPrep) were added on top of catalase or catalase and GH61 in dose 1, higher glucose yield and higher total glucose and xylose yield were achieved in biomass hydrolysis.

TABLE 4

| | Day 3 sugar yield (g/l) | |
|---|---|---|
| | Glucose | Glucose + xylose |
| All | 57.17 | 83.56 |
| Cat + GH61 | 59.11 | 86.51 |
| BG + cat | 58.42 | 85.50 |
| Cat | 58.34 | 85.07 |
| BG + cat + GH61 | 58.06 | 85.43 |
| XPrep + BG + cat | 57.99 | 84.63 |
| XPrep + cat | 57.57 | 84.42 |
| GH61 | 57.19 | 84.67 |
| None | 54.38 | 81.00 |

Example 3

Determination of the BCA-Equivalent Protein Composition of Monocomponents, Broths and Mixtures of Broths Achieved by BCA Assay and Stain Free Gel Quantitation Samples of protein broths, mixtures of protein broths, and monocomponent proteins were quantified by BCA protein assays and by gel electrophoresis. First, all samples were desalted to remove interfering salts and buffers. This was achieved by equilibration of ECONOPAC® 10DG gravity flow desalt columns (Bio-Rad Laboratories, Inc., Hercules, Calif., USA) with 50 mM sodium acetate pH 5 as column buffer, followed by application of 3 ml of solution containing the protein of interest followed by capture of the desalted sample by elution with 4 ml of column buffer. Diluted samples were measured using a BCA™ Protein Assay Kit (Thermo Fischer Scientific, Waltham, Mass., USA) calibrated by protein standard dilutions of 2.0 mg/mL BSA (Thermo Fischer Scientific, Waltham, Mass., USA). The combined method of desalting and BCA assay is called "desalt BCA".

TGX Stain Free™ or CRITERION® Stain Free 8-16% gels (Bio-Rad Laboratories, Inc., Hercules, Calif., USA) were loaded with, for example, 10 µg desalted protein from fermentation broths. Additionally molecular weight standards (Bio-Rad Laboratories, Inc., Hercules, Calif., USA; unstained) and dilution series of purified monocomponent standard proteins, measured by desalt BCA, were loaded at between 5 to 0.3125 µg per lane. To improve the gel banding resolution, some samples were first deglycosylated by the addition of 0.2 µl of Endo Hf (New England Biolabs, Ipswich, Mass., USA) and incubation overnight at 37° C. For these samples 6.7 to 10 µg of the broth protein was loaded onto gels. The gels were electrophoresed according to manufacturer's recommendations at 200V until the bromophenol blue dye front reached the bottom of the gel. Gels were rinsed 5 minutes with MilliQ water (Millipore, Billerica, Mass., USA) prior to activation (5 minutes) and scanning in an Image Lab™ Scanner (Bio-Rad Laboratories, Inc., Hercules, Calif., USA). Image Lab protein band densities were quantified using Image Lab 3.0 software (Bio-Rad Laboratories, Inc., Hercules, Calif., USA), creating a "band volume" for each identified protein which represented the total integrated Stain Free staining density of that band, and a "lane volume" which represented the total integrated Stain Free lane gel staining density for that lane. If used, the Stain Free compositional amount for any single protein band was represented by the fractional percentage of that band divided by the total staining in the lane (% Stain Free="band volume"/"lane volume"). For samples where addition of Endo Hf enzyme was made, the band volume for that amount of Endo Hf was subtracted from the lane volume to make an adjusted lane volume that represented the composition without Endo Hf.

Purified monocomponent proteins were used to create band volume vs. BCA protein load response curves where the proteins were added by µg as measured by desalt BCA assay and detected as band volume by Stain Free quantitation. For most proteins the ratio of band volume per µg protein was approximately 500,000. The response of most proteins required no adjustment as they had an equal ratio of band volume per µg protein, within the error of these assays (~5%). If a protein showed a significant deviation from this ratio, a calibration curve was made between the protein's band volume and the loaded µg protein as measured by BCA. This allowed adjustment of the band volume relative to the lane volume.

For example, if enzyme Q with band volume of 320,000 in a lane with volume 2,000,000 shows a ratio of band volume per µg BCA loaded protein Q of 400,000 (4/5ths the expected value of 500,000 seen in Stain Free for typical proteins), the band volume for enzyme Q in the quantitation should be multiplied by 5/4 to predict the correct BCA-equivalent amount (to an adjusted band volume of 400,000), and the lane volume should be increased by 1/4th of the band volume for enzyme Q (2,000,000+1/4*320,000=2,080,000, the adjusted lane volume). This leads to an adjusted BCA-equivalent compositional content for protein Q of 400,000/2,080,000=19.2%.

Similarly, if enzyme Z showed a ratio of band volume per µg BCA protein of 600,000 (6/5ths the expected value), the band volume for enzyme Z should be multiplied by 5/6 to predict the correct BCA equivalent amount, and the lane volume should be decreased by 1/6th of the band volume for enzyme Z.

When the adjustments for BCA-equivalent band volume and lane volume were made for all proteins for which there were purified monocomponents, corrected estimates of BCA-equivalent compositions for all broths can be calculated.

Although the invention has been described with reference to the above examples, it will be understood that modifications and variations are encompassed within the spirit and scope of the invention. Accordingly, the invention is limited only by the following claims.

---

What is claimed is:

1. A process of multi-stage hydrolysis of a lignocellulosic material, the process comprising:
   a) a step of contacting a lignocellulosic material with a first enzyme composition comprising one or more cellulolytic enzymes and at least one of an oxidoreductase and an AA9 polypeptide having cellulolytic enhancing activity; and
   b) a saccharification step comprising combining the material of step a) with a second enzyme composition comprising one or more cellulases,
   wherein the first enzyme composition and the second enzyme composition are different enzyme compositions and wherein the process provides increased glucose yield compared to administration of enzymes in a single stage hydrolysis.

2. The process claim 1, wherein the lignocellulosic material is pretreated lignocellulosic material which has been subjected to a pretreatment method selected from steam explosion, liquid hot water treatment and acid pretreatment.

3. The process of claim 1, wherein the oxidoreductase is selected from the group consisting of a catalase, a peroxidase and a laccase.

4. The process of claim 3, wherein the catalase or peroxidase is present in the first enzyme composition as about 1.75% to about 8% of the total enzyme protein added during hydrolysis.

5. The process of claim 3, wherein the laccase is present in the first enzyme composition as about 0.05% to about 1.25% of the total enzyme protein added during hydrolysis.

6. The process of claim 1, wherein the first enzyme composition comprises a catalase selected from the group consisting of: (i) a catalase comprising or consisting of the mature polypeptide of SEQ ID NO: 24; (ii) a catalase comprising or consisting of an amino acid sequence having at least 90% sequence identity to the mature polypeptide of SEQ ID NO: 24; and (iii) a catalase encoded by a polynucleotide comprising or consisting of a nucleotide sequence having at least 90% sequence identity to the mature polypeptide coding sequence of SEQ ID NO: 23.

7. The process of claim 1, wherein the AA9 is present in the first enzyme composition as about 12% to about 18% of the total enzyme protein added during hydrolysis.

8. The process of claim 1, wherein the AA9 polypeptide is selected from the group consisting of: (i) an AA9 polypeptide having cellulolytic enhancing activity comprising or consisting of the mature polypeptide of SEQ ID NO: 8; (ii) an AA9 polypeptide having cellulolytic enhancing activity comprising or consisting of an amino acid sequence having at least 90% sequence identity to the mature polypeptide of SEQ ID NO: 8; and (iii) an AA9 polypeptide having cellulolytic enhancing activity encoded by a polynucleotide comprising or consisting of a nucleotide sequence having at least 90% sequence identity to the mature polypeptide coding sequence of SEQ ID NO: 7.

9. The process of claim 1, wherein the first enzyme composition comprises a cellobiohydrolase I, a cellobiohydrolase II, an endoglucanase I, an endoglucanase II, and an AA9 polypeptide having cellulolytic enhancing activity.

10. The process of claim 1, wherein the first enzyme composition comprises a cellobiohydrolase I, a cellobiohydrolase II, and an AA9 polypeptide having cellulolytic enhancing activity.

11. The process of claim 1, wherein the first enzyme composition comprises a cellobiohydrolase I, a cellobiohydrolase II, an endoglucanase I, an endoglucanase II, and an oxidoreductase.

12. The process of claim 1, wherein the first enzyme composition comprises a cellobiohydrolase I, a cellobiohydrolase II, and an oxidoreductase.

13. The process of claim 1, wherein the first enzyme composition comprises a cellobiohydrolase I, a cellobiohydrolase II, an endoglucanase I, an endoglucanase II, an AA9 polypeptide having cellulolytic enhancing activity and an oxidoreductase.

14. The process of claim 1, wherein the first enzyme composition comprises a cellobiohydrolase I, a cellobiohydrolase II, an AA9 polypeptide having cellulolytic enhancing activity and an oxidoreductase.

15. The process of claim 1, wherein the first enzyme composition further comprises at least one additional enzyme selected from the group consisting of phenol oxidizing enzymes, peroxidases, xylanases, β-xylosidases, acetyl xylan esterases, feruloyl esterases, α-glucuronidases, α-L-arabinofuranosidases, endoglucanases, cellobiohydrolases, β-glucosidases, and lytic polysaccharide monooxygenases.

* * * * *